(12) United States Patent
Khademi et al.

(10) Patent No.: US 11,593,940 B2
(45) Date of Patent: Feb. 28, 2023

(54) METHOD AND SYSTEM FOR STANDARDIZED PROCESSING OF MR IMAGES

(71) Applicant: April Khademi, Toronto (CA)

(72) Inventors: April Khademi, Toronto (CA); Brittany Reiche, Kitchener (CA); Giordano Arezza, Vaughan (CA)

(73) Assignee: Ryerson University, Toronto (CA)

( * ) Notice: Subject to any disclaimer, the term of this patent is extended or adjusted under 35 U.S.C. 154(b) by 276 days.

(21) Appl. No.: 16/954,165

(22) PCT Filed: Dec. 14, 2018

(86) PCT No.: PCT/CA2018/051606
§ 371 (c)(1),
(2) Date: Jun. 15, 2020

(87) PCT Pub. No.: WO2019/113712
PCT Pub. Date: Jun. 20, 2019

(65) Prior Publication Data
US 2021/0158523 A1    May 27, 2021

Related U.S. Application Data

(60) Provisional application No. 62/598,638, filed on Dec. 14, 2017.

(51) Int. Cl.
*G06T 7/00* (2017.01)
*A61B 5/055* (2006.01)
(Continued)

(52) U.S. Cl.
CPC ............ *G06T 7/0014* (2013.01); *A61B 5/055* (2013.01); *G01R 33/4835* (2013.01);
(Continued)

(58) Field of Classification Search
None
See application file for complete search history.

(56) References Cited

U.S. PATENT DOCUMENTS 6,584,216 B1 * 6/2003 Nyul ......................... G06T 5/40
600/407
9,135,698 B2    9/2015 Robitaille et al.
(Continued)

FOREIGN PATENT DOCUMENTS

CA          3085617 A1    6/2019
WO    2019/113712 A1    6/2019

OTHER PUBLICATIONS

International Search Report and Written Opinion dated Feb. 21, 2019 in International Patent Application No. PCT/CA2018/051606 (10 pages).
(Continued)

*Primary Examiner* — Rodney E Fuller
(74) *Attorney, Agent, or Firm* — Tony Orsi; Bereskin & Parr LLP/S.E.N.C.R.L.s.r.l.

(57) ABSTRACT

Methods and systems for processing a digital magnetic resonance (MR) image volume in an image data set using intensity standardization to provide standardized MR image slices are described which generally involve determining an image volume scaling factor to align an image volume landmark of a volume histogram of the digital MR image volume with a reference volume landmark of a reference histogram of a reference image volume; and scaling intensity values of the digital MR image volume based on the image volume scaling factor to generate a scaled digital MR image volume. Methods and systems are also described for generating standardized image slices that can be used in various MR image processing methodologies such as image segmentation and object detection.

50 Claims, 18 Drawing Sheets

(51) Int. Cl.
G01R 33/483 (2006.01)
G01R 33/56 (2006.01)
(52) U.S. Cl.
CPC .............. G01R 33/5608 (2013.01); G06T 2207/10088 (2013.01); G06T 2207/30016 (2013.01)

(56) References Cited

U.S. PATENT DOCUMENTS

| 9,563,950 B2 | 2/2017 | Raj | |
|---|---|---|---|
| 2013/0072782 A1* | 3/2013 | Liu | G01R 33/5608 600/410 |
| 2021/0304402 A1* | 9/2021 | Morgas | G06T 7/12 |

OTHER PUBLICATIONS

Altaf et al., "Cerebral White Matter Hyperintense Lesions are Associated with Unstable Carotid Plaques", European Journal of Vascular and Endovascular Surgery, 2006, 31: 8-13.
Oppedal et al., "Classifying Dementia Using Local Binary Patterns from Different Regions in Magnetic Resonance Images", International Journal of Biomedical Imaging, 2015, 2015: 1-14.
De Groot et al., "Changes in Normal-Appearing White Matter Precede Development of White Matter Lesions", Stroke, 2013, 44: 1037-1042.
Grossman et al., "Perspectives on Multiple Sclerosis," American Journal of Neuroradiology, 1998, 19: 1251-1265.
Wardlaw et al., "What are White Matter Hyper-intensities Made of? Relevance to Vascular Cognitive Impairment", Journal of the American Heart Association, 2015, 4: 001140-1 to -19.
Suckling et al., "Are Power Calculations Useful? A Multicentre Neuroimaging Study: Validation of the Voxel-Based Power Calculations", Human Brain Mapping, Aug. 2014, 35(8): 3569-3577.
Bilello et al., "An Approach to Comparing Accuracies of Two Flair MR Sequences in the Detection of Multiple Sclerosis Lesions in the Brain in the Absence of Gold Standard", Academic Radiology, Jun. 2010, 17(6): 686-695.
Bydder et al., "MR Imaging: Clinical Use of the Inversion Recovery Sequence", Journal of Computer Assisted Tomography, 1985, 9(4): 659-675.
Parker, "Signal-to-noise efficiency in magnetic resonance imaging," Medical Physics, 1990, 17(2): 250-257.
Levy-Cooperman et al., "Misclassified Tissue Volumes in Alzheimer Disease Patients With White Matter Hyperintensities", Stroke, 2008, 39(4): 1134-1141.
Fennema-Notestine et al., "Quantitative evaluation of automated skull-stripping methods applied to contemporary and legacy images: Effects of diagnosis, bias correction, and slice location", Human Brain Mapping, 2006, 27(2): 99-113.
Breiman, "Random Forests", Machine Learning, 2001, 4(1): 5-32.
Ding et al., "Minimum Redundancy Feature Selection From Microarray Gene Expression Data", Journal of Bioinformatics and Computational Biology, 2005, 3(2): 185-205.
Palumbo et al., "Interplay between bias field correction, intensity standardization, and noise filtering for t2-weighted MRI", in 33rd Annual International Conference of the IEEE Engineering in Medicine and Biology Society (EMBS), IEEE, Boston, MA, Aug. 30-Sep. 3, 2011, pp. 5080-5083.
Peng et al., "Feature selection based on mutual information: criteria of max-dependency, max-relevance, and min-redundancy", IEEE Transactions on Pattern Analysis and Machine Intelligence, 2005, 27(8): 1226-1238.
Al Shalabi et al., "Data mining: A preprocessing engine", Journal of Computer Science, 2006, 2(9): 735-739.
Sled et al., "A Nonparametric Method for Automatic Correction of Intensity Nonuniformity in MRI Data", IEEE Transactions Med. Imaging, Feb. 1998, 17(1): 87-97.
Li et al., "Optimal Surface Segmentation in Volumetric Images—a Graph-Theoretic Approach", IEEE Transactions on Pattern Analysis and Machine Intelligence, 2006, 28(1): 119-134.
De Boer et al., "Automatic segmentation of brain tissue and white matter lesions in MRI," in 2007 4th IEEE International Symposium on Biomedical Imaging (ISBI): From Nano to Macro, IEEE, Arlington, VA, Apr. 12-15, 2007, pp. 652-655.
Nyúl et al., "On standardizing the MR image intensity scale", Magnetic Resonance in Medicine, 1999, 42(6): 1072-1081.
De Nunzio et al., "Robust Intensity Standardization in Brain Magnetic Resonance Images", Journal of Digital Imaging. Feb./Dec. 2015, 28(6): 727-737.
Altaf et al., "Brain White Matter Hyperintensities Are Associated with Carotid Intraplaque Hemorrhage", Radiology, 2008, 248: 202-209.
Zhong et al., "Automated White Matter Hyperintensity Detection in Multiple Sclerosis Using 3d T2 FLAIR", International Journal of Biomedical Imaging, 2014, 2014, pp. 1-7.
Reinhard et al., "Color transfer between images", IEEE Computer Graphics and Applications, 2001, 21(5): 34-41.
Malloy et al., "Neuroimaging of white matter in aging and dementia", The Clinical Neuropsychologist, 2007, 21(1): 73-109.
Sdika et al., "Non-rigid registration of multiple sclerosis brain images using lesion inpainting for morphometry or lesion mapping", Human Brain Mapping, Apr. 2009, 30(4): 1060-1067.
Debette et al., "Midlife vascular risk factor exposure accelerates structural brain aging and cognitive decline", Neurology, 2011, 77(5): 461-468.
Wardlaw et al., "Vascular risk factors, large-artery atheroma, and brain white matter hyperintensities", Neurology, 2014, 82(15): 1331-1338.
Valdés Hernández et al., "Close Correlation between Quantitative and Qualitative Assessments of White Matter Lesions", Neuroepidemiology, 2013, 40(1): 13-22.
Khademi et al., "Automatic contrast enhancement of white matter lesions in FLAIR MRI", in 2009 IEEE International Symposium on Biomedical Imaging: From Nano to Macro, Boston, MA, Jun. 28-Jul. 1, 2009, pp. 322-325.
Staals et al., "Stroke subtype, vascular risk factors, and total MRI brain small-vessel disease burden", Neurology, 2014, 83(14): 1228-1234.
Gons et al., "Cigarette smoking is associated with reduced microstructural integrity of cerebral white matter", Brain, 2011, 134: 2116-2124.
Stokking et al., "Automatic Morphology-Based Brain Segmentation (MBRASE) from MRI-T1 Data", NeuroImage, Dec. 2000, 12(6): 726-738.
Ferguson et al., "Cognitive ability and brain structure in type 1 diabetes relation to microangiopathy and preceding severe hypoglycemia", Diabetes, 2003, 52(1): 149-156.
Iglesias et al., "Robust Brain Extraction Across Datasets and Comparison With Publicly Available Methods," IEEE Transactions on Medical Imaging, Sep. 2011, 30(9): 1617-1634.
Rolland et al., "Fast algorithms for histogram matching: Application to texture synthesis," Journal of Electronic Imaging, Jan. 2000, 9(1): 39-45.
Schmidt et al., "An automated tool for detection of FLAIR-hyperintense white-matter lesions in Multiple Sclerosis", NeuroImage, 2012, 59: 3774-3783.
Van Dijk et al., "The Association Between Blood Pressure, Hypertension, and Cerebral White Matter Lesions: Cardiovascular Determinants of Dementia Study", Hypertension, 2004, 44: 625-630.

* cited by examiner

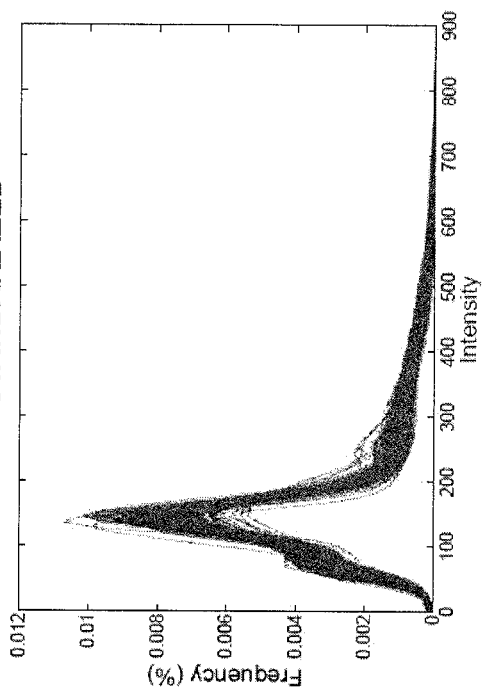
FIG. 1A: MR1
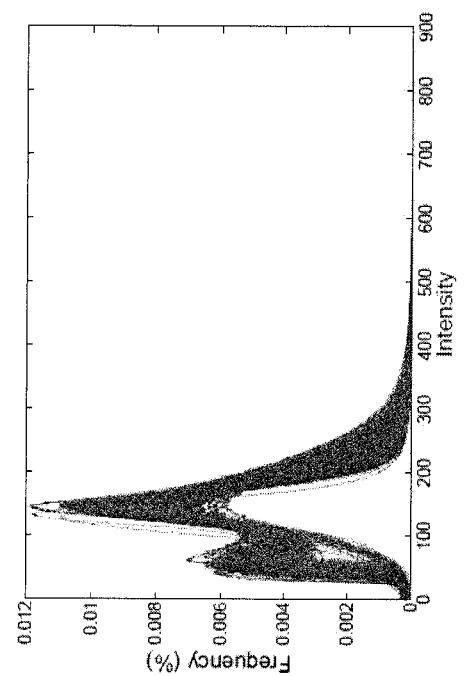
FIG. 1B: MR1
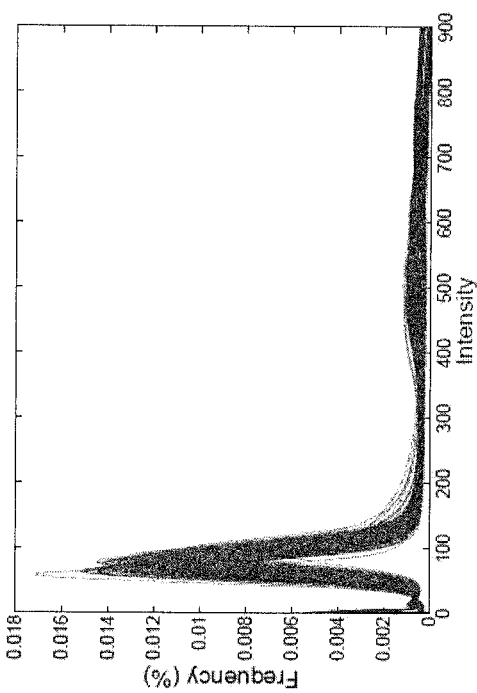
FIG. 1C: MR2
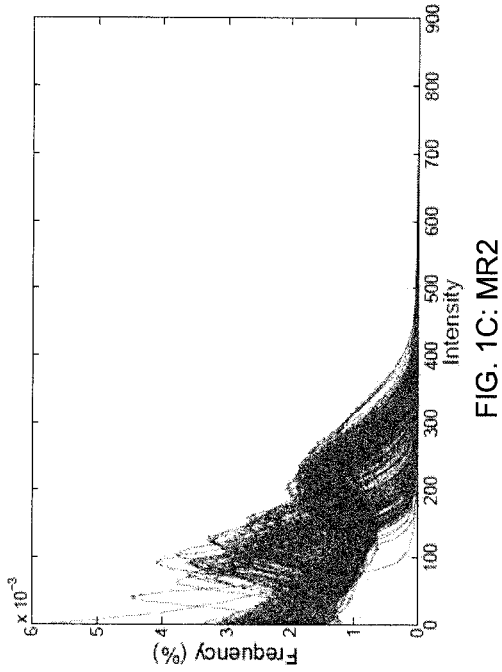
FIG. 1D: MR2

ORIGINAL
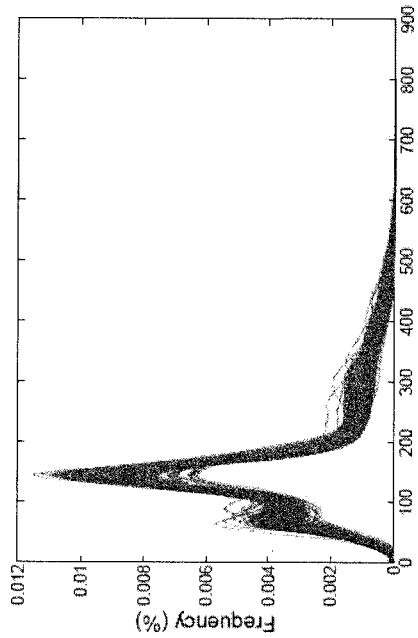
FIG. 1E: MR3
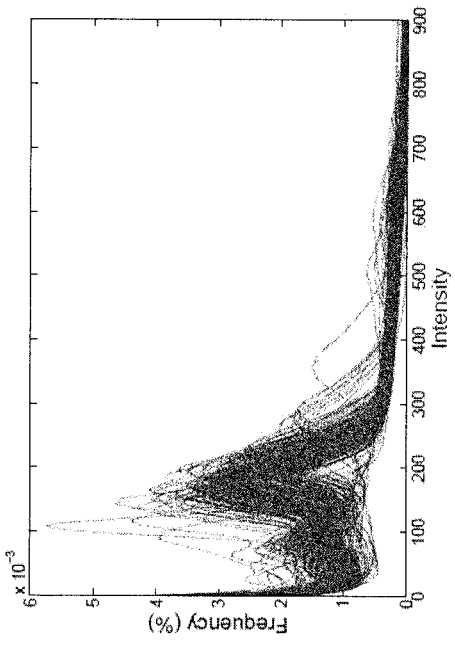
FIG. 1G: MR4
STANDARDIZED
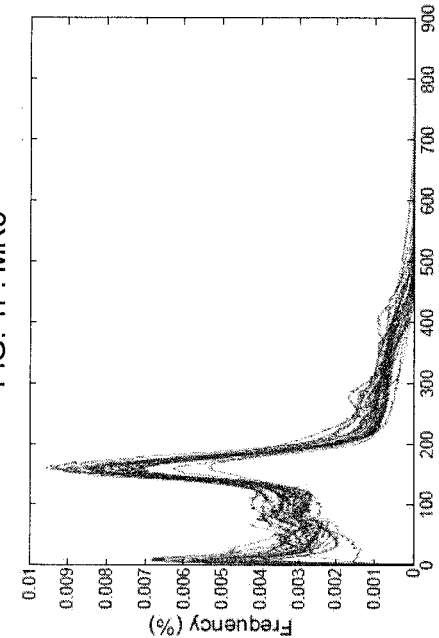
FIG. 1F: MR3
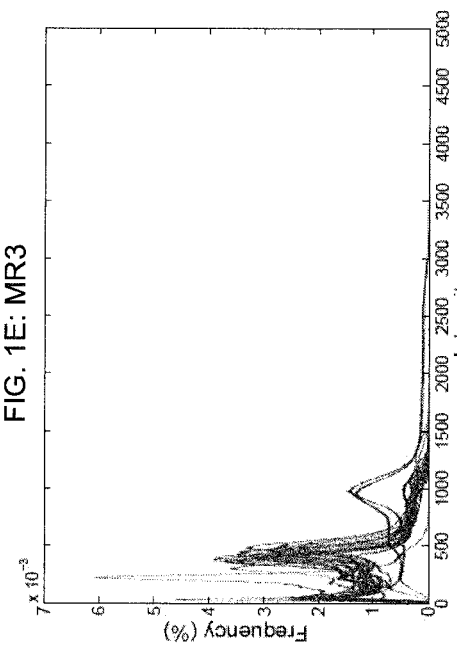
FIG. 1H: MR4

ORIGINAL STANDARDIZED
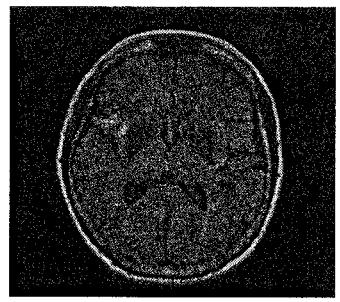
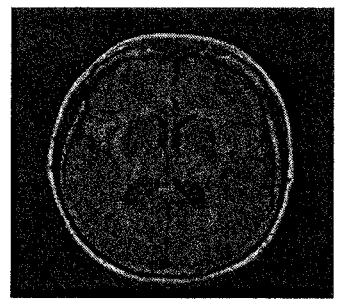
FIG 5A: MR1     FIG. 5B: MR1
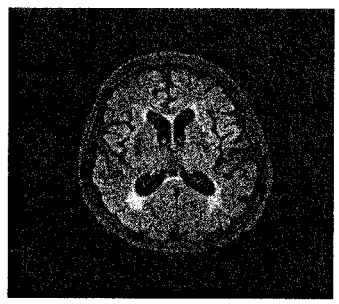
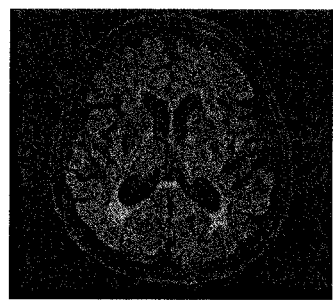
FIG. 5C: MR2     FIG. 5D: MR2
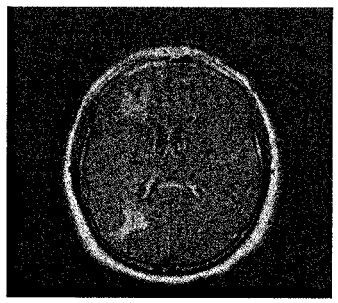
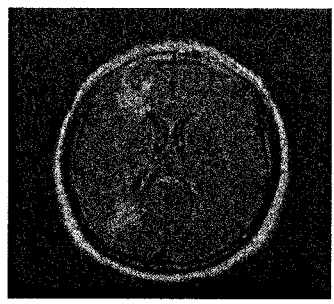
FIG. 5E: MR3     FIG. 5F: MR3
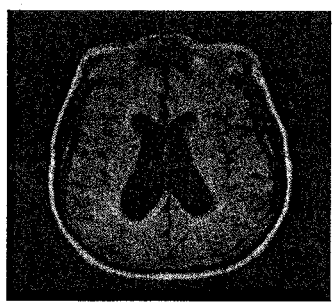
FIG. 5G: MR4     FIG. 5H: MR4

Standardized Image

CSF ($i < 200$)

Brain ($200 < i < 400$)

WML and CSF Artifacts
($i > 400$)

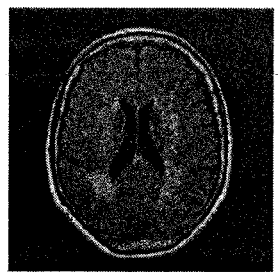 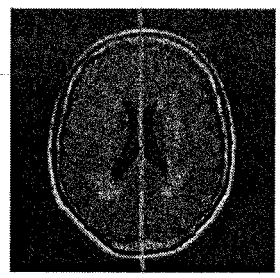 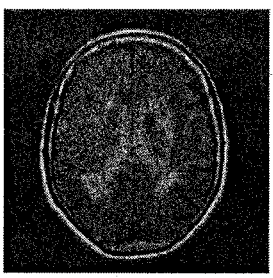 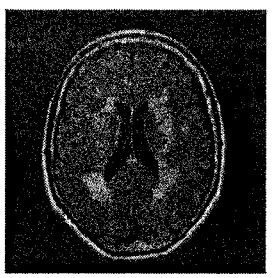
MR1     Midline     Ventricles     WML
FIG. 16A     FIG. 16B     FIG. 16C     FIG. 16D
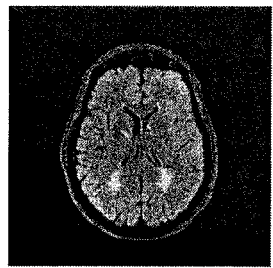 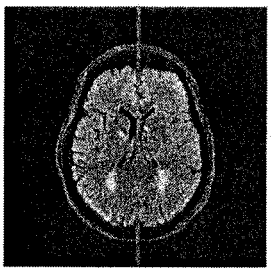 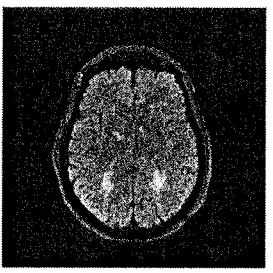 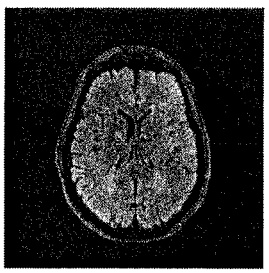
MR2     Midline     Ventricles     WML
FIG. 16E     FIG. 16F     FIG. 16G     FIG. 16H
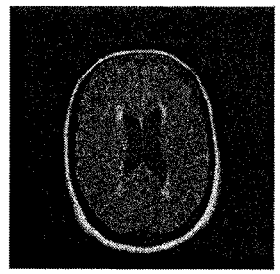 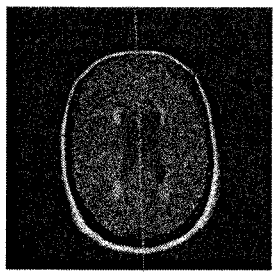 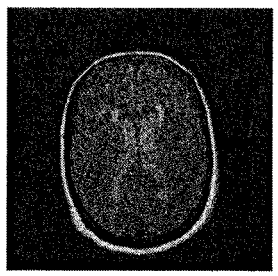 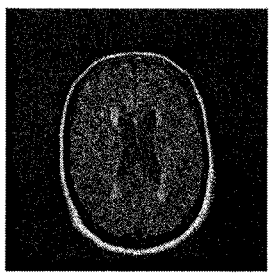
MR3     Midline     Ventricles     WML
FIG. 16I     FIG. 16J     FIG. 16K     FIG. 16L

MR3 - NC

Midline

Ventricles

WML

MR3 - MCI

Midline

Ventricles

WML

MR1 - AD

Midline

Ventricles

WML

METHOD AND SYSTEM FOR STANDARDIZED PROCESSING OF MR IMAGES

CROSS-REFERENCE TO RELATED APPLICATION

This application is a 35 USC 371 national stage entry of International Patent Application No. PCT/CA2018/051606, filed Dec. 14, 2018, which claims the benefit of U.S. Provisional Patent Application No. 62/598,638, filed Dec. 14, 2017, and entitled "METHOD AND SYSTEM FOR STANDARDIZED PROCESSING OF MR IMAGES"; the entire contents of each of which are hereby incorporated by reference.

FIELD

Various embodiments are described herein that generally relate to image processing, and in particular, for a system and methods that may be used to generate standardized MR images.

BACKGROUND

There are several neurological disorders that have a significant impact on the well-being of patients, while presenting a heavy economic burden on healthcare systems. While neurodegenerative disease may respond to therapy for a time, unfortunately, there are currently no cures [40]. People with these diseases may live for some time with certain conditions and will slowly degenerate, leading to reduced brain function, and eventually resulting in death. The economic burden for all neurological disorders in Canada is roughly $60 billion per year, or about 38% of the total burden presented by disease [40].

To reduce mortality rates and long-term disability, as well as to alleviate the associated economic burden, the pathology of neurological disease must be understood so that treatment and intervention can be applied early in disease progression. To this end, researchers have begun to investigate magnetic resonance images (MRI) of the brain to look for clues and precursors of disease. One feature that has been identified on MRI are white matter lesions (WML), which are thought to be expressions of vessel disease [2], and are associated with ischemic stroke [3], Alzheimer's Disease (AD) [2], and multiple sclerosis (MS) [4].

To better understand the relationship between disease and WML, images from large patient cohorts are analyzed. Accurate and quantitative measurement of WML volume, as well as other characteristics, can be used to model disease progression, correlate with outcome/survival, and identify new risk factors [41-48]. As opposed to single centre studies, results from large multicenter studies have more statistical significance and power and therefore, greater clinical utility [49]. Unfortunately, visual analysis of medical images is subjective (observer-dependent), qualitative, error prone, and inefficient, which ultimately affects diagnostic accuracy and the ability to conduct large research studies [7, 50]. Furthermore, digital medical images may be acquired under various conditions including different acquisition parameters, acquisition systems manufactured by different vendors and different image reconstruction algorithms. As a result, there may be variations across multiple images making comparisons between these images difficult.

SUMMARY OF VARIOUS EMBODIMENTS

Various embodiments of an image processing methodology and an associated system that can be used to provide higher quality images for various imaging protocols of various regions of an object (i.e. living or inanimate) are described in accordance with the teachings herein.

In a broad aspect, a method of processing a digital magnetic resonance (MR) image volume from an image data set is provided herein where the method involves performing intensity standardization and the method comprises scaling intensity values of the digital MR image volume based on an image volume scaling factor to align an image volume landmark of a volume histogram of the digital MR image volume with a reference volume landmark of a reference histogram of a reference image volume to generate a scaled digital MR image volume; separating the scaled digital MR image volume into a plurality of scaled digital MR image slices; for each scaled digital MR image slice: generating an image slice histogram; determining an image slice landmark from the image slice histogram; and generating a scaled and shifted digital MR image slice by shifting image slice intensity values by an image slice shifting factor to align the image slice landmark with the image volume landmark.

In at least one embodiment the method further comprises combining the scaled and shifted digital MR image slices to generate a standardized digital MR image volume.

In at least one embodiment, the image volume landmark of the histogram of the digital MR image, the reference volume landmark of the histogram of the reference image volume and the image slice landmarks of the image slice histograms are modes of each corresponding histogram.

In at least one embodiment, the reference image volume is an atlas image volume or another MR image volume from a central MR image database or a second database and the digital MR image volume is from the central MR image database, the second database or another database.

In at least one embodiment, the method further comprises at least one of storing the scaled and shifted digital MR image slices in a data store and displaying at least one of the scaled and shifted digital MR image slices.

In at least one embodiment, the scaling factor is based on a ratio between respective intensity values of the reference volume landmark and the image volume landmark of the histograms of the reference image volume and the digital MR image volume, and the scaling comprises multiplying the digital MR image volume by the scaling factor.

In at least one embodiment, the image slice shifting factor for a given scaled digital MR image slice is based on a difference between respective intensity values of the image slice landmark and the image volume landmark of the histograms of the given scaled digital MR image slice and the scaled digital MR image volume, and the shifting comprises shifting intensity values of the given scaled digital MR image slice by the image slice shifting factor.

In at least one embodiment, the digital MR image volume is of a brain and the intensity values of the image volume landmark, the reference volume landmark and the image slice landmark used for the scaling and the shifting, respectively, correspond to intensity values falling within a predetermined intensity range corresponding to at least one of grey matter tissue, white matter tissue, cerebrospinal fluid and background noise.

In at least one embodiment, intensity values of voxels in the shifted digital image slices that are below zero are set to zero.

In at least one embodiment, when the volume histogram has a different starting point than the reference histogram, the method further comprises normalizing voxel intensities of the digital MR image volume prior to the scaling the digital MR image volume so the volume histogram and the reference histogram have a common starting point.

In at least one embodiment, the method further comprises applying a smoothing function to the image slice histograms of the scaled digital MR images slice prior to the shifting.

In at least one embodiment, the method further comprises performing denoising, and background removal on the digital MR image volume prior to performing the scaling.

In at least one embodiment, the method further comprises performing bias field correction on image slices of the digital MR image volume after performing the denoising and the background removal and before performing the scaling.

In at least one embodiment, the denoising comprises applying a denoising filter to the digital MR image volume to produce a denoised digital MR image volume before performing the scaling of the digital MR image volume.

In at least one embodiment, the background removal comprises removing, cropping, or zeroing pixels in each digital MR image slice of the digital MR image volume with intensity values in an upper or lower H % of a corresponding histogram of each digital image slice, where H is a real number.

In at least one embodiment, the background removal comprises segmenting denoised digital MR image slices into foreground and background masks and assigning pixels in the background mask corresponding to non-tissue pixels an intensity value of zero.

In at least one embodiment, performing bias field correction comprises one of: i) dividing each digital MR image slice by a smoothed or filtered version of itself; ii) dividing the digital MR image volume by a smoothed or filtered version of itself; or iii) using a mode of the foreground mask to fill the background of the digital MR image volume, dividing the digital MR image volume with the filled background by a low-pass filtered version of the digital MR image volume with the filled background, and multiplying the divided digital MR image volume by the foreground mask.

In at least one embodiment, the method comprises: defining the image volume landmark, the reference volume landmark and the image slice landmark; generating the histograms of the digital MR image volume, the reference image volume and the digital MR image slices; and determining intensity values for the image volume landmark, the reference volume landmark and the image slice landmarks for the corresponding histograms.

In at least one embodiment, the MR images are obtained using Fluid-Attenuated Inversion Recovery (FLAIR) MRI, T1-weighted MRI, T2-weighted MRI, Proton Density (PD) weighted MRI, Steady-State Free Precession (SSFP) MRI, Effective T2 (T2*) MRI, Diffusion Weighted Imaging (DWI) MRI, Apparent Diffusion Coefficient (ADC) MRI, Diffusion Tensor (DTI) MRI, and Dynamic Contrast Enhanced (DCE) MRI.

In another broad aspect, a system for processing a digital magnetic resonance (MR) image volume from an image data set is provided herein, wherein the processing comprises performing intensity standardization and the system comprises: a non-transitory memory; at least one processor operable to execute instructions stored in the non-transitory memory to: scale intensity values of the digital MR image volume based on an image volume scaling factor to align an image volume landmark of a volume histogram of the digital MR image volume with a reference volume landmark of a reference histogram of a reference image volume to generate a scaled digital MR image volume; separate the scaled digital MR image volume into a plurality of scaled digital MR image slices; for each scaled digital MR image slice: generate an image slice histogram; determine an image slice landmark from the image slice histogram; and generate a scaled and shifted digital MR image slice by shifting image slice intensity values by an image slice shifting factor to align the image slice landmark with the image volume landmark.

In at least one embodiment, the at least one processor operable to combine the scaled and shifted digital image slices to generate a standardized digital MR image volume.

In at least one embodiment, the at least one processor is further operable to perform an action including at least one of storing the scaled and shifted digital MR image slices in a data store and displaying at least one of the scaled and shifted digital MR image slices.

In at least one embodiment, when the volume histogram has a different starting point than the reference histogram, the at least one processor is further operable to normalize voxel intensities of the digital MR image volume prior to the scaling the digital MR image volume so the volume histogram and the reference histogram have a common starting point.

In at least one embodiment, the at least one processor is further operable to apply a smoothing function to the image slice histograms of the scaled digital MR image slices prior to the shifting.

In at least one embodiment, the at least one processor is further operable to perform denoising, and background removal on the digital MR image volume prior to performing the scaling.

In at least one embodiment, the at least one processor is further operable to perform bias field correction on image slices of the digital MR image volume after performing the denoising and the background removal and before performing the scaling.

In at least one embodiment, the at least one processor is further operable to perform denoising by applying a denoising filter to the digital MR image volume to produce a denoised digital MR image volume before performing the scaling of the digital MR image volume.

In at least one embodiment, the at least one processor is further operable to perform background removal by removing, cropping, or zeroing pixels in each digital MR image slice with intensity values in an upper or lower H % of a corresponding histogram of each digital image slice, where H is a real number.

In at least one embodiment, the at least one processor is further operable to perform background removal by segmenting denoised digital MR image slices into foreground and background masks and assigning pixels in the background mask corresponding to non-tissue pixels an intensity value of zero.

In at least one embodiment, the at least one processor is further operable to perform bias field correction by: i) dividing each digital MR image slice by a smoothed or filtered version of itself; ii) dividing the digital MR image volume by a smoothed or filtered version of itself; or iii) using a mode of the foreground mask to fill the background of the digital MR image volume, then dividing the digital MR image volume with the filled background by a low-pass filtered version of the digital MR image volume with the filled background, and multiplying the divided digital MR image volume by the foreground mask.

In at least one embodiment, the at least one processor is operable to: define the image volume landmark, the reference volume landmark and the image slice landmark; generate the histograms of the digital MR image volume, the reference image volume and the digital MR image slices; and determine intensity values for the image volume landmark, the reference volume landmark and the image slice landmark for the corresponding histograms.

In another broad aspect, a method of processing a digital magnetic resonance (MR) image volume from an image data set is provided herein, wherein the method involves performing intensity standardization and the method comprises: performing volume standardization on intensity values of the digital MR image volume by applying a first transformation function to align an image volume landmark of a volume histogram of the digital MR image volume with a reference volume landmark of a reference histogram of a reference image volume to generate a transformed digital MR image volume; separating the transformed digital MR image volume into a plurality of digital MR image slices; and performing slice refinement for each digital MR image slice by: generating an image slice histogram; determining an image slice landmark from the image slice histogram; and generating a transformed digital MR image slice by applying a second transformation function to the image slice to align the image slice landmark with the image volume landmark.

In at least one embodiment, the first transformation function comprises applying a scaling factor of $\alpha=A/I$ to the image volume histogram image volume where A is an intensity of the reference volume landmark and I is an intensity of the image volume landmark so that the transformed digital MR image volume is a scaled digital MR image volume, and the second transformation function comprises applying a scaling factor of $\gamma=A/J$ to the image slice histogram where J is the intensity of the image slice histogram landmark, and A is intensity of the reference histogram landmark.

In at least one embodiment, the first transformation function comprises applying a scaling factor of $\alpha=A/I$ to the image volume histogram image volume where A is an intensity of the reference volume landmark and I is an intensity of the image volume landmark so that the transformed digital MR image volume is a scaled digital MR image volume so that the transformed digital MR image volume is a scaled digital MR image volume, and the second transformation function comprises shifting image slice intensity values by an image slice shifting factor to align the image slice landmark with the image volume landmark so that the transformed digital MR image slices are scaled and shifted digital MR image slices.

This method may incorporate one or more appropriate aspects of the methods described in accordance with the teachings herein.

In another broad aspect, a system for processing a digital magnetic resonance (MR) image volume from an image data set is provided, wherein the processing includes performing intensity standardization and the system comprises: a non-transitory memory; at least one processor operable to execute instructions stored in the non-transitory memory to: perform volume standardization on intensity values of the digital MR image volume by applying a first transformation function to align an image volume landmark of a volume histogram of the digital MR image volume with a reference volume landmark of a reference histogram of a reference image volume to generate a transformed digital MR image volume; separate the transformed digital MR image volume into a plurality of digital MR image slices; and perform slice refinement for each digital MR image slice by: generating an image slice histogram; determining an image slice landmark from the image slice histogram; and generating a transformed digital MR image slice by applying a second transformation function that aligns the image slice landmark with the image volume landmark.

In at least one embodiment, the at least one processor is configured to apply the first transformation function by applying a scaling factor of $\alpha=A/I$ to the image volume histogram image volume where A is an intensity of the reference volume landmark and I is an intensity of the image volume landmark so that the transformed digital MR image volume is a scaled digital MR image volume and to apply the second transformation function by applying a scaling factor of $\gamma=A/J$ to the image slice histogram where J is the intensity of the image slice landmark, and A is intensity of the reference landmark.

In at least one embodiment, the at least one processor is configured to apply the first transformation function by applying a scaling factor of $\alpha=A/I$ to the image volume histogram image volume where A is an intensity of the reference volume landmark and I is an intensity of the image volume landmark so that the transformed digital MR image volume is a scaled digital MR image volume, and the second transformation function comprises shifting image slice intensity values by an image slice shifting factor to align the image slice landmark with the image volume landmark so that the transformed digital MR image slices are scaled and shifted digital MR image slices.

This system may incorporate one or more appropriate aspects of the system described in accordance with the teachings herein.

In another broad aspect, a method of processing a digital magnetic resonance (MR) image volume from an image data set is provided herein, wherein the method comprises: separating the digital MR image volume into a plurality of digital MR image slices; and performing slice refinement for each digital MR image slice by: generating an image slice histogram; determining an image slice landmark from the image slice histogram; and generating a transformed digital MR image slice by applying a transformation function to the image slice intensities to align the image slice landmark with a reference landmark.

In at least one embodiment, the reference landmark comprises an image volume landmark from a histogram of the image volume, an atlas volume landmark from a histogram of an atlas volume, an image slice landmark from the histogram of an atlas image slice, an image landmark from a histogram of one of the image slices from the image volume, or a histogram of an image slice from a different image volume.

In at least one embodiment, the transformation function comprises applying a scaling factor of $\gamma=A/J$ to the image slice histogram where J is the intensity of the image slice landmark, and A is intensity of the reference landmark so that the transformed digital MR image slices are scaled digital MR image slices.

In at least one embodiment, the transformation function comprises shifting image slice intensity values by an image slice shifting factor to align the image slice landmark with the reference landmark so that the transformed digital MR image slices are shifted and scaled digital MR image slices.

In at least one embodiment, the image volume landmark of the histogram of the digital MR image and the image slice landmarks of the image slice histograms are modes of each corresponding histogram.

This method may incorporate one or more appropriate aspects of the methods described in accordance with the teachings herein.

In another broad aspect, a system for processing a digital magnetic resonance (MR) image volume from an image data set is provided herein, wherein the system comprises: a non-transitory memory; at least one processor operable to execute instructions stored in the non-transitory memory to: separate the digital MR image volume into a plurality of digital MR image slices; and perform slice refinement for each digital MR image slice by: generating an image slice histogram; determining an image slice landmark from the image slice histogram; and generating a transformed MR image slice by shifting image slice intensity values by an image slice shifting factor to align the image slice landmark with a reference landmark.

In at least one embodiment, the reference landmark comprises an image volume landmark from a histogram of the image volume, an atlas volume landmark from a histogram of an atlas volume, an image slice landmark from the histogram of an atlas image slice, an image landmark from a histogram of one of the image slices from the image volume, or a histogram of an image slice from a different image volume.

In at least one embodiment, the transformation function comprises applying a scaling factor of $\gamma=A/J$ to the image slice histogram where J is the intensity of the image slice landmark, and A is intensity of the reference landmark so that the transformed digital MR image slices are scaled digital MR image slices.

In at least one embodiment, the transformation function comprises shifting image slice intensity values by an image slice shifting factor to align the image slice landmark with the reference landmark so that the transformed digital MR image slices are scaled and shifted digital MR image slices.

In at least one embodiment, the image volume landmark of the histogram of the digital MR image or a histogram of the atlas volume or another image volume and the image slice landmarks of the image slice histograms are modes of each corresponding histogram.

This system may incorporate one or more appropriate aspects of the system described in accordance with the teachings herein.

In another broad aspect, a method for performing classification of a digital MR image volume is provided herein, wherein the method comprises: performing image standardization on the digital MR image volume including intensity standardization in accordance with the teachings herein to generate a standardized digital MR image volume; performing feature extraction on the standardized digital MR image volume to generate feature values for a set of features; performing feature normalization on the set of features to obtain a set of normalized feature values; performing classification on the standardized digital MR image volume using the normalized feature values to generate classification results; and performing post processing on the classification results to reduce false positives.

In at least one embodiment, performing the image standardization includes registering an intensity standardized digital MR image volume to a reference volume to spatially align the intensity standardized digital MR image volume to the reference volume before performing feature extraction.

In at least one embodiment, the method further comprises performing an action for at least one of the standardized digital MR image volume and the classification results including at least one of storing at least one of the standardized digital MR image volume and the classification results in a data store and displaying the at least one of the standardized digital MR image volume and the classification results.

In at least one embodiment, the post processing comprises applying mathematical morphology.

In another broad aspect, a system for performing classification of a digital MR image volume is provided herein, wherein the system comprises: a non-transitory memory; at least one processor operable to execute instructions stored in the non-transitory memory to: perform image standardization on the digital MR image volume including intensity standardization in accordance with the teachings herein to generate a standardized digital MR image volume; perform feature extraction on the standardized digital MR image volume to generate features values for a set of features; perform feature normalization on the set of features to obtain a set of normalized feature values; perform classification on the standardized digital MR image volume using the normalized feature values to generate classification results; and perform post processing on the classification results to reduce false positives.

In at least one embodiment, during image standardization the at least one processor may further be configured to register an intensity standardized digital MR image volume to a reference volume to spatially align the intensity standardized digital MR image volume to the reference volume.

In at least one embodiment, the at least one processor is further operable to perform an action for at least one of the standardized digital MR image volume and the classification results including at least one of storing at least one of the standardized digital MR image volume and the classification results in a data store and displaying the at least one of the standardized digital MR image volume and the classification results.

In another broad aspect, a method for operating an MR scanner is provided herein, wherein the method comprises: acquiring a digital MR image volume of an area of interest using the MR scanner; and performing image standardization on the acquired digital MR image volume to generate a standardized digital MR image volume, wherein the standardization includes intensity standardization and is performed in accordance with the teachings herein.

In at least one embodiment, performing the image standardization in this method of operating an MR scanner includes registering an intensity standardized digital MR image volume to a reference volume to spatially align the intensity standardized digital MR image volume to the reference volume before performing feature extraction.

In at least one embodiment, the method further comprises: performing feature extraction on the standardized MR image volume to generate feature values for a set of features; performing feature normalization on the set of features to obtain a set of normalized feature values; performing classification on the standardized MR image volume using the normalized feature values to generate classification results; and performing post processing on the classification results to reduce false positives.

In another broad aspect, an MR system is provided herein wherein the MR system comprises an MR scanner; a non-transitory memory; at least one processor operable to execute instructions stored in the non-transitory memory to: acquire a digital MR image volume of an area of interest using the MR scanner; perform image standardization on the acquired digital MR image volume to generate a standardized digital MR image volume, wherein the standardization includes intensity standardization and is performed in accordance with the teachings herein.

In at least one embodiment, during image standardization the at least one processor of the MR system may further be configured to register an intensity standardized digital MR image volume to a reference volume to spatially align the intensity standardized digital MR image volume to the reference volume.

In at least one embodiment, the at least one processor is further operable to: perform feature extraction on the standardized MR image volume to generate feature values for a set of features; perform feature normalization on the set of features to obtain a set of normalized feature values; perform classification on the standardized MR image volume using the normalized feature values to generate classification results; and perform post processing on the classification results to reduce false positives.

Other features and advantages of the present application will become apparent from the following detailed description taken together with the accompanying drawings. It should be understood, however, that the detailed description and the specific examples, while indicating preferred embodiments of the application, are given by way of illustration only, since various changes and modifications within the spirit and scope of the application will become apparent to those skilled in the art from this detailed description.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now described. The drawings are not intended to limit the scope of the teachings described herein.

FIGS. 1A-1H show histograms of image volumes of different patients for four different MR vendors (MR1-4) before and after processing using the intensity standardization as described herein.

FIGS. 5A-5H show example medical images before and after processing using the image standardization method of FIG. 4. The image data shown in FIGS. 5A and 5B was acquired at TR/TE/TI=9700/141/2200 ms; the image data shown in FIGS. 5C and 5D was acquired at TR/TE/TI=9000/117/2500 ms; the image data shown in FIGS. 5E and 5F was acquired at TR/TE/TI=9000/125/2800 ms; and the image data shown in FIGS. 5G and 5H was acquired at TR/TE/TI=8002/127.6/2000 ms.

FIGS. 16A-16L show sample results of midline plane estimation, as well as WML and ventricle segmentation, across different scanner vendors in the DB1 ischemic disease dataset.

Figure 2:
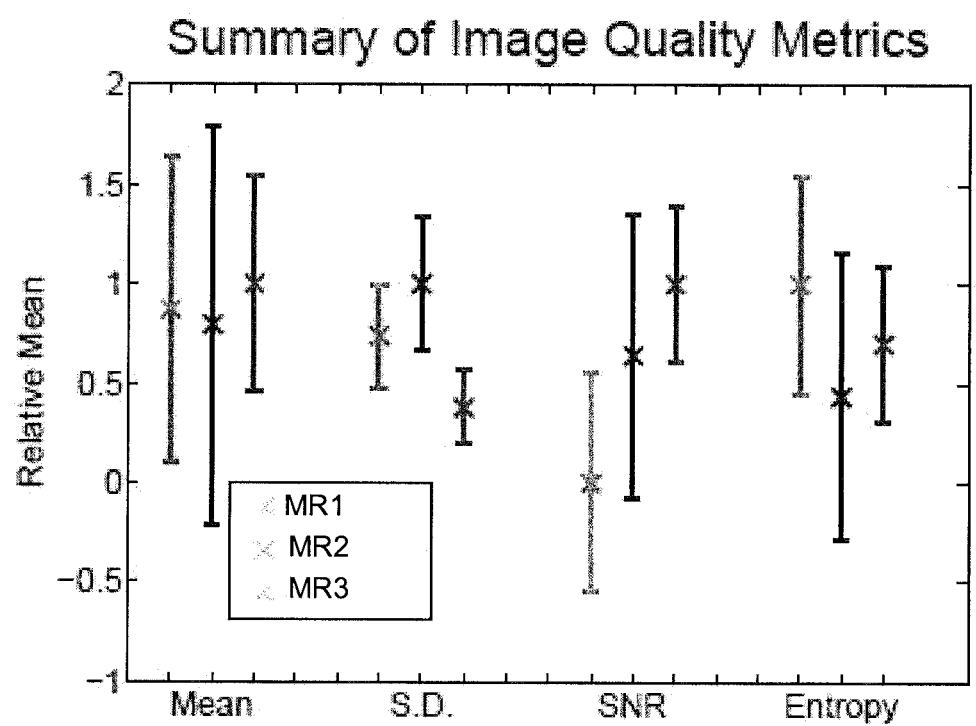
FIG. 2 shows a graph of image metrics indicating inter- and intra-scanner variability.

Further aspects and features of the example embodiments described herein will appear from the following description taken together with the accompanying drawings.

DETAILED DESCRIPTION OF THE EMBODIMENTS

Various embodiments in accordance with the teachings herein will be described below to provide an example of at least one embodiment of the claimed subject matter. No embodiment described herein limits any claimed subject matter. The claimed subject matter is not limited to devices or methods having all of the features of any one of the devices or methods described below or to features common to multiple or all of the devices and or methods described herein. It is possible that there may be a device or method described herein that is not an embodiment of any claimed subject matter. Any subject matter that is described herein that is not claimed in this document may be the subject matter of another protective instrument, for example, a continuing patent application, and the applicants, inventors or owners do not intend to abandon, disclaim or dedicate to the public any such subject matter by its disclosure in this document.

It will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, magnetic or electrical connotation. For example, as used herein, the terms coupled or coupling can indicate that two elements or devices can be directly connected to one another or connected to one another through one or more intermediate elements or devices via a magnetic signal, an electrical signal or a mechanical element, depending on the particular context.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term, such as by 1%, 2%, 5% or 10%, for example, if this deviation would not negate the meaning of the term it modifies.

Furthermore, the recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed, such as 1%, 2%, 5%, or 10%, for example.

At least a portion of the example embodiments of the systems, devices, or methods described in accordance with the teachings herein may be implemented as a combination of hardware or software. For example, a portion of the embodiments described herein may be implemented, at least in part, by using one or more computer programs, executing on one or more programmable devices comprising at least one processing element, and at least one data storage element (including volatile and non-volatile memory). These devices may also have at least one input device (e.g., a keyboard, a mouse, a touchscreen, and the like) and at least one output device (e.g., a display screen, a printer, a wireless radio, and the like) depending on the nature of the device.

It should also be noted that there may be some elements that are used to implement at least part of the embodiments described herein that may be implemented via software that is written in a high-level procedural language such as object-oriented programming. The program code may be written in C, C++, Python, Matlab or any other suitable programming language and may comprise modules or classes, as is known to those skilled in object-oriented programming. Alternatively, or in addition thereto, some of these elements implemented via software may be written in assembly language, machine language, or firmware as needed.

At least some of the software programs used to implement at least one of the embodiments described herein may be stored on a storage media (e.g., a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions, such as program code, for one or more processors. The program code may be preinstalled and embedded during manufacture and/or may be later installed as an update for an already deployed computing system. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

In addition, it should be understood that the term "image" as used herein refers to a digital image that has been obtained using an imaging device and is a collection of digital values that is readable by an electronic device. The same holds true for an "MR image". Therefore the terms "digital image" and "image" may be used interchangeably. Also, the terms "digital MR image" and "MR image" may be used interchangeably. Also, the term "image data" or "MR image data" refers to values of a digital image that can be transmitted amongst electronic devices and stored in a data store. Therefore, the terms "digital MR image data" and "MR image data" may be used interchangeably. Also, the terms "digital image data" and "image data" may be used interchangeably.

In addition, it should be understood that the term "image volume" as used herein refers to a set of image slices that represent a volume obtained from the same object/anatomy/patient using an imaging device and is a collection of digital values that is readable by an electronic device. The same holds true for an "MR image volume". Therefore, the terms "digital image volume" and "image volume" may be used interchangeably. Also, the terms "digital MR image volume" and "MR image volume" may be used interchangeably. Also, the term "image volume data" or "MR image volume data" refers to values of a set of digital image slices that can be transmitted amongst electronic devices and stored in a data store. Therefore, the terms "digital MR image volume data" and "MR image volume data" may be used interchangeably. Also, the terms "digital image volume data" and "image volume data" may be used interchangeably.

Magnetic resonance imaging (MRI) is one imaging modality that can be used to generate images with sufficient contrast resolution of patient anatomy for medical analysis without the use of ionizing radiation. For many years, T1-weighted and T2-weighted MRI were the sole modalities used by clinicians to diagnose and treat neurodegenerative disease. However, a newer modality, known as Fluid-Attenuated Inversion Recovery (FLAIR) MRI, has been recently gaining momentum and is becoming the preferred modality for neurodegenerative disease detection and analysis [51-55].

FLAIR is advantageous over T1-weighted and T2-weighted sequences because the cerebral spinal fluid (CSF) signal is nulled, which allows hyperintense lesions and subtle changes at the periphery of the hemispheres and periventricular regions to be better visualized [51]. T1-weighted and T2-weighted images are less ideal for this visualization, as T1-weighed MRI generally results in misclassification of tissues in subjects with WML [56] and T2-weighted MRI is less robust at identifying intensity changes adjacent to CSF when compared to FLAIR [55]. WML are understood as localized areas of high MR signal intensity, and are thought to be expressions of vessel disease [2]. The prevalence of these lesions can be associated with ischemic stroke [3], Alzheimer's Disease (AD) [2] and multiple sclerosis (MS) [4].

Although FLAIR is now gaining momentum as the preferred modality for neurodegenerative disease detection and analysis, only a few methods of analysis exist for FLAIR, and novel methods that can operate on large patient databases are much needed. To better understand the relationship between these diseases and WML, MR images from large patient cohorts may need to be analyzed and correlated with patient outcomes [5]. The results of studying a large patient cohort can have more statistical significance, and therefore, greater clinical utility [6]. The manual analysis of WML can be laborious and subject to observer variability [7]. As such, a system and method to automate WML analysis may be a preferred alternative, as automated analysis can be used to compute lesion volumes for a large database objectively, accurately, and efficiently compared to using known techniques that are not possible without using a computer.

However, designing image processing methods for multicentre (MC) databases is challenging due to the variability in data created by different scanner vendor hardware and software, different acquisition protocols (including acquisition parameters such as magnetic field strength, repetition time (TR), echo time (TE), and inversion time (TI)), and patient dependent artifacts. These sources of variability ultimately create differences in various image properties such as image intensity (i.e. the intensity values of tissues), image contrast, image quality, spatial location of anatomies, noise, and voxel size, all which do not permit for image processing methods to be applied on all MC databases consistently. Many existing MRI image processing methods tend to be designed for a specific database (i.e. images acquired using identical protocols, or sometimes using the same scanner), and are not known to generalize well to other datasets due to MC data variability [55, 57]. Furthermore, it is known that scanner vendors are known to have an effect on segmentation accuracy due to differences in acquisition artifacts and reconstruction algorithms [58, 38].

The parameters TR, TE, and TI are known to affect image contrast, and TE and TR can be related to the signal-to-noise ratio (SNR) of an image [8]. The magnetic field strength of the MR scanner may also affect image quality, as a higher field strength can result in lower levels of acquisition noise. Image resolution may also have an effect on SNR, as it is directly related with voxel size [9, 10]. Additionally, the generally proprietary image reconstruction algorithms implemented by each MR scanner manufacturer can have an effect on resultant images, as they determine the properties and characteristics of the noise distribution [11]. For example, the basis for the differences may come from using differing k-space algorithms [12]. In particular, it has been found that the MR scanner vendor can have a significant effect on image smoothness [12].

Therefore, as a result of the differences between acquisition parameters, scanner manufacturer hardware, image reconstruction algorithms, and patient-dependent artifacts, certain image properties, such as at least one of image contrast, image intensity, and image SNR can vary. A further consequence of this variability lies in the analysis of longitudinal data, which is critical to the modelling of neurological disease progression. These sources of variability make it very difficult, if not impossible, to accurately compare images from different time points, especially if the difference is small.

For the purposes of the present disclosure, image data originating from various clinical institutes and medical studies/trials (and therefore different scanning devices and protocols) may be considered to be image data within a MC dataset. The sources of variability in an MC MRI dataset can include acquisition noise, bias field, intensity non-standardness, voxel resolution, and patient orientation.

Acquisition noise can be present in the form of additive noise to the spatial domain of the images and can be largely dependent on the acquisition protocol used.

Bias field artifact, or intensity inhomogeneity, may be presented as a low frequency change in pixel intensities within the same tissue class. For example, in an MR scanner with a magnet generating a magnetic field with 1.5 Tesla (T) of field strength, this variation can exceed 30% of the MR signal's actual value [13].

Intensity non-standardness describes how a subject can have two MRI scans acquired from the same anatomy, with the same MR scanner and the same MR scan protocol but the resulting MR images, can yield different pixel intensities for the same anatomies [14]. The effect of intensity non-standardness can be further amplified when comparing images acquired using different MR scanners, in MC data for example, resulting in the same tissues being expressed by different intensity values, which can severely affect the accuracy of automated segmentation and registration algorithms [15]. FIGS. 1A, 1C, 1E and 1G, which plot the intensity distribution of several MRI volumes of different patients, highlight this effect, as they show differences in intensity distributions within various MR scanner manufacturers, and show the results of performing intensity standardization in accordance with the teachings herein.

Patient orientation can also contribute to variability in the spatial coordinates of anatomy in the resultant image, as the position of the brain can change for each subject. Patient anatomy and pathology can also add variability to MC MR images. For example, in an MR image database of subjects with vascular disease, subjects can have varying lesion loads, which can affect the characteristics of the image and its corresponding histogram, due to a varying prevalence of high intensity pixels in the brain.

It should be noted that use of the term histogram of an image slice or an image volume as used throughout this description is meant to cover a histogram that is generated using the intensity values of the corresponding image slice or image volume.

Image variability from inter-scanner and intra-scanner differences can be identified by examining image quality measurements. An example of such variability is shown in FIG. 2, which summarizes measurements of mean signal, standard deviation, SNR, and spatial entropy for an entire image database, as a function of MR scanner manufacturer. It may be observed that the mean signal between MR scanners can vary. Like the mean signal, the standard deviation can also vary across MR scanner manufacturer indicating larger or smaller variability in intensity values. SNR measurements can be used to show that differences in relative noise levels across MR scanners can exist. Similarly, as discussed, entropy can quantify the randomness of image data which can be related to noise and bias field levels. These image quality metrics can be used to indirectly quantify the artifacts of acquisition noise, bias field, etc., and can demonstrate that these image characteristics can be dependent on the MR scanner manufacturer. Although patient anatomy and pathology can also affect these measurements, there is some overlap in the metrics for each MR scanner type, for different patients regardless. Therefore, these metrics can indicate an average trend for each MR scanner, and highlights MC variability. It is therefore preferable to reduce or even eliminate MC variability automatically in order to yield more consistent images, which will in turn increase the robustness and accuracy of algorithms that can be used for further image analysis.

From an image processing perspective, the MC variability described above can introduce inconsistencies in contrast, intensity, and voxel resolution between images, which may affect automated algorithms [15]. Algorithms that rely on pixel intensity for feature extraction will have trouble generalizing in MC data, since the distribution of intensity values for the same features can be variable across the images being processed. As another example, consider a thresholding-based algorithm: a certain threshold may be considered ideal for the segmentation of an object in one image, but due to intensity non-standardness and contrast differences, the same threshold value may unlikely be applicable to other images for segmenting the same object. In the past, algorithms tended to be designed for a specific image database (i.e. images acquired using identical protocols, or sometimes the same MR scanner), and are not known to generalize well to other datasets due to data variability in MC images originating from different image databases [16]. This variability has not yet been addressed for FLAIR MRI, and approaches for T1-weighted and T2-weighted images [14] are not easily applied to FLAIR, as changes to the intensity scale can suppress the appearance of WML, reducing the clinical utility of the images.

For these reasons, the inventors have created an image standardization framework for MR images that can be used to reduce the variability of MR images obtained from MC studies. For example, the image standardization framework may be applied to FLAIR, T1-weighted, T2-weighted, Proton Density (PD) weighted, Steady-State Free Precession (SSFP), Effective T2 (T2*), Diffusion Weighted Imaging (DWI), Apparent Diffusion Coefficient (ADC), Diffusion Tensor (DTI), and Dynamic Contrast Enhanced (DCE) MR images. In accordance with the teachings herein, the standardization framework can be used to normalize the characteristics of image data obtained using these imaging modalities such that corresponding image properties such as contrast, intensity, and resolution become more uniform across different images. Standardization of images can allow for the application of the same image processing algorithms to large datasets originating from disparate image databases, institutions and scanning devices.

Furthermore, the standardization performed according to the teachings herein may permit differences between images to be detected which may otherwise be regarded simply as artifacts from acquisition using conventional methods. The standardization methods described herein may also allow longitudinal images to be normalized to the same intensity scale, allowing for robust and consistent analysis of each time point. Additionally, algorithms do not need to be modified and tuned separately for each scanner (rendering more consistent results) and different patients within the same MC database can be compared more fairly.

Images considered for verification of the framework include 500 neurological 3T FLAIR MRI image volumes (providing a total of 24,000 image slices) from 9 centres of patients with vascular disease noted as DB1, 3500 neurological 3T FLAIR MRI image volumes (providing a total of 120,000 image slices) from 58 centres of patients with dementia denoted as DB2, and DB3 which is a neurological 1.5T FLAIR MRI dataset that contains 27 image volumes (providing a total of 945 image slices) from a single centre of patients with vascular disease. Over all the datasets (DB1, DB2, DB3) three scanner vendors were used to collect this data, which included GE, Siemens and Philips manufacturers. In no particular order, the vendors have been anonymized to MR1, MR2, MR3 and MR4. Note that MR1-3 corresponds to 3T imaging, and MR4 is one of the vendors manufacturers but at 1.5T. Standardization and analysis of this diverse MC dataset may yield insights into disease processes with greater statistical power.

To further show the utility of the standardization framework described herein WML segmentation [16], [17] may be employed on MC data that has been processed using the standardization framework.

An existing WML segmentation algorithm that accounts for partial volume averaging (PVA) [17] can be used to determine whether the standardization framework can maintain or increase segmentation accuracy. As also described in more detail below, an evaluation of the standardization framework shows that the standardization can ease the complexity of further analysis algorithms of FLAIR images across all subjects and MR scanners.

Figure 3:
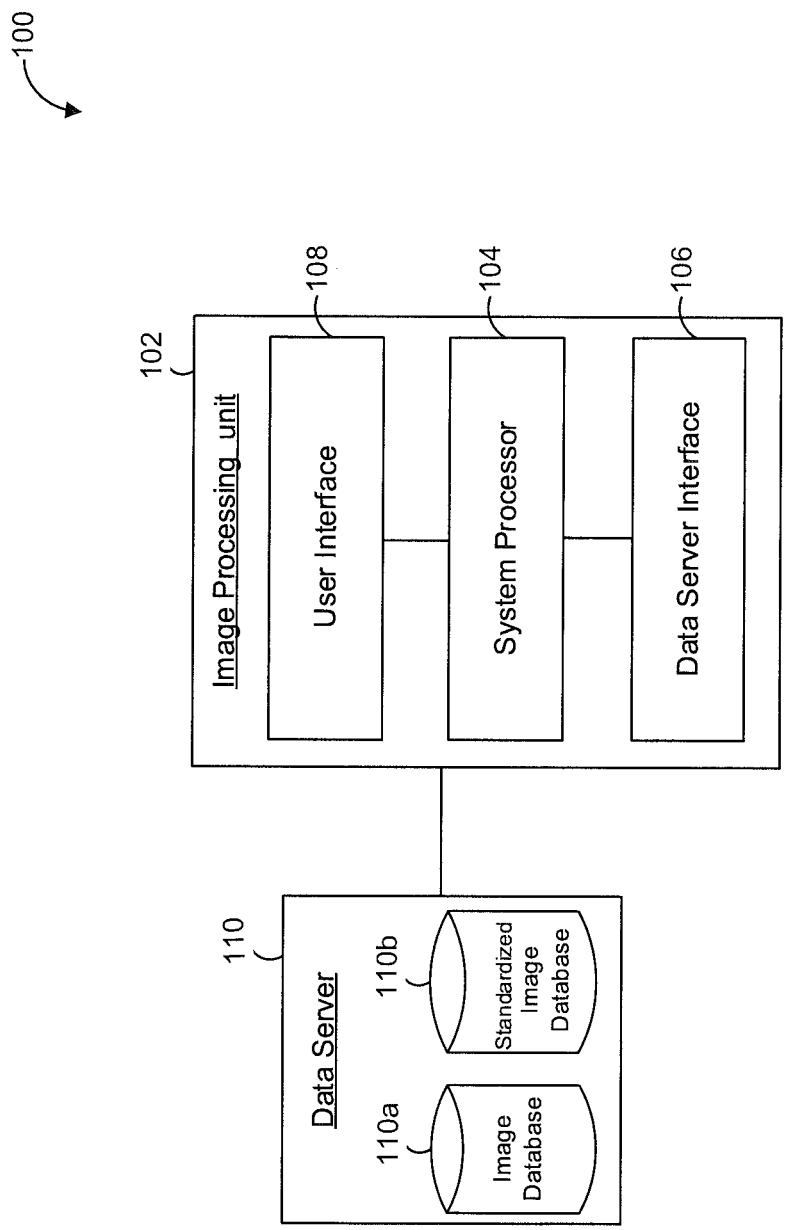
FIG. 3 is a block diagram of an example embodiment of an image processing system in accordance with the teachings herein.

Referring now to FIG. 3, shown therein is a block diagram of an example embodiment of an image processing system 100 that is operable to generate standardized MR images in accordance with the standardization framework disclosed herein. The image processing system 100 comprises an image processing unit 102 having a system processor 104, a data server interface 106 and a user interface 108 as well as a data server 110 having an image database 110a and a standardized image database 110b. In the example embodiment that is shown, the image processing system 100 includes the data server 110. In other embodiments, the data server 110 may be physically remote from the image processing unit 102 and connected to the image processing unit 102 via a communication network, such as the Internet or an Intranet. For example, the data server 110 may be a central repository. In other embodiments, there may be more than one data server which collectively implement a distributed repository but provides the same functionality as the data sever 110. In other embodiments, other components may be included in the system 100.

The image processing system 100 may be part of an MR scanner, which can perform image processing and analysis using image standardization after the image data is acquired, and the processed images and analysis data can then be sent to a clinical database for storage. In some embodiments, the original image data can also be stored in the clinical database as some clinicians may wish to view unprocessed image data as well as the processed image data.

Alternatively, in some embodiments, the image processing system 100 may be a backend system (i.e. a computer or server with a database) that accepts the acquired image data, performs image processing using at least one of the image standardization methods described herein, and then stores the standardized images and/or analysis results in the database or another data store. An image viewer and analysis toolkit may then be used to access the acquired image data, the standardized images and/or the analysis results.

Alternatively, in some embodiments, the image processing system 100 may be a standalone system that is in communication with a research database that has a large amount of data that is collected through various MR platforms, and the system 100 provides centralized tools to process and/or analyze the data in the research database.

Images that may be handled by the image processing system 100 include MR images that can be acquired in a variety of settings such as, but not limited to, MR images acquired using varying acquisition parameters, using various MR scanner manufacturers, for different patients and for different patient orientations. In some embodiments, the MR images may be obtained in an MC setting. In some embodiments, the MR images may be obtained using the same MR scanner, which may include varying or not varying other parameters.

Images can be processed by the image processing unit 102 in accordance with an embodiment of the standardization framework described herein. The image processing unit 102 may be implemented in a variety of manners, including but not limited to, using one or more computer processors in a computer system to execute one or more image processing software programs, using one or more graphic processing units (GPUs), as an application in a cloud-based or distributed computing environment, or as an embedded programmable system such as a field programmable gate array (FPGA) or an in application-specific integrated circuit (ASIC).

In the system 100, the image processing unit 102 comprises system memory (not shown) and the system processor 104. The system memory can be used for the temporary or permanent storage of image data, system configurations, instructions for execution by the system processor 104 and user instructions. The system processor 104 can be operable to process MR images and generate standardized MR images based on the executable instructions and/or user instructions. The system processor 104 is programmable to process the MR images selected for standardization. The system processor 104 may also be used to control and/or coordinate the operation of the other components of the image processing unit 102, including the user interface 106, the data server interface 108, and memory.

The user interface 106 can be configured to receive instructions from a user who wishes to interact with the image processing unit 102. For example, the user interface 106 may be configured to accept user input to allow a user of the image processing system 100 to select at least one MR image from an image storage unit such as the data server 110 for processing, to select values for particular parameters used in the methods described herein or to select between different implementation options for the methods described herein. In some embodiments, the user interface 106 may be a graphical user interface that is displayed on a display screen (not shown) and includes graphics such as thumbnails of images being processed as well as larger sized digital images without and with image standardization. In other embodiments, the user interface 106 may be a command line interface, which may be useful where a large number (e.g. hundreds or thousands of images) of MR images are to be processed. Multiple commands for the image processing unit 102 may be provided as a script, written in an appropriate scripting or programming language such as C++, C #, Javascript, Perl, Python, or Matlab™. The commands received from the user interface 108 may be provided to the system processor 104 for execution. In yet other embodiments, the user interface 106 may provide both a command line and a graphical interface. Alternatively, in other embodiments, the parameters that affect the operation of the methods described herein may be standard and pre-defined.

The data server interface 106 is configured to enable the image processing unit 102 to access image data stored in the data server 110. While it is shown in FIG. 3 that image data for unprocessed MR images and processed standardized MR images, according to the standardization framework, are stored in the data server 110, it may be understood that the image data can be stored within the memory of an integrated storage device of the image processing unit 102 or in another storage device (not shown) including, but not limited to, a disk drive, an optical drive, a CD, a USB flash drive, solid state memory or on the cloud, for example. When the storage device is integrated within the image processing unit 102, the data server interface 106 is configured to access image data stored within the integrated storage device.

The data server 110 may be used to store the raw MR image data, which is MR image data that has not undergone image standardization in accordance with the teachings herein. In some cases, the MR image data may be from a MC data set. The data server 110 may also store standardized images and/or analysis results generated by the image processing unit 102. In the present embodiment, a first data store, such as the image database 110a may be used to store the raw MR image data and a second data store such as the standardized image database 110b may be used to store the standardized MR image data and/or analysis results. While the data server 110 of the present embodiment is indicated as two data stores 110a and 110b, in other embodiments, the same data store may be used to store both the raw MR image data set and the standardized images.

In some embodiments, the data server 110 may be provided as a storage server system that is separate from the image processing unit 102. For example, the data server 110 may be accessible using the data server interface 106 over a network connection. In such a configuration, the data server 106 may include a compatible network access interface device (not shown) to allow the image processing unit 102 to access the data server 110 over the network. In other embodiments, the data server 110 may be a distributed storage system, such as a cloud-based storage system. In this case, the data server interface 106 may be operable to generate application programming interface (API) calls to read and write to the cloud-based data sever 110.

Figure 4:
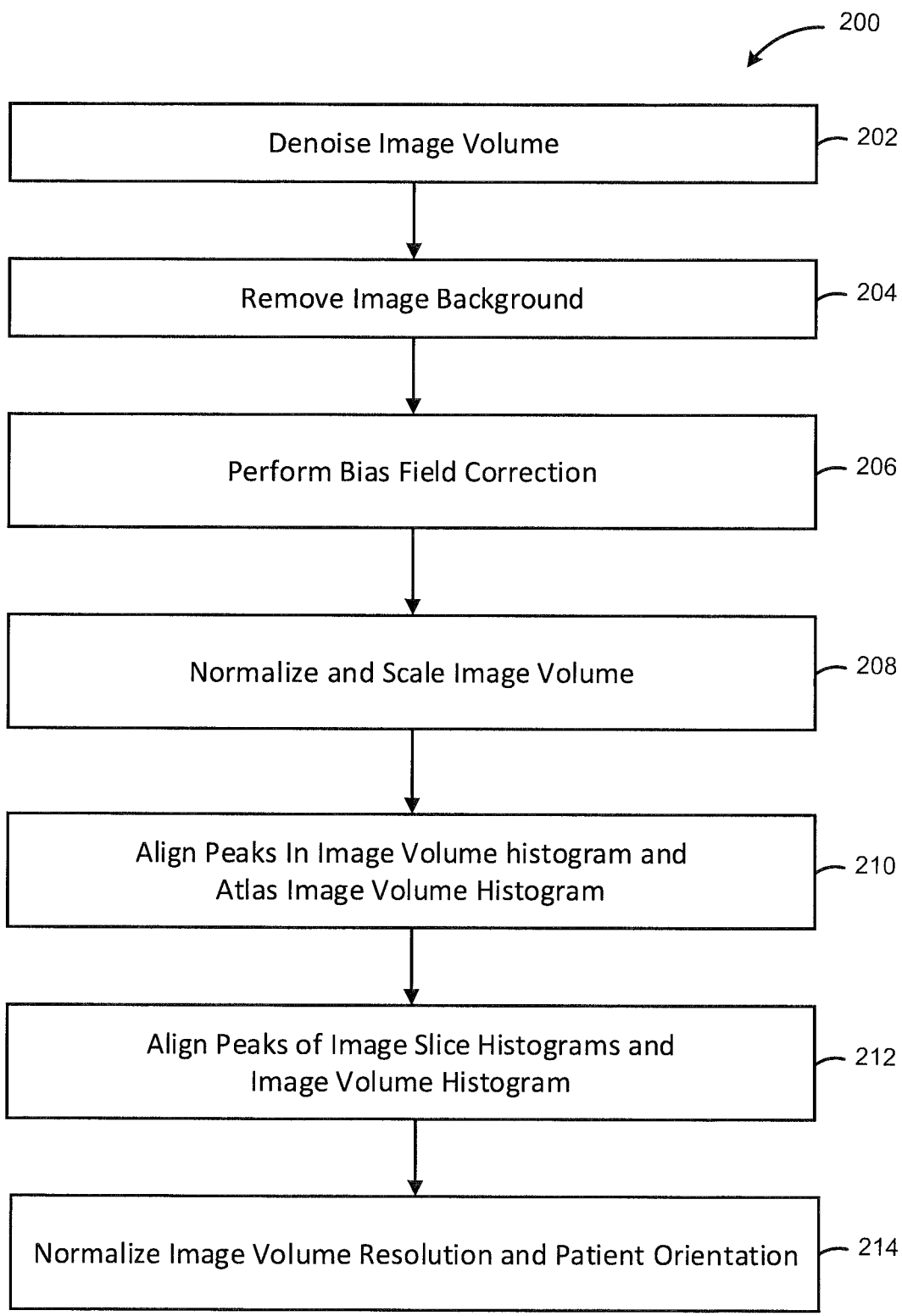
FIG. 4 is a flowchart of an example embodiment of an image standardization method in accordance with the teachings herein.

Referring now to FIG. 4, shown therein is a flow chart of an example embodiment of an image standardization method 200 for standardizing images of a MC data set. In this example embodiment, intensity standardization involves acts 202 to 212, with some of these acts being optional as described below. The addition of act 214, which is optional, results in an image standardization methodology. Therefore, acts 202 to 214 may be referred to as image standardization which involves intensity and spatial normalization.

As noted previously, the standardization framework may be used to normalize or reduce differences due to at least one of acquisition noise, bias field, intensity non-standardness, voxel resolution, and patient orientation. This framework may be used to output images with similar intensity histogram distributions (i.e. the corresponding histograms are aligned and have similar shape/range characteristics), equal resolution, and normalized patient orientation. Since MR images generally correspond to a volume of an anatomy, the pixels within an MR image volume may be regarded to be voxels that are arranged in three dimensions such that an image volume can be defined as $Y(x_1, x_2, x_3)$. A reference image volume may be used as the standard for the standardization framework can be defined as $A(x_1, x_2, x_3)$. The reference image volume may be another image volume, or an atlas volume. For the purposes of the present disclosure $x_1$ and $x_2$ can be used to denote spatial coordinates in each image slice, and $x_3$ can be used to represent the slice number in each volume.

At act 202, the image volume $Y(x_1, x_2, x_3)$ may be processed to remove acquisition noise to produce noise reduced image volume $R(x_1, x_2, x_3)$ that includes noise reduced image slices $R(x_1, x_2)$. An appropriate denoising filter may be used for the denoising process. For example, a median filter can be applied to all image slices within the image volume in the spatial domain to perform denoising without modifying any important information in the MR image and generating filtered image slices. Low pass filtering, averaging, bilateral filters, as well as any 3D denoising filters may be used depending on the particular image characteristics as is known by those skilled in the art.

At act 204, spurious noise and outliers may be removed by applying a method such as the Percentile Contrast Stretch. In the present embodiment, this may involve removing or cropping or zeroing pixels with intensities in the upper and lower H % of a histogram of the image volume $Y(x_1, x_2, x_3)$, where H is a real number and may be set to 2%, for example.

To segment the denoised and outlier-removed image volume into foreground and background masks, a K-means classifier (k=2) may be applied. The K-means classifier can be used as it is able to discriminate between low intensity background pixels and higher intensity tissue pixels in an unsupervised manner, and without having to implement hard thresholds making it more robust to MC variability. The background mask corresponding to non-tissue pixels may then be "zeroed" (i.e. assigned the lowest intensity value such as zero) thus suppressing background noise. The foreground mask comprises the pixels that have been classified as part of the foreground and are not in the background mask. The background suppression may be done without the percentile contrast stretch although it may not be as effective. Other techniques may be used to "zero-out" or suppress the background mask such as, but not limited to, thresholding, SVM, mixture models, Bayes classification, linear regression, neural networks, random forests, decision trees, and mathematical morphology, for example.

At act 206, bias field correction may be performed on each image slice based on dividing the image slice by a smoothed or filtered version of itself, which represents an approximation of the low-frequency bias field artifact (this is referred to as 2D bias field correction). An alternative approach may include dividing the entire image volume by a smoothed or filtered version of itself, which may be generated by using a three dimensional filter kernel (this is referred to as 3D bias field correction). Using the foreground mask generated in act 204, the intensity value of the most commonly occurring pixel can be found by searching for the mode of the foreground's histogram. This value may be used to fill the background of the image volume, to reduce edge effects in subsequent processing steps [23]. The resultant, bias field corrected image slice $b(x_1, x_2)$ (or $b(x_1, x_2, x_3)$ in the three dimensional case) can be defined as:

$$b(x_1, x_2) = k \cdot \frac{R(x_1, x_2)}{F(R(x_1, x_2))} \quad (1)$$

$$\text{or } b(x_1, x_2, x_3) = k \cdot \frac{R(x_1, x_2, x_3)}{F(R(x_1, x_2, x_3))}$$

where F represents some filtering function (for example, low pass filtering or a moving average filter), $R(x_1,x_2)$ or $R(x_1, x_2, x_3)$ are the noise reduced image slices (or volume) from act 204 and k is the non-zero mode of the histogram of the denoised, outlier-reduced, background suppressed image $R(x_1,x_2)$ or volume $R(x_1,x_2,x_3)$. Bias field correction may be completed with or without denoising, outlier-reduction or background suppression although performance may be affected. To suppress the border effect, the resultant image slice $b(x_1, x_2)$ or image volume $b(x_1,x_2,x_3)$ may be multiplied by the foreground mask. The filter kernel may be adjusted, to generalize across multiple patient cohorts and scanner manufacturers, regardless of hardware configurations [19]. Additionally, bias field correction may also be performed using existing algorithms, such as the N3 or N4ITK approaches [18, 22] or any other suitable method known by those skilled in the art.

Each act of denoising (i.e. act 202), image background subtraction (i.e. act 204) and bias field correction (i.e. act 206) may be referred to as preprocessing acts. In some embodiments, each of these preprocessing acts may be optional. In other embodiments, only one or more of the preprocessing acts is performed. However, for the example embodiment of the method 200 shown in FIG. 4 all of these preprocessing acts are performed.

After the preprocessing acts, the noise levels of the MR image volume are reduced. For effective intensity standardization, the histograms of image volumes from an MC dataset should have similar shape and range characteristics. For example, tissue belonging to the same tissue class from every intensity standardized image preferably occupies the same intensity intervals (i.e. the peaks of the respective histograms, if overlaid on the same plot, generally align) after standardization. The goal of the intensity standardization act is to maximally align the intensities of the same tissue classes across the histograms of MC data, while preserving the appearance of any pathologies. For example, the appearance of hyperintense objects (e.g. WML pathology) in FLAIR MRI must be preserved in order to maintain clinical utility of the images.

As described in more detail subsequently, the intensity standardization act may comprise a series of sub acts such as acts 208-212 of FIG. 4 which involve: first determining the normalized histograms of the intensities of each image volume and scaling intensity values of the image volume to utilize the full intensity range (note that this scaling can be optional in some cases); secondly, aligning landmarks of the histograms of each image volume (i.e. corresponding to grey and/or white matter in the case of brain images) to a reference standard (i.e. a reference image volume histogram); and lastly, performing a refinement or post-processing act that aligns landmarks from each image slice of a given image volume. In the case of FLAIR MR images, a FLAIR atlas [25] reference image volume histogram can be used as the reference standard to which all other image volumes are matched or standardized. In other embodiments, other reference standards such as BrainWeb (http://brainweb.bic.mni.mcgill.ca/brainweb/), MNI (http://mcgill.ca/bic/software/minc), or any other type of image volume that may be desired to match with, may be used, for example. In at least one example embodiment, the landmarks of the histograms of each image volume may be the largest peak and the refinement of aligning landmarks from each image slice of a given image volume may be to align the largest peak of each image slice histogram to the largest peak of the image volume histogram to provide peak uniformity.

At act 208, a corresponding histogram of each image volume being processed (and for the reference standard) may be generated using the intensity values of the image volume. In order for the magnitudes of the intensity counts to be similar for comparison, the histogram of the image volume may be normalized by the total number of pixels in the image volume as follows to result in a normalized histogram h(n):

$$h(n) = \sum_{i=0}^{n} \frac{v_i}{L \cdot M \cdot N} \qquad (2)$$

where n is the number of intensity bins, $L, \cdot M \cdot$ and $N$ denote the respective image dimensions, and $v_i$ is the number of pixels in the image volume with intensity i. For example, the variable $h_1$ is used herein to denote the histogram of the image volume and the variable $h_A$ is used herein to denote the histogram for the atlas.

Due to background suppression, intensity bins of the image volume histograms corresponding to low intensities may tend to be empty. To utilize the full intensity range, the first non-zero intensity value with a non-zero number of counts may be selected, and can be referred to as $\tau_f$. This first non-zero intensity value may be subtracted from the entire image volume:

$$c(x_1,x_2,x_3)=b(x_1,x_2,x_3)-(\tau_1+1) \qquad (3)$$

where $c(x_1, x_2, x_3)$ is the resultant image volume in which the intensity range of non-background pixels may start at an intensity value of zero. However, this step is optional for intensity standardization if background subtraction is not employed, or the histograms of the image volume and the reference volume start at a common point (i.e. 0).

It should be noted that normalization may be performed at this time to the image volume and the reference volume to provide a common starting point (such as an intensity level of '1') before the alignment steps used for intensity standardization occur. This is because if the image volume histogram and the reference volume histogram have different starting points, the scaling factor that is determined may be different. For example, if the cropping or zeroing of pixels described previously in act 204 is performed then there may be several zero bins of the image volume histogram that need to be shifted to have a common starting point with the reference volume histogram. If this cropping/zeroing is not done and if both the image volume and reference volume histograms have a common starting point then the initial normalization of the image volume does not need to be done in order to obtain satisfactory intensity standardization results. Accordingly, the initial normalization at act 208 can be optional in some cases.

At act 210, an image volume landmark from a digital MR image volume being processed is identified and may be aligned against a reference volume landmark of the atlas image volume (i.e. the reference image volume). In this embodiment, the largest histogram peak (i.e. mode) is used as the landmark. In neurological MRI, the largest peak in the volume histogram corresponds to the white matter (WM) tissue class in T1 and T2 MR images; however, the CSF and background noise may also have peaks in the volume histogram that may serve as landmarks. Alternatively, in FLAIR MRI, the grey matter (GM) and WM tissue classes may appear as a single peak in the histogram (noted as the GM/WM peak) and there may also be peaks for CSF and background noise. In both of these cases, one or more landmarks may be used that correspond to one or more of the WM, GM, tissue and background noise. It should be noted that in other embodiments, the algorithm may be applied to other imaging modalities, and it may be possible to have two or more landmarks depending on the type of image that being processed. For example, in the case of neurological MRI, the GM and WM peaks can be used as landmarks. Then, the landmark for alignment, when there is more than one peak in the histogram, can be determined from two or more landmarks (e.g. peaks) by finding the minimum between two peaks, the average between two peaks, or some other histogram characteristic. Different landmarks may be chosen depending on the distribution of the histogram (multimodal, unimodal), the MR modality (i.e. T1, T2, FLAIR, PD) and the region of the body being imaged (brain, heart, breast, etc.). For example, in a neurological T1 or T2 MR image, the histogram is usually bimodal with one peak corresponding to the white matter, and the other to the gray matter tissues. In accordance with the teachings herein, in another embodiment that can be used with images having bimodal histograms, the landmark may be selected to be the average point between the two peaks, the minimum, or some robust variation that uses both landmarks to define a consistent point. In another example, for imaging modalities having a trimodal histogram, it is possible to use the middle peak as the landmark, or some variant such as the median, the average, or some robust variation that defines a consistent point.

To align a landmark (e.g. a peak) of the digital MR image volume or digital image slice being processed with a corresponding landmark (e.g. a corresponding peak) of a histogram of the reference image volume or a reference image slice, the following procedure can be used which involves applying a transformation:

$$d(x)=T\{c(x)\}, x=(x_1,x_2,x_3) \qquad (4a)$$

where ($x_1$, $x_2$, $x_3$) are the spatial coordinates for an image volume and the transfer function T( ) is a general linear or nonlinear transformation function that is used to align the histograms of an MR image slice or an MR image volume with respect to an image slice reference or an image volume reference, respectively. For example, image volume alignment can be done according to equation (4b) while and image slice alignment can be done according to equation (4c).

$$d(x_1,x_2,x_3)=T\{c(x_1,x_2,x_3)\} \qquad (4b)$$

$$d(x_1,x_2)=T\{c(x_1,x_2)\} \qquad (4c)$$

Accordingly, volume refinement (which can also be called volume standardization) may be performed on intensity values of a digital MR image volume by applying a transformation function to align an image volume landmark of a volume histogram of the digital MR image volume with a reference volume landmark of a reference histogram of a reference image volume to generate a transformed digital MR image volume.

Equation 4(d) provides an example of how, in the example embodiment described herein, the transformation function T( ) can be implemented for volume alignment.

$$d(x_1, x_2, x_3) = \alpha \cdot c(x_1, x_2, x_3) \quad (4d)$$

The function $d(x_1, x_2, x_3)$ may be denoted as a scaled digital image volume that is scaled based on the intensity value of a landmark in the atlas or reference image volume, where the landmark is the peak intensity in this example embodiment, but as noted previously, other landmarks can be similarly used in which case equation (4d) is revised accordingly. Due to this contrast stretch (i.e. scaling by a factor $\alpha$), intensity bins at the upper end of the corresponding scaled image volume histogram (e.g. $d(x_1, x_2, x_3)$) may tend to be sparsely populated (e.g. some bins may contain no counts). To more fully utilize the intensity scale, all bins with counts of zero may be deleted from this scaled image volume histogram, to result in the decrementation of the upper pixel values in the image volume. In other embodiments, this deletion may not be done.

In this example embodiment, alpha is defined as the ratio of the respective intensity values between the peaks (or some other landmarks) as:

$$\alpha = \frac{A}{I} \quad (5)$$

where $\alpha$ is a multiplicative factor, referred to as the image volume scaling factor, that can be used to scale the image volume (i.e. scale the image volume histogram $h_I$ along the horizontal axis) to align a landmark (e.g. a peak) of the digital MR image volume being processed. To find the reference volume landmark used in this example embodiment, the location of the largest peak in the atlas image volume histogram, $h_A$, the intensity value with the maximum intensity count (e.g. peak of the reference image volume) can be found by using equation (6):

$$A = \operatorname*{argmax}_{n} h_A(n) \quad (6)$$

where A is the intensity value in the atlas volume that corresponds with a certain landmark, such as WM in T1 and T2, and the GM/WM peak in FLAIR MRI. The image volume landmark may be detected in a similar manner in the image volume as well, and can be denoted as I.

At act 212, the image slice landmark of each individual scaled image slice of the scaled digital image volume, may further be aligned. Accordingly, this may involve separating the transformed digital MR image volume into a plurality of digital MR image slices; and performing slice refinement for each digital MR image slice by: generating an image slice histogram; determining an image slice landmark from the image slice histogram; and generating a transformed digital MR image slice by applying a second transformation function to the image slice intensities to align the image slice landmark with the image volume landmark.

For example, in one example embodiment, the image slice landmark may be the largest peak (i.e. mode) of each individual scaled image slice of the scaled digital image volume, may further be aligned. In other embodiments, as described above, another feature may be selected as the landmark. In some cases, although the histogram of the image volume may be aligned with the reference image volume histogram in respect of the largest peak, the corresponding peaks of individual scaled image slices within the image volume may not be aligned to this central peak. The discrepancy may be due to inhomogeneity in the Z-direction during image acquisition and other artifacts. Using only a smoothing or filtering approach to address this inhomogeneity may not be effective because the spacing between each scaled image slice may be too large leading to low resolution in the Z-direction. Instead, a post-processing or refinement step may be carried out in act 212 to align the histogram peaks of all scaled image slices to the image volume peak, which is outlined herein.

To carry out post-processing, histograms of individual scaled image slices can be aligned with the overall image volume histogram by taking the difference between the image volume landmark and the image slice landmark in each scaled image slice histogram, and shifting the image slice intensity values by an image slice shifting factor to align with the image volume histogram landmark and produce scaled and shifted image slices.

For example, the intensity value of the image volume landmark, which is the main peak in this example embodiment, can be denoted by V, and the intensity value of the largest peak of each scaled image slice (i.e. the image slice landmarks) can be denoted as S. As such, for each scaled image slice, a difference value $\beta$ between the intensity values of the global volume peak V and the scaled image slice peak S (or any other histogram landmarks depending on the features of interest for the underlying images) may be defined as shown in equation (7a) and the histogram shifting can be done according to equation (7b).

$$d(x_1, x_2) = c(x_1, x_2) - \beta \quad (7b)$$

The value $\beta$ is the image slice shifting factor and it may be added to the pixel values for the corresponding image slice. The addition of a particular $\beta$, as determined herein, to each corresponding scaled image slice may be carried out to align the peak in the individual image slices to the global peak of the image volume and generate scaled and shifted image slices. Any intensity values of voxels of the shifted and scaled image slices falling below zero, as a result of adding $\beta$ (e.g. where the value of $\beta$ is negative), may be set to zero. In other embodiments, if other landmarks are used instead of the mode, the image slice to image volume alignment can be carried out in the same way with the values of V and S being determined differently depending on how the other landmarks are combined such as, but not limited to, an average of the landmarks, a median of the landmarks, a minimum between the landmarks (if they are peaks), a maximum between the landmarks (if they are valleys), for example.

Alternatively, in another example embodiment in accordance with the teachings herein, this image slice refinement can be completed by scaling the image slice histogram according to equations (7c) and (7d):

$$d(x_1, x_2) = \gamma \cdot c(x_1, x_2) \quad (7c)$$

$$\gamma = \frac{A}{J} \quad (7d)$$

where J is the intensity of the image slice landmark, and A is the intensity of the reference landmark. For example, when image slice histograms are compared to the image volume histogram the image volume histogram acts as the atlas and provides the atlas landmark. This approach does not require zeroing out any intensities after the shifting since none of the shifted values in the image slice histogram are lower than zero. However, in other embodiments, the reference landmark may be an atlas volume landmark from a histogram of an atlas volume, an image landmark from a histogram of one of the image slices from the image volume, or a histogram of an image slice from a different image volume.

To detect image slice landmarks, a kernel smoothing function can be applied to each image slice histogram to improve peak detection since in some cases multiple peaks can be detected. For example, a kernel width of 8-10% of the highest image intensity may be used, to allow for the detection of the histogram peak in each of the individual scaled image slice histograms. For the main example embodiment described herein, the application of this kernel smoothing function is optional. It should be noted that other methods for detecting the image slice landmarks may be used.

In some embodiments, another option is to identify whether a peak in a histogram belongs to a corresponding tissue class, which may include performing a search within a preferred intensity interval. For example, in neurological studies, the preferred or predetermined intensity range may be selected to correspond to the boundaries of the brain class (e.g. at least one of WM and GM tissues depending on the imaging modality) in the atlas image volume, to which all image volumes are aligned. For example, in FLAIR MR imaging, the predetermined intensity range can be selected to correspond to intensity values for GM tissue and/or WM tissue whereas for other imaging modalities, the predetermined intensity range can be selected to be intensities corresponding to at least one of GM tissue, WM tissue, cerebrospinal fluid (CSF), background noise and some combination of GM tissue, WM tissue, CSF and background noise. As another example, in some cases, if the brain tissue class is known to fall within a predefined intensity range that is +/−1 standard deviation from the landmark, or +/−2 standard deviations from the landmark or +/−3 standard deviations from the landmark, then a search of $h_s$ for a peak may be performed within this range. Alternatively, the search limits (which can generally be referred to as R1 to R2) may be manually defined and they generally do not vary across datasets as a result of the intensity standardization performed previously in acts 208 and 210. In instances, where no peak is found then that may imply that there are no features in the image slice in the search range that correspond to the features being searched and to the image slice. Further, this range merely represents a search interval, which does not impact final results.

At act 214, the intensity standardized image volume may be registered to the image atlas volume to spatially align the former to the latter. Registration may be accomplished using affine registration or other image registration techniques such as non-rigid registration, as is known by those skilled in the art [26, 27]. It may be noted that the affine registration of intensity standardized images may provide more consistent registration results compared to aligning non-standardized image volumes on the basis that the value of tissue intensities become more consistent between image volumes. This act may be optional in some cases.

It should be noted that the image standardization described herein can be performed in real-time. Furthermore, in some embodiments, the image standardization described herein can be applied to MR images of other anatomies, with a unimodal or a multimodal intensity distribution, that were obtained using a given type of MR imaging as explained earlier.

Validation Metrics for Evaluating Image Standardization Performance

To determine suitable values for the parameters of the standardization framework, and to assess the performance of the standardization framework in respect of reducing image variability in a given data set, validation metrics may be defined and then determined for various test cases. This section discusses the validation of the standardization framework acts, as well as the validation of the overall standardization framework, in the form of investigating the effects of standardization on image segmentation algorithms.

In respect of denoising and bias field correction, there are some parameters, such as filter type and filter size, that can be adjusted to improve certain image features, such as image sharpness, for example, as is known by those skilled in the art.

Validation of Intensity Standardization

In respect of intensity standardization (e.g. acts 208-212 of FIG. 4), it is noted previously that the histograms of intensity standardized image volumes are similar, meaning that the image intensities of the each of the standardized image volumes are also similar to the atlas image volume that was used as the reference standard. To measure the similarity between the standardized image volumes, the histogram of a given standardized image volume may be determined, and denoted as $H_I$, and the histogram of the atlas image volume can be determined and denoted as $H_A$. The correlation coefficient, which may be used to quantify the level of similarity, between the respective histograms of each of the standardized image volumes and the atlas image volume can be determined as [28]:

$$C(H_I, H_A) = \frac{cov(H_I, H_A)}{\sigma_{H_I} \sigma_{H_A}} \qquad (8)$$

where cov is the covariance of $H_I$ and $H_A$, and $\sigma_{H_I}$, $\sigma_{H_A}$ are standard deviations of the histograms of the standardized image volume and the atlas image volume, respectively, where "I" represents the given image volume being processed and A represents the reference image volume.

The Root Mean Squared Error (RMSE), denoted as D, may be used to compute the difference between the histograms of each image volume and the mean histogram of all of the image volumes as follows:

$$D = \frac{1}{M} \sum_{k=1}^{M} \sqrt{\sum_i |h_k(i) - h_{mean}|^2} \qquad (9)$$

where M is the number of subjects imaged, $h_k$ is the intensity histogram for the $k^{th}$ image volume for the $k^{th}$ subject and $h_{mean}$ is the average image volume histogram across all subjects.

An independent samples t-test may be conducted to analyze significant changes to the correlation coefficient and RMSE before and following intensity standardization. An improvement in these metrics may imply better alignment of intensity intervals, yielding more consistency between tissue intensities in different images.

As noted previously, preservation of pathology (i.e. maintaining the appearance of WML for the application of neurological FLAIR MRI) after intensity standardization is preferred. As an example, to measure whether the appearance of WML are maintained after intensity standardization, image contrast between WML and the surrounding tissues can be measured and compared before and after intensity standardization. This analysis may be useful, as a reduction in image contrast between WML and surrounding brain tissues after intensity standardization may reduce the ability of a human or an algorithm to detect WML from MR brain images, which is not desirable. To measure contrast, an example WML segmentation scheme was applied to first detect one lesion per subject and local contrast metrics were computed from the lesion before and after intensity standardization. These processes are described in more detail below. It should be noted that this segmentation scheme is used for evaluation purposes and is not meant to limit the scope of the Applicant's teachings herein.

The standardized images may be further processed to separate between tissues; i.e. brain matter and pathology, in accordance with the teachings herein, by implementing a simple, threshold-based segmentation algorithm. As the intensities of standardized images fall within a standardized intensity scale, the intensity ranges of tissues and pathology may be similar across all images, making thresholding a viable option for easier and more efficient image segmentation. For example, an intensity threshold known to be greater than the intensity of GM/WM in the atlas image volume may be applied to the standardized brain-extracted image volumes to segment hyperintense pathology (e.g. WML). That is, image intensity values below the threshold may be assigned a value of zero. In some embodiments, a threshold of 400, for example, may be chosen for a particular atlas image based on visual or automatic analysis of image volumes. The thresholded image with other tissues "zeroed out", may leave an approximate segmentation mask corresponding to the remaining WML. With this WML mask, the largest lesion may be kept, and the image slice of the image volume containing the majority of this largest lesion can be selected for ease of computation. The long axis of the lesion can be measured, and lesions less than 3 mm in diameter may be excluded [29]. With these lesion masks, the local contrast can be computed [30, 31] as follows:

$$c(x, y) = \left| \frac{\mu_O - \mu_N}{\mu_O + \mu_N} \right| \quad (10)$$

where $\mu_O$ is the mean intensity value of the pixels of the lesion, and $\mu_N$ is the mean intensity value of the pixels of the surrounding tissues. The original lesion mask can be subtracted from a dilated lesion mask, to yield the neighborhood region of the GM/WM around the WML. Each lesion mask may be dilated with a disk having a desired disk size. For example, a disk size of fifteen may be used. Alternatively, a disk size of from about 5 to 20 may be used. An increase in local contrast may indicate that the boundaries of the WML have been preserved, yielding edges that can allow for discrimination between WML and GM/WM tissue classes. T-tests can be performed to compare local contrast measurements (see equation 10) before and after image standardization to identify statistically significant improvement in tissue discrimination following image standardization.

Any improvement of the metrics can be quantified using a change in percentage of the respective metric following standardization as follows:

$$\% \text{ Change} = \frac{\text{metric}_S - \text{metric}_O}{\text{metric}_O} \times 100\% \quad (11)$$

where $\text{metric}_O$ and $\text{metric}_S$ represent the metrics from the original and standardized image data, respectively. This may be applied to the correlation coefficient, the RMSE, and the local contrast measures, and possibly other performance measurements to detect improvement of image quality after standardization.

Validating WML Segmentation on Intensity Standardized FLAIR MRI

To evaluate the intensity standardization framework (e.g. as indicated in method 200 of FIG. 4) and to verify whether this intensity standardization framework is an effective pre-processing step for subsequent image processing algorithms (e.g. algorithms for image segmentation or object detection), a WML segmentation algorithm [17, 35, 36] can be applied to both original and standardized image data to determine whether WML can be preserved following intensity standardization and to determine whether standardized images can be segmented more accurately compared to non-standardized images. Modeling PVA is generally regarded as an important step for WML segmentation, as it may allow for more accurate measurement of sub-voxel volume. To determine whether intensity standardization improves the performance of PVA-based approaches, the WML segmentation result can be quantitatively measured for both original and standardized image data.

The WML segmentation algorithm can be used to quantify PVA in an image, using an edge map defined as $\alpha'(y)$, which represents the normalized edge strength a' as a function of intensity y. The edge map is used to estimate a partial volume fraction (PVF) for each tissue class (e.g. CSF, WM/GM and WML tissue classes). Binary masks can be created by thresholding the class memberships at a value of 0 (which retains all pixels containing WML). Denoising (i.e. smoothing), using a bilateral filter [17, 36] or multiscale denoising [35], can be applied initially. However, the smoothing procedure can be left out to allow for a raw comparison between the standardized and original image data, without denoising playing a role. A false positive reduction scheme can also implemented to remove CSF flow-through that can occur along the brain midline by identifying WML within the brain ventricles and excluding them.

Several metrics can be employed to quantify the effects of intensity standardization on WML segmentation. The edge map $\alpha'$ (y), which quantifies edge information as a function of intensity in the images and is used for generating the final segmentation results, may be examined. Ideally, for robust and reliable segmentations, the edge map should appear nearly identical and should be aligned for all subjects. This similarity may be measured by the RMSE (see equation 9). A decrease in this metric after image standardization may indicate better alignment of the edge maps.

WML segmentation accuracy can be quantified by measuring the overlap and volume agreement between automatically generated segmentations and manual ground-truth masks made by experts by manually outlining structures using a stylus or mouse, along with computer software. Overlap may be computed using the Dice Similarity Coefficient (DSC) metric [32]), where the segmentation masks generated from the original and standardized image data can used separately and their respective DSC values may be compared. The DSC can be defined as:

$$DSC = \frac{2|A \cap B|}{|A| + |B|} \quad (12)$$

where A is the binary mask of the atlas image volume, and B is the binary mask of the test image volume.

If the segmentation accuracy of the standardized image data is equal to or greater than that of the original image data, it can be assumed that all lesion boundaries were adequately preserved and/or enhanced since segmentation accuracy is higher. To measure this, the change in DSC, $\Delta$DSC, may be determined using equation 12. To analyze volume agreement, a plot of the ground-truth lesion load volume versus the segmented volumes can be made. A "perfect" automated segmentation yields a line at equality in such a plot since the automated algorithm measured the same volumes as the manual segmentation. The slope may be computed separately for both the standardized and original image data, and compared. A slope coefficient closer to one may indicate better agreement of the automated segmentations with the manual ground-truth segmentation.

Validation of Resolution and Patient Orientation Normalization

In respect of evaluating resolution and patient (i.e. subject) orientation normalization, two tests may be used to assess image registration accuracy. The Dice Similarity Coefficient (DSC) can be used to measure the amount of overlap between the binary masks of each image and the atlas, before and after image standardization, as defined in Equation 12.

To validate whether image registration successfully accounted for patient rotation in the transverse plane, the patient head angles before and after image standardization can be compared. To compute the patient head angle, the center of gravity (CoG) of the volume can be first determined. Thereafter, the furthest most non-zero point from the CoG can also be determined. This point usually corresponds with the tip of the nose, and allows for the calculation of the long axis of the head in the transverse plane. The x, y coordinates of the CoG may thus be denoted as $X_{COG}, Y_{COG}$, and the coordinates of the end of the long axis may be denoted as $X_{LA}, Y_{LA}$. The angle $\theta$, which may be used to represent the deviation of the patient from a position corresponding to perfect alignment with the sagittal plane, can be defined as shown in equation 13.

$$\theta = \cos^{-1} \frac{X_{COG} \cdot X_{LA} + Y_{COG} \cdot Y_{LA}}{\sqrt{X_{COG}^2 + Y_{COG}^2} \cdot \sqrt{X_{LA}^2 + Y_{LA}^2}} \quad (13)$$

Independent sample t-tests can be used to determine whether the image registration algorithm increased overlap and normalized patient orientation following image registration. An increase in overlap after image standardization (i.e. including image registration/spatial standardization) may indicate that there is greater consistency in the location of tissues in space, making positional features more relevant in further analysis.

Image Data Set for Standardization and Analysis

A FLAIR template image volume atlas [25], acquired on a Siemens 3T MR scanner, with 0.7 mm³ resolution was used for image standardization, created from images of subjects with WML present.

TABLE 1

A summary of data used to validate the image standardization framework.

|  | DB1 | DB2 | DB3 |
| --- | --- | --- | --- |
| Disease | Vascular | Dementia | Vascular |
| Total Image Volumes | 500 | 3500 | 27 |
| Total Image Slices | 24,000 | 120,000 | 945 |
| Centres | 9 | 58 | 1 |
| Scanner Vendors | MR1, MR2, MR3 | MR1, MR2, MR3 | MR4 |
| Magnetic Field Strength | 3 T | 3 T | 1.5 T |
| TR (ms) | 8,000-11,000 | 650-11,900 | 8,000 |
| TE (ms) | 117-150 | 20-193 | 128 |
| TI (ms) | 2200-2800 | 200-2800 | 2000 |
| Pixel Spacing (mm) | 0.4286-1 | 0.7813-1.0156 | 0.5 |
| Slice Thickness (mm) | 3 | 5 | 6 |

A summary of FLAIR MRI data used to validate the image standardization framework can be found in Table 1. The DB1 dataset contains data from 250 ischemic disease subjects with varying numbers of follow-up scans, yielding a total of 500 image volumes. Images were acquired on MR scanners from three manufacturers using a magnetic field strength of 3T: MR1, MR2 and MR3 or 1.5T: MR4. A breakdown of the data by scanner vendor is shown in Table 2. The images from DB1 and DB3 were acquired at several different acquisition parameter settings and contain the same disease classification; thereby providing a good representation of variability in MC studies. As a result, DB1 and DB3 are used to validate many aspects of the image standardization framework (intensity standardization, resolution normalization, contrast preservation of WML, orientation normalization, etc.). For contrast analysis based on WML, lesions with a diameter greater than 3 mm were included, resulting in 441 images acquired at 3T (DB1), and all 27 volumes at 1.5T (DB3) for contrast analyses. Additionally, WML ground-truth masks were available in five volumes from the DB1 dataset and were used to validate WML segmentation before and after standardization. These masks were available for image data generated by the MR2 scanner. For validation of spatial resolution and patient orientation, DB1 was used.

TABLE 2

Breakdown of the DB1 database by scanner vendor

|  | MR1 | MR3 | MR2 |
| --- | --- | --- | --- |
| Total Image Volumes | 135 | 165 | 200 |
| Total Image Slices | 6,480 | 7,920 | 9,600 |
| Centres | 3 | 3 | 6 |
| Magnetic Field Strength | 3 T | 3 T | 3 T |
| TR (ms) | 8,000-9,995 | 9,000-11,000 | 9,000 |
| TE (ms) | 141-150 | 125 | 117-122 |
| TI (ms) | 2,200-2,390 | 2,800 | 2,500 |
| Pixel Spacing (mm) | 0.8594-0.9375 | 0.4268 | 1 |
| Slice Thickness (mm) | 3 | 3-6 | 3 |

Results of Image Processing Under the Standardization Framework

The study involved analyzing the effects of MRI acquisition parameters on FLAIR images, and demonstrating that effective image standardization can simplify segmentation algorithms and improve accuracy while maintaining the appearance of WML.

FIGS. 5A-5H show representative images of the standardization framework applied on images acquired using different MR scanners that are represented by generic identifiers MR1, MR2, MR3 and MR4. Note that MR1 and MR4 are the same vendor, but differ by the magnetic field strength of the main magnet (MR1 is 3T and MR4 is 1.5T). MR1, MR2 and MR3 are from DB1 and MR4 is from DB3. The figures in the left column correspond to the original images obtained from these MR scanners, and the images in the right corresponds to the same image processed under the image standardization framework. The darkness of the skull in some of the images can be attributed to different acquisition protocols, and did not affect the standardization of the GM/WM intensities.

Figure 6A:
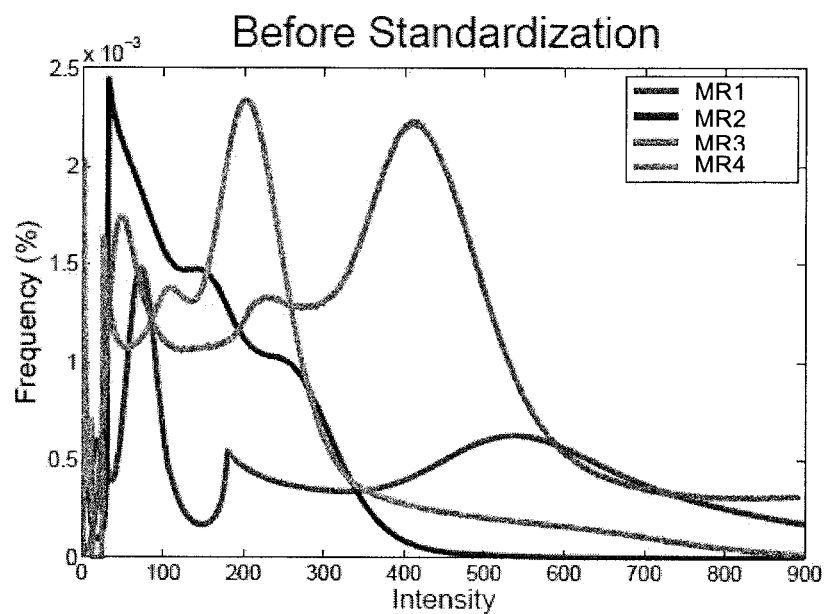
FIG. 6A-6B show the average volume histograms for four different vendors together before and after processing using the intensity standardization method of FIG. 4.
Figure 6B:
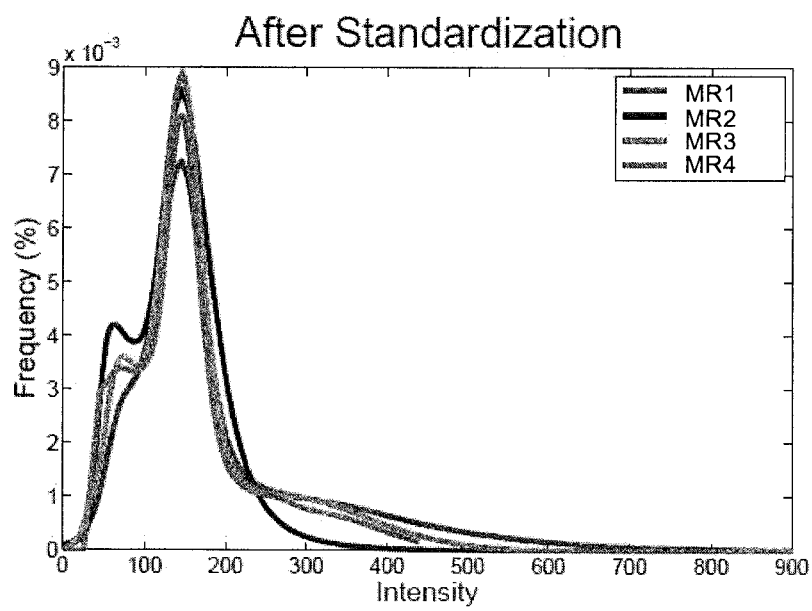

Resultant histograms of every image volume of different patients acquired using the MR scanners before and after intensity standardization are shown in FIGS. 1A-1H. These figures show that within a given database, there is a range of intra- and inter-scanner variability, as shown in the histograms of the original images. However, the histograms (on the right side) also indicate that image standardization can reduce this variability, increasing the likelihood that analysis of these standardized images can be automated. The average histograms from each scanner before (top) and after standardization (bottom) are shown in FIGS. 6A-6B.

Denoising and Bias Field Correction: As noted previously, a median filter can be used for denoising (e.g. act 202 of FIG. 4) and the filter kernel can be determined to provide a good trade-off between smoothing and preservation of WML edges. For example, the width of the median filter, in the case of the image set considered, can be set to 0.8% of the minimum image dimension in the x,y direction. For example, an image with a size of 560×560 may have a filter width of five pixels. To reduce the low frequency variation artifact from bias field, the point spread function of the LPF having the lowest Coefficient of Variation (CoV) can be used. The standard deviation of the kernel, $\sigma$, can be set to 8% of the minimum image dimension, and the kernel width can be set to $3\sigma$ using the CoV [19]. For other image sets, other parameter values may be used as is known by those skilled in the art.

Figures 7A, 7B:
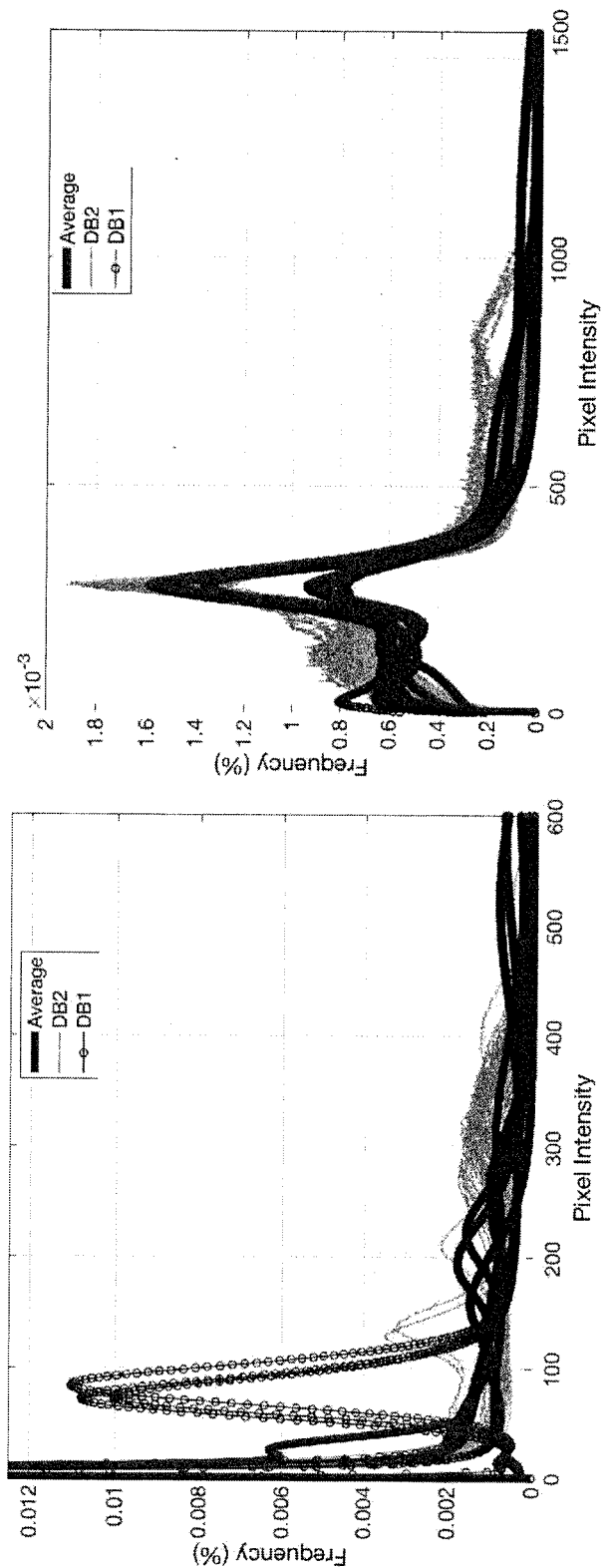
FIGS. 7A-7B show the average histograms from each centre from DB1 and DB2 databases (representing a total of 67 centres), before and after intensity standardization using the standardization method of FIG. 4.

Intensity Standardization:

FIGS. 7A-7B show the average histograms from each centre in DB1 and DB2 studies (a total of 67 centres), before and after intensity standardization. A solid line represents the 9 centres from DB1, the solid line with circles represents the 58 centres from DB2, and the thick black line is the average histogram from both studies. In FIG. 7A, it can be seen that there is significant variability between the histograms of images acquired at different centres. The locations of the central peaks and ranges are variable between centres, highlighting the lack of a standard intensity scale. However, FIG. 7B shows the histograms following intensity standardization; the peaks of the histograms are now aligned, and the peaks corresponding to the GM/WM class are more prominent in all images. These results clearly demonstrate the utility of intensity standardization: not only are the intensities associated with different tissues now identical between images, but image properties, such as contrast, are normalized as well.

To quantitatively assess whether the intensity standardization method described herein normalizes the histograms of the images and aligns the intensities of similar tissues into the same intensity range, regardless of MR scanner vendor or acquisition parameters, three metrics were measured for DB1 and DB3. Specifically, to quantify similarity between volume histograms and the volume atlas, the correlation coefficient was used, whereas the RMSE was used to measure similarity of all of the image volume histograms to the population mean histogram. The local contrast was also computed to examine the contrast between WML and brain matter. These three metrics were computed before and after intensity standardization. An improvement in these metrics following intensity standardization, as shown by t-tests, may indicate an increased similarity in image characteristics. Table 3 summarizes the results of these tests, which show a statistically significant improvement in correlation and RMSE for each MR scanner vendor. Local contrast has also been improved significantly in all 3T scanners (MR1-3), but not in MR4, which is a 1.5T scanner. Although the contrast result was insignificant for MR4, the local contrast was still maintained, which indicates pathology preservation (i.e. the WML were not suppressed due to intensity standardization).

TABLE 3

Summary of intensity standardization metrics on DB1 and DB3 for t-tests: correlation, RMSE, and local contrast.

| | Before Standardization | After Standardization | T-Test Results |
|---|---|---|---|
| Histogram Correlation | | | |
| MR4 | 0.040 ± 0.013 | 0.855 ± 0.073 | t(52) = −62.81, p < 0.001* |
| MR1 | 0.192 ± 0.041 | 0.735 ± 0.190 | t(360) = −182.8, p < 0.001* |
| MR3 | 0.033 ± 0.028 | 0.820 ± 0.025 | t(458) = −37.05, p < 0.001* |
| MR2 | 0.033 ± 0.019 | 0.786 ± 0.068 | t(576) = −321.5, p < 0.001* |
| Average Result | 0.070 ± 0.078 | 0.787 ± 0.112 | t(1452) = −141.9, p < 0.001* |
| Histogram RMSE | | | |
| MR4 | 18860 ± 4328 | 0.402 ± 0.156 | t(52) = 15.89, p < 0.001* |
| MR1 | 29978 ± 271 | 1.58 ± 0.0004 | t(360) = 1484, p < 0.001* |
| MR3 | 46475 ± 11590 | 1.58 ± 0.0001 | t(458) = 60.8, p < 0.001* |
| MR2 | 18951 ± 5186 | 1.58 ± 0.0001 | t(576) = 62.1, p < 0.001* |
| Average Result | 2974 ± 1484 | 1.52 ± 0.2937 | t(1450) = 54.0, p < 0.001* |
| Local Contrast | | | |
| MR4 | 0.289 ± 0.06 | 0.300 ± 0.068 | t(52) = −1.1028, p = 0.2752 |
| MR1 | 0.378 ± 0.128 | 0.446 ± 0.118 | t(352) = −5.23, p < 0.001* |
| MR3 | 0.376 ± 0.146 | 0.423 ± 0.148 | t(458) = −3.45, p < 0.001* |
| MR2 | 0.399 ± 0.171 | 0.449 ± 0.017 | t(498) = −3.32, p < 0.001* |
| Average Result | 0.379 ± 0.146 | 0.431 ± 0.146 | t(934) = −5.439, p < 0.001* |

*indicates that results are at significance.

FIGS. 8A-8F show the visual results of the intensity standardization on MR image volumes with varying WML lesion loads, for different MR scanner vendors. All images were acquired using a magnetic field intensity of 3T.

Figure 8A:
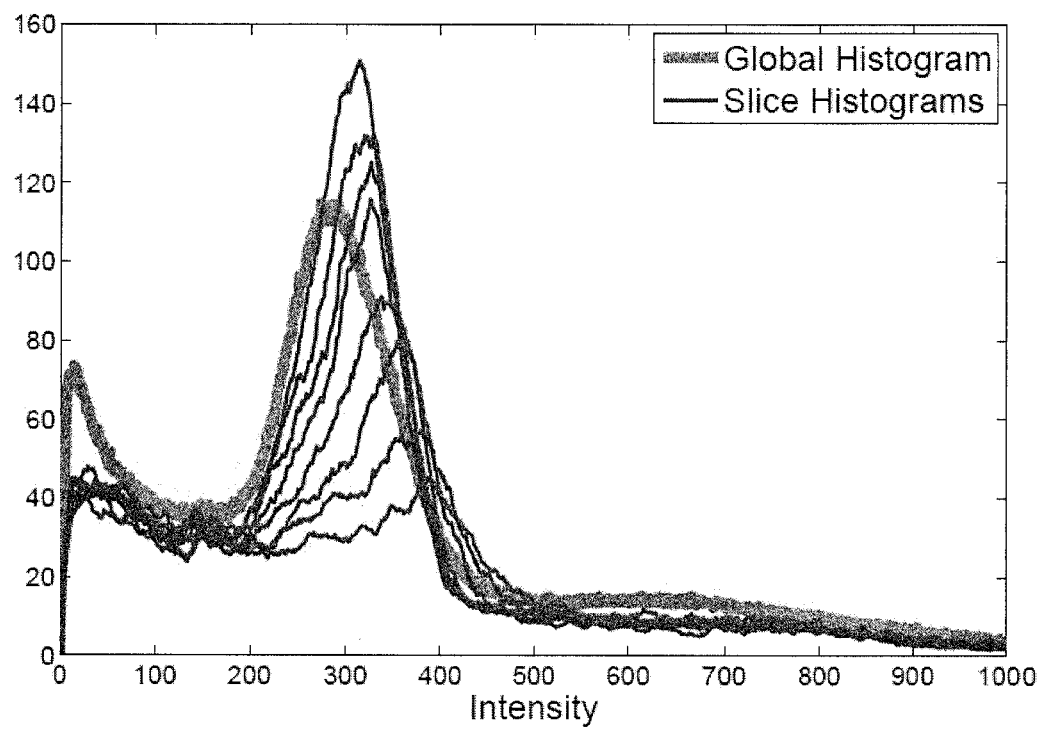
FIGS. 8A-8B show histograms of image slices of an image volume before and after peak alignment, respectively, in accordance with the teachings herein.
Figure 8B:
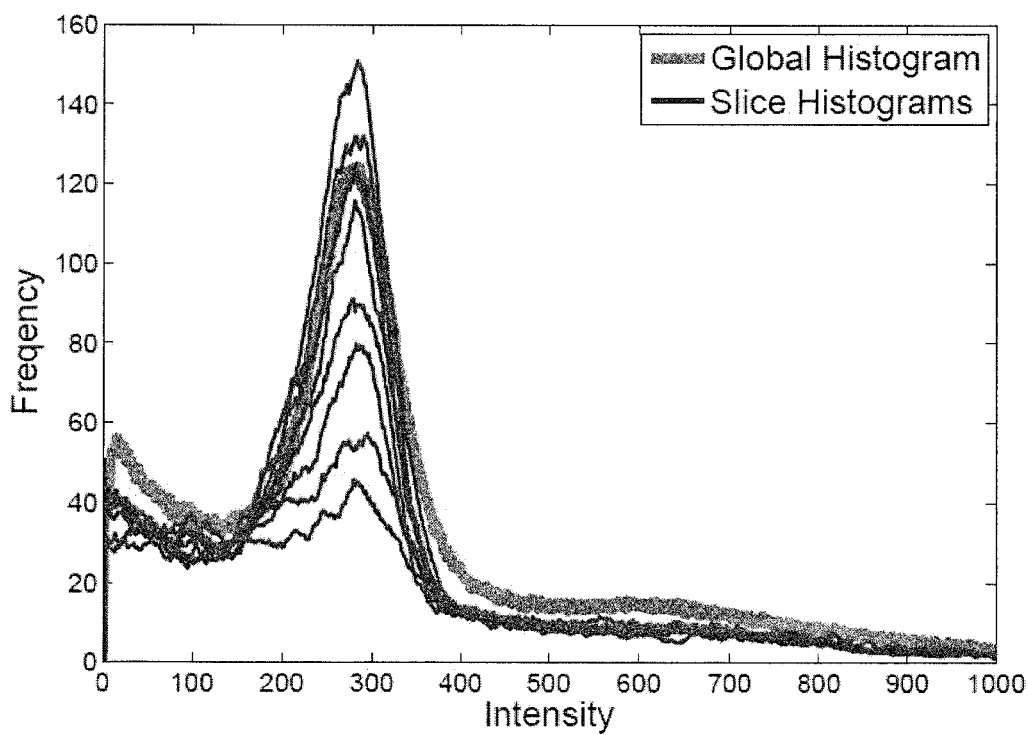

FIGS. 8A-8B shows how the refinement stage of the intensity standardization processing (e.g. refinement in act 212 of FIG. 4) can be used to correct intensity non-uniformity in the Z-direction by making the mean intensities of GM/WM consistent over every image slice within an image volume. Specifically, FIG. 8A shows the image volume histogram and the individual image slice histograms for a single patient prior to intensity standardization. The observable peaks of the image slice histograms are not aligned throughout the entire image volume, indicating that the mean intensity of the brain region varies throughout the entire image volume. FIG. 8B shows the histograms following intensity standardization and in particular the refinement in act 212 of FIG. 4 in which the peaks in the histograms from individual image slices become aligned. The overall effect of this correction yields a more peaked image volume histogram, therefore reducing variability in the intensity range occupied by this tissue class, yielding better definition over the whole image volume. For cases where pixels were shifted to have an intensity below zero and were eventually zeroed out, additional analysis indicates that the zeroing results in a loss of less than 5% of the pixels in the entire image volume, belonging to low intensity, non-brain tissues, and did not affect intensity standardization or image segmentation results. Accordingly, this refinement step may improve the effectiveness of other image processing algorithms that may be used for further analysis, as the intensity of the brain becomes more uniform throughout the entire volume after intensity standardization.

Figure 9A:
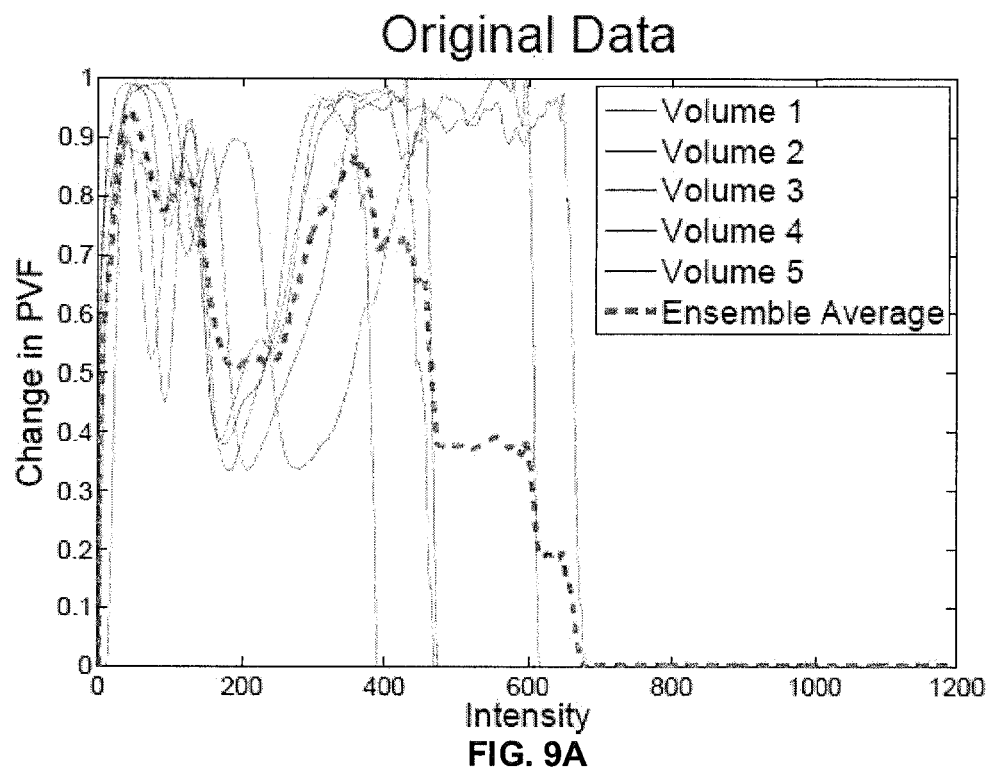
FIGS. 9A-9B show global edge gradient maps of image volumes before and after processing using the standardization method of FIG. 4.
Figure 9B:
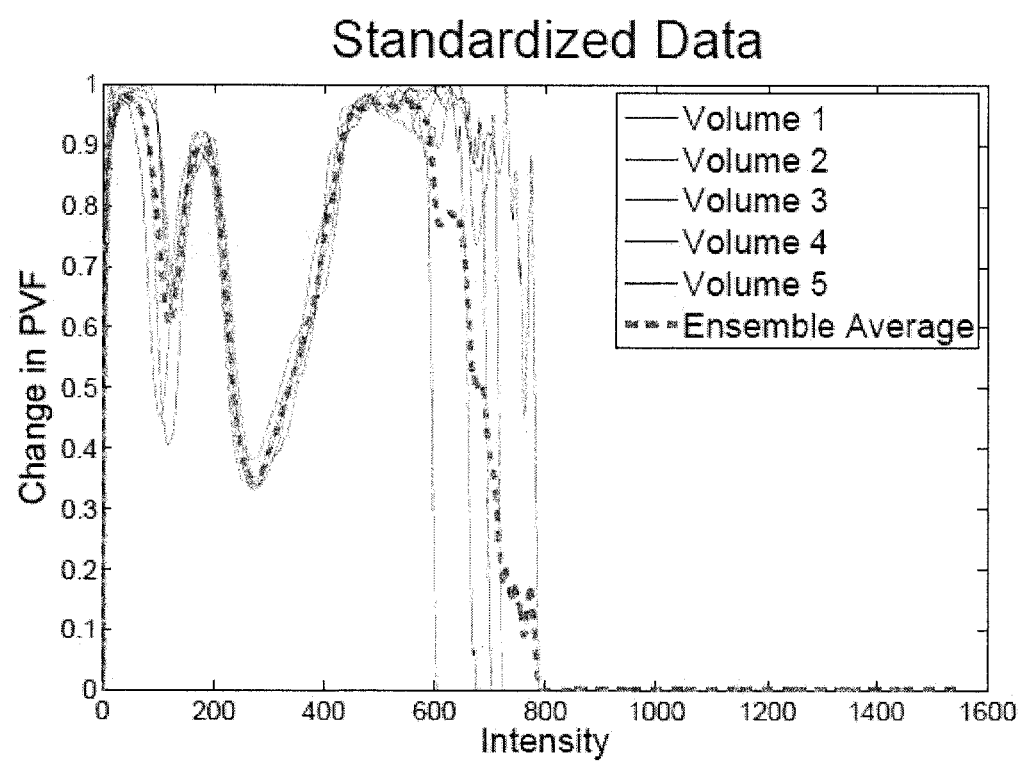

To demonstrate how intensity standardization improves downstream processing, a WML segmentation algorithm described previously was performed on five volumes from the DB1 dataset for which ground-truth delineations are available. Both the alignment of the edge maps α'(i) and the image segmentation performance were examined before and after intensity standardization. In FIGS. 9A-9B, the edge maps for all image volumes were compared with the ensemble average for both original (FIG. 9A) and intensity standardized image data (FIG. 9B). The edge maps of the intensity standardized image data were more consistent, and yielded a lower RMSE when compared to the original data (26.8 versus 59.2).

Figure 10A:
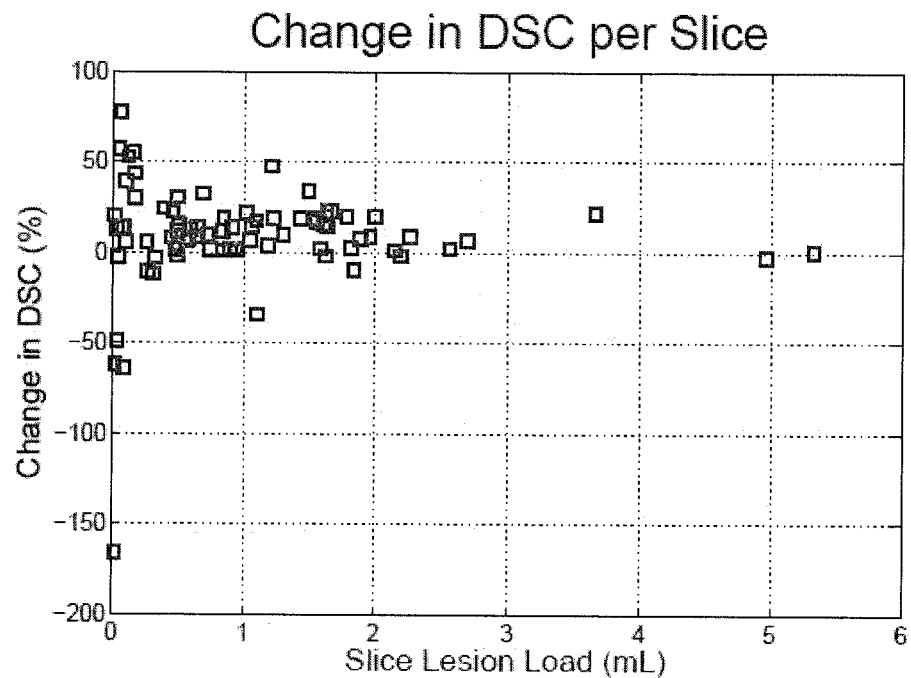
FIGS. 10A-10B show changes in Dice Similarity Coefficients for automatically segmented lesions and manually segmented lesions before and after processing using the standardization method of FIG. 4.
Figure 10B:
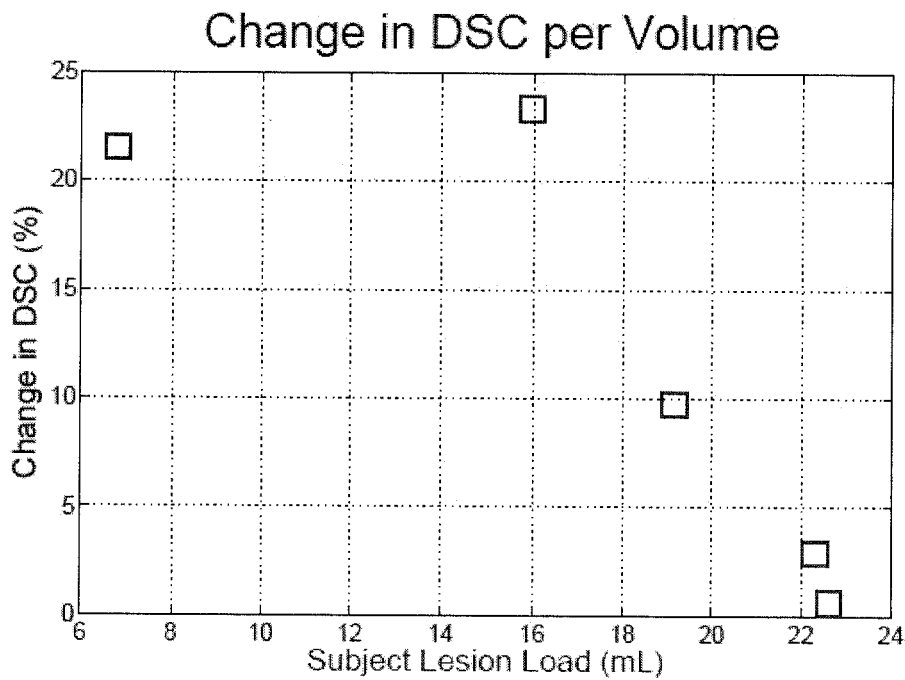
Figure 11A:
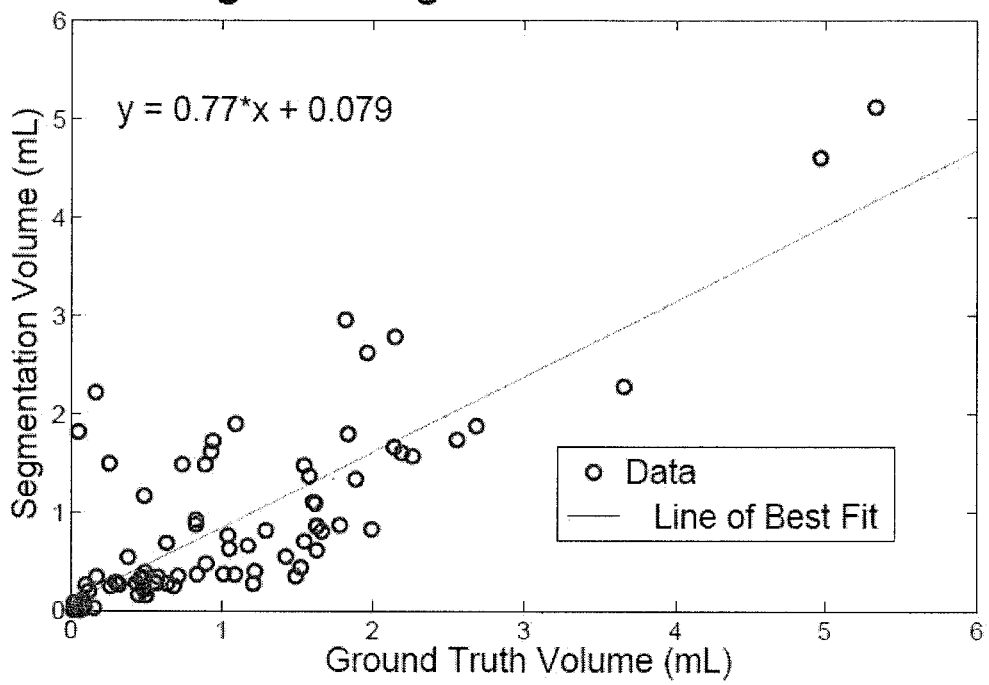
FIGS. 11A-11B show regression charts of automatically segmented lesions and manually segmented lesions before and after processing using the standardization method of FIG. 4.
Figure 11B:
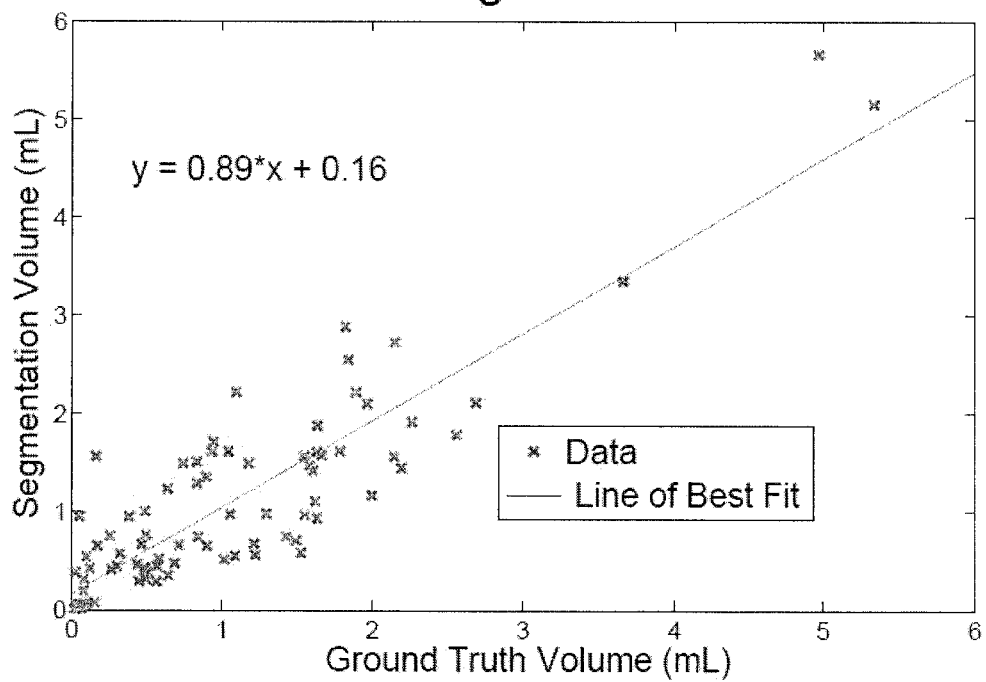

FIGS. 10A-10B show the change in DSC for WML segmentation, and demonstrates that intensity standardized image data can yield a higher DSC across all lesion loads. This shows an improvement of 87% across individual image slices. It also yields an average 11.6% improvement in DSC (S.D.=10.4) across all five image volumes. In the 82 images from the five image volumes, the mean DSC for WML segmentation of original image data was 50.68±20.31, compared to intensity standardized image data, which was 57.03±21.1. This difference can be used to demonstrate that the WML segmentation algorithm can be made more accurate and robust using intensity standardized image data. The segmented lesion loads can be compared to the manual lesion loads as indicated in FIGS. 11A-11B, which show that the segmentation of the intensity standardized image data yields a line of best fit that is closer to the line of equality, meaning that it resulted in a better image segmentation compared to the original data. Therefore, the image standardization framework in accordance with the teachings herein increased WML segmentation accuracy.

Resolution and Orientation Normalization:

The DSC can be used to measure the degree of spatial overlap of image volumes with the atlas image volume, and the head angle can be calculated to measure the deviation of the brain midline from the sagittal plane. Table 4 summarizes the change in DSC and head angle before and after image standardization (i.e. act 214 is applied). Specifically, there is a statistically significant increase in the DSC and statistically significant reduction in the mean angle following image standardization, indicating that the registration step is capable of normalizing a degree of patient rotation, and increasing overlap with the atlas, to demonstrate alignment of all images. The results suggest that following image standardization, the brains in the MR image volumes of each subject may be centered with respect to each other, thus increasing the relevance of position-based features for further analysis or processing (e.g. feature extraction and image segmentation; see the brain segmentation method described later).

TABLE 4

Overlap DSC and Patient Head Angle Before and After Standardization on DB1.

| | Before Standardization | After Standardization | T-Test Results |
|---|---|---|---|
| Dice Similarity Coefficient | | | |
| DB1 | 66.64 ± 18.0 | 81.1 ± 24.6 | t(1398) = −12.4956, p < 0.0001* |
| Head Angle (Degrees) | | | |
| DB1 | 2.7625 ± 7.9072 | 1.9819 ± 1.8533 | t(1398) = −2.5433, p = 0.0111* |

*indicates results are statistically significant

Discussion of the Standardization Results

The above results highlight an important issue for the large scale analysis of any MRI dataset, as small differences in acquisition parameters can create significant variability in image properties within a MC database. The results also show that standardizing MR images in accordance with the teachings herein allows algorithms used for further analysis of these standardized images to be made more robust and more accurate. Furthermore, although the study was conducted on FLAIR MRI with WML, the teachings herein can be applied to all MRI datasets. This image standardization framework now permits for the consistent and robust processing of large populations of subjects. For example, in contrast to other works that use piece-wise linear transformations to align histogram landmarks [14], the standardization methodology presented herein allows the histogram bounds to change without restriction, which advantageously results in maintaining the appearance of pathology and WML. Accordingly, with standardized image data, measurements derived from FLAIR MRI can be correlated with patient outcomes to gain valuable insight into neurodegenerative disease pathology.

The experimental results also showed that the median filter may be used to suppress noise in the spatial domain, as such a filter can provide a desirable balance of smoothing and edge preservation. Other filters used for noise suppression can also be used, such as the LPF and bilateral filter. However, the LPF can create blurring along tissue edges. Advantageously, a bilateral filter can be used to address the deficiencies of the LPF, because the bilateral filter can provide relatively smooth images with sharp edges. However, the edges belonging to small WML may not be detected by the range kernel, and may result in being smoothed to appear as GM/WM (i.e. meaning Grey Matter or White Matter). The median filter was found to provide the desirable trade-offs of smoothing and WML edge preservation.

Advantageously, the standardization framework of the present disclosure addresses deficiencies with conventional image processing methods, and is capable of reflecting the histogram characteristics of neurological FLAIR MRI. As shown previously, the histogram correlation between the atlas and the standardized images can be increased, while decreasing the RMSE, indicating that the intensities of tissues becomes more consistent when intensity standardization is used. These metrics can be improved for images acquired using 1.5T and 3T MR scanners, and across several centres showing the robustness of the standardization framework across diverse sets of data. Further, the image standardization can improve the robustness of automated algorithms, as the mathematical relationships they use for analyses operate more similarly between different images.

By analyzing local contrast around WML and ensuring that values do not decrease following intensity standardization, preservation of WML can be assumed. As shown in Table 3, local contrast can be increased following image standardization. The increased local contrast with intensity standardization of WML intensities can increase the robustness and accuracy of WML segmentation algorithms.

Additionally, there has been growing interest in the analysis of Dirty-Appearing White Matter (DAWM), which is defined as regions of the brain with an intermediate intensity between those of WML and normal-appearing white matter [49]. It is possible that the intensity standardization of brain pixel intensities using the image standardization framework described herein will also align the intensity range of DAWM, which may allow for future works to analyze this phenomenon more objectively.

Image intensity distributions between MR scanners, and even within MR scanners, can vary greatly due to differences in proprietary reconstruction algorithms and acquisition parameters. As shown in FIGS. 1A-1H, while the image intensity distributions can vary depending on the MR scanner manufacturer, these variations can be accounted for and minimized using the image standardization framework described herein.

For WML segmentation, as shown in FIGS. 9A-9B, processing images with the image standardization framework described herein can yield a more consistent edge map, meaning that the segmentation algorithm can be more robust across image datasets. In addition, the standardized image data can yield more accurate image segmentations than the original data for all lesion loads, suggesting that the integrity of WML is maintained following intensity standardization.

Image registration can be performed to account for differences in voxel resolution and patient orientation. By normalizing these artifacts as described above, algorithms using feature extraction can have consistent meaning for positional features, kernel sizes, and features affected by rotation.

The statistically significant increase in DSC and decrease in subject head angle for the tests performed herein demonstrates that an image registration step can be used to align the image volumes with the atlas image volume, therefore reducing the effects of variations in resolution and patient orientation.

Comparison of Different Image Standardization Methods on Brain Tissue

Figure 12:
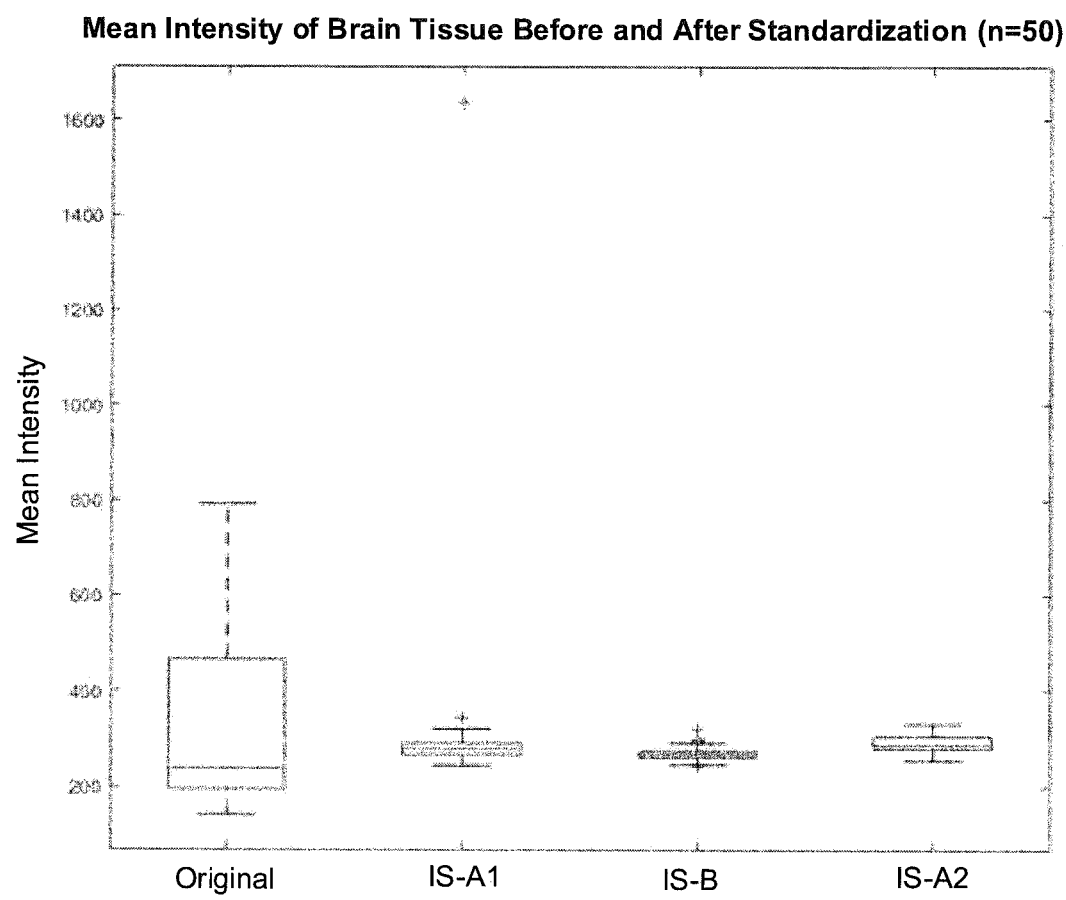
FIG. 12 shows bar plots of the mean intensity for brain pixels for 50 volumes before image standardization, after image standardization using a first method along with 2D bias field reduction, after image standardization using a second method along with 2D bias field reduction and after image standardization using the first method along with 3D bias field reduction.

The overall standardization framework can be assessed by its ability standardize the pixel intensities of pure tissue classes such as the brain. FIG. 12 shows bar plots of the mean intensity for brain pixels for 50 volumes before image standardization (i.e. "original"), after image standardization using a first method along with 2D bias field reduction (i.e. "IS-A1"), after image standardization using a second method along with 2D bias field reduction (i.e. "IS-B") and after image standardization using the first method along with 3D bias field reduction (i.e. "IS-A2"). In this case, the image standardization that uses the first method employs the image slice refinement described in equations (7c) and (7d) while the image standardization that uses the second method employs the image slice refinement described in equations (7a) and (7b). Both methods use the same volume refinement (i.e. volume standardization).

The volumes were acquired from the Canadian Atherosclerosis Imaging Network (CAIN) dataset. For each of the volumes, manual segmentations (i.e. ground truth masks) were provided for the brain, ventricles, and WML respectively. The brain mask was multiplied by the original image volume to isolate the brain region. In addition, the WML and ventricle masks were subtracted from the isolated brain region to ensure that all pixels belonged strictly to the brain tissue class.

Compared to the original volumes, the standardized volumes (IS-A1 and IS-B) have significantly less variance in mean intensity values. This implies that the mean intensities of the 50 volumes are more similar following standardization. The second image standardization method appears to further reduce the spread of the image data compared to the first image standardization method. Additionally, the first image standardization method has an outlier with a significantly higher mean intensity. This is not the case with the second image standardization method as the only detected outlier is very close to the other data points. These test results imply that the second image standardization method appears to be more effective at normalizing intensity values of the brain pixels. The last results "IS-A2" are for the first image standardization method along with 3D bias field reduction. It appears that using 3D bias field reduction results in better performance compared to using 2D bias field reduction since while the boxplots for IS-A1 and IS-A2 have a comparable spread, the boxplot for IS-A2 has no extreme outliers. However, the performance of IS-A2 is still below that of IS-B since the boxplot for IS-A2 is not as compressed as the box-plot for IS-B meaning that the mean intensities span a greater range and have greater variance.

Intensity Standardization Using Image Slice Refinement

In another aspect, in accordance with the teachings herein, there is provided another method of image standardization which uses image slice refinement but not volume refinement. In this case, the histogram for the image volume is used as the reference histogram (i.e. atlas histogram) and the image slices of the image volume are each aligned with the volume histogram. However, in other embodiments, the reference volume landmark may be an atlas volume landmark from a histogram of an atlas volume, an image slice landmark from the histogram of an atlas image slice, an image landmark from a histogram of one of the image slices from the image volume, or a histogram of an image slice from a different image volume.

This technique of performing image slice refinement without volume standardization can be done to ensure uniformity across image slices, without the extra processing steps of image volume alignment. This method may also remove the dependence on an atlas or reference image volume, since the histogram of the image volume may be used. This may be beneficial for within patient comparisons, or for matching the intensities of image slices between patients.

In accordance with this aspect, the method for processing a digital magnetic resonance (MR) image volume from an image data set comprises separating the digital MR image volume into a plurality of digital MR image slices; and performing slice refinement for each digital MR image slice by: generating an image slice histogram; determining an image slice landmark from the image slice histogram; and generating a transformed digital MR image slice by applying a transformation function to the image slice to align the image slice landmark with a reference landmark. The reference landmark may be image volume landmark from a histogram of the image volume or another landmark as described above.

In some embodiments, the transformation function is in accordance with equations (7c) and (7d) and involves applying a scaling factor of $\gamma = A/J$ to the image slice histogram where J is the intensity of the image slice landmark, and A is intensity of the reference landmark. In other embodiments, the transformation function is in accordance with equations (7a) and (7b) and involves shifting the image slice intensity values by an image slice shifting factor to align the image slice landmark with the reference image volume landmark. For both of these cases, the image reference landmark of the histogram of the digital MR image and the image slice landmarks of the image slice histograms may be the modes of each corresponding histogram.

This method may involve one or more of the acts described previously for method 200 and may also be used with method 300 which is described later with respect to FIG. 13. This method may also be performed by the system 100 shown in FIG. 3.

Whole Volume Brain Extraction, Ventricular Segmentation and Midline Detection in FLAIR MRI When standardized images and image volumes are created using the teachings herein, further analysis may be conducted on the intensity and spatially normalized images (e.g. the spatial normalization can be done by performing image registration and ensuring that the voxels have the same resolution as in act 214). For example, algorithms that achieve whole volume brain extraction, ventricular segmentation and midline estimation may be performed. Accordingly, in another aspect, the teachings herein provide a novel classification framework for robust and automatic whole volume brain extraction on standardized FLAIR MRI images although the teachings herein can also be extended to other types of MR imaging. Brain extraction via thresholding is not feasible for the large-scale analysis of MC datasets, as it cannot account for WML located on the periphery of the brain. However, the use of a supervised classifier, as described herein, allows for the incorporation of image features, which can account for this challenge. Following whole volume brain extraction on standardized image volumes, the ventricles may be segmented and the midline can be estimated allowing for the extraction of clinical metrics, such as the volume of the objects detected.

Figure 13:
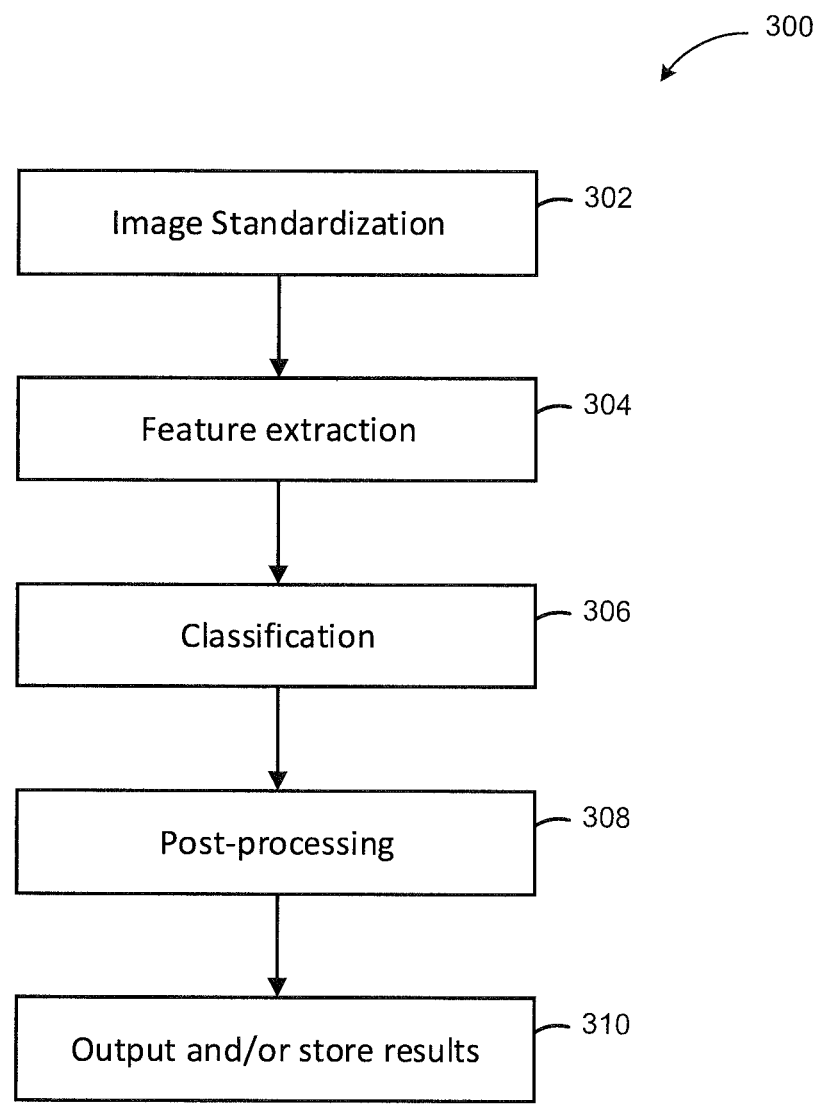
FIG. 13 is a flowchart of an example embodiment of a method for brain segmentation, feature extraction and feature classification for MRI images of the brain using intensity standardization in accordance with the teachings herein.

Referring now to FIG. 13, shown therein is an example embodiment of a brain extraction method 300. The method 300 comprises performing image standardization (act 302), feature extraction (act 304), classification (act 306) and post-processing (act 308). The results can then be output (act 310), such as to a display, and/or stored in a data store.

At act 302, image standardization is performed as described previously on the MR image volume (e.g. raw MR image data) to generate a standardized MR image volume. The image standardization produces standardized MR image data that has a reduction in variability by robustly suppressing acquisition artifacts (such as acquisition noise, bias field, intensity non-standardness, etc.) and image registration, as described previously, which normalized the voxel size between images, and ensured that the position of the brain in all images was similar, therefore maximally aligning anatomy between subjects. It should be noted that certain acts of the preprocessing and post-processing may be optional. For example, reducing acquisition noise, removing bias field, performing background subtraction, shifting the histogram to zero and performing image registration may be optional in certain cases.

At act 304, feature extraction is performed on the standardized MR image volume to generate feature values for a set of features. Feature normalization may then be performed on the set of features to obtain a set of normalized feature values. Feature extraction can be done following image standardization using a smaller number of features due to the improvement in image quality from image standardization. In this embodiment, 25 features were initially extracted on a per-voxel basis for each image volume and analyzed to see which of the features resulted in improved classification. However, in other embodiments, many other types of features may be used. For this example embodiment, the features comprised positional features including the $(x_1; x_2; x_3)$ coordinates of each voxel since the anatomy of subjects have been aligned and the voxel resolution has been normalized. The voxel intensity was also extracted as a feature as intensity standardization has made intensity consistent across all images. The gradient magnitude at three different scales was also extracted from a standardized image volume, $Y(x_1, x_2, x_3)$. First, the image gradient was calculated in 3D:

$$\|\nabla y\| = \sqrt{\left|\frac{\partial y}{\partial x_1}\right|^2 + \left|\frac{\partial y}{\partial x_2}\right|^2 + \left|\frac{\partial y}{\partial x_3}\right|^2} \quad (17)$$

where the Sobel operator was used. Although the Sobel operator was used, other gradient approximations such as Laplacian, Roberts and Prewitt operators may be used in other embodiments. The magnitude features were calculated by taking the average magnitude of the neighbourhood surrounding each pixel defined by kernels of 2, 4, and 8 mm. In other embodiments, different kernel sizes may be used and an alternate definition of the magnitude may be used, such as the absolute value. The brain is smoother relative to the surrounding tissues, likely making this edge-quantifying feature highly discriminatory. The different scales will capture different degrees of edge information, and a larger neighbourhood may be the most robust to WML edges, but still accurately capture the brain boundary. The Gaussian derivatives (up to first order) were also extracted at the previously mentioned scales in 3D. The 0th order derivative was defined as:

$$G(x_1, x_2, x_3, \sigma) = \frac{1}{2\pi\sigma^2} e^{-\frac{(x_1^2 + x_2^2 + x_3^2)}{2\sigma^2}} \quad (18)$$

and the $1^{st}$ order derivative was defined as:

$$\frac{\partial G(x_1, x_2, x_3, \sigma)}{\partial x_1} = -\frac{x_1}{2\pi\sigma^4} e^{-\frac{(x_1^2 + x_2^2 + x_3^2)}{2\sigma^2}} \quad (19)$$

at 2, 4, and 8 mm. In other embodiments, different kernel sizes may be used. These features present a local representation of each image on different scales in order to discriminate between brain and non-brain tissues based on the surrounding pixels and tissues. Extraction of the Gaussian derivatives yielded 18 features: G(x; 2 mm), G(x; 4 mm), G(x; 8 mm), ∂G(x; 2 mm), ∂G(x; 4 mm), and ∂G(x; 8 mm), where the feature was calculated for all $x = x_1, x_2, x_3$.

The number of features used for classification may be reduced in order to lessen computational load and classifier complexity. It is useful to reduce the dimensionality of the feature set in order to reduce computational costs, as well as to increase classification accuracy by reducing noise. Also, it makes the features and their characteristics more interpretable, allowing for better understanding of the data [60]. One way of determining the most discriminatory features can be to use the Minimum-Redundancy Maximum-Relevancy (mRmR) algorithm [61]. Other techniques may be used in other embodiments as is known by those skilled in the art. The mRmR algorithm determines the mutual information between the features, and in turn ranks the features in order of importance. However, it does not indicate how many of these features can be used to yield the best performance for the classifier. It may be possible to use all, or any subset of these features in an implementation depending on the dataset that is being analyzed and the desired performance. Additionally, other features may be defined.

In order to determine the number of features that yield the best accuracy, the classifier can be trained with different permutations of the standardized image data, and the feature subset with the greatest accuracy can be used in the final classifier. In this example embodiment, the classifier was constructed with 200 trees and 100,000 examples extracted from training data randomly selected from the dataset, using all 25 features. It was then tested on the remaining image volumes, and performance was assessed using classification accuracy (ACC) using the confusion matrix, which is defined as:

$$ACC = \frac{TP + TN}{TP + TN + FP + FN} \quad (20)$$

where TP, TN, FP, and FN represent the true positive, true negative, false positive, and false negative rates, respectively.

At each iteration, the feature with the lowest importance from the mRmR algorithm was dropped for the subsequent iteration. This was repeated until only one feature remained.

Using the mRmR feature evaluation approach, for this particular dataset, the number of features was found to be seven, which yielded a classification accuracy of about 95.47%+/−1.67%. While the use of twelve features resulted in a slightly higher classification accuracy (less than a one percent increase in classification accuracy), the use of a smaller number of features is more desirable, and therefore, the previously mentioned seven features were selected in this example embodiment but another number of features can be selected in other embodiments as explained previously. For this example embodiment, the selected features were: pixel intensity, $x_3$ coordinate, $x_2$ coordinate, $x_1$ coordinate, Gaussian first derivative of $x_2$ at a scale of 2 mm, Gaussian first derivative of $x_2$ at scale of 4 mm, and the gradient edge magnitude at a scale of 8 mm. These features were found to demonstrate several important characteristics of the images for the datasets that were analyzed and these characteristics included: (i) that intensity and position of the brain are important to classification, which can be attributed to the normalization of these features via the standardization framework (i.e. both intensity and image standardization); (ii) that the Gaussian derivatives at two different scales capture diverse local representations of the tissues surrounding each pixel; and (iii) that the gradient edge magnitude feature indicates that the smooth texture of the brain is a highly discriminatory feature, but also that the large neighbourhood kernel aids in robustness against the edge effects of WML, while maintaining the ability to identify the brain boundary. In general, most permutations of the data yielded relatively optimal results (e.g. a classification accuracy greater than 95%), and this is likely due to image standardization and the inherent robustness of the Random Forest (RF) classifier. As the variability in the images was reduced, the overall accuracy of the classifier increased.

The features were also normalized using feature standardization as this demonstrated the best performance (96% of pixels were classified accurately), and was utilized in the classifier in this particular example. Feature standardization (or Z-score normalization) [62] scales the features so that they have a mean equal to zero, and a standard deviation of one. The standard scores (or Z-scores) are calculated as follows:

$$Z = \frac{x - \mu}{\sigma} \quad (21)$$

where Z is the normalized feature vector, x is the original feature vector, and $\mu$ and $\sigma$ are the mean and standard deviation of that vector, respectively.

At act 306, classification is performed on the standardized MR image volume using a classifier and the normalized feature values to generate classification results. For example, the RF classifier [59], was used in this example embodiment as it can be used on a small, simple, and intuitive feature set, which is robust to the presence of WML in the gray and white matter tissues. As the images are standardized, the features do not need to capture a large range of variability, making them more robust. The output is a binary segmentation mask, which is a 3D mask of the brain for the whole image volume. It should be noted that other classifiers can be used in other embodiments such as, but not limited to, SVM, mixture models, Bayes classification, linear regression, neural networks, and decision trees.

Classifier Construction and Training:

The RF classifier was constructed with parameters that resulted in the best performance for the training dataset. The number of trees was chosen to yield a good trade-off between generalization accuracy and computational complexity. The number of features analyzed at each node was set to 2, which is somewhat low; however, with a large number of trees, the strength of individual trees is less relevant. The minimum number of training voxels present at a node and leaf was set to 20 [37]. Different values for maximum tree depth was also explored, which determines the number of nodes that a tree can "grow". With greater depth comes an increase in accuracy, but this can also lead to overfitting of the training set and more computational overhead. Due to the high correlation of voxels in an image volume, not all voxels are used in training, which reduces classifier complexity and computational load. The number of training examples were evenly distributed between positive and negative cases. This equal distribution was used to avoid any bias of class imbalances during training, which is a known concern with RF classifiers [63]. Within the negative cases, 75% of examples were restricted to lie within 3 mm of the brain boundary, as this is where the harder examples lie, which allowed the RF classifier to process more of these examples and make it more robust [37]. The features that were found to be the most informative, chosen by feature selection, as explained earlier, were then used for training.

The number of trees was investigated (from one to 500), and the number that yielded the greatest performance was selected as the parameter setting for the RF classifier. The depth of the trees was evaluated from one (also known as a stump) to unrestricted depth, and generalization was increased by pruning after training. Pruning is the process of randomly removing some branches of each tree after training; this is known to suppress any effects of over-fitting of the training set, therefore increasing generalization to new data [63].

The depth that resulted in the best performance during training was implemented in the RF classifier. The number of examples used for training was also analyzed, as there is trade-off between classification accuracy and overfitting, as well as computational complexity. It is known that increased complexity of an RF classifier can eventually lead to an increase in error as well [63]. A range of values was used, from 100 to 1,000,000. The number of examples with the greatest accuracy was implemented in the RF classifier.

It should be understood that the above parameters are tunable for the RF classifier and depend on the data that is being classified and other embodiments may use other parameters. It is possible to use other types of classifiers as well, some of which were previously discussed, which may have different parameters that can be tuned to achieve an acceptable level of performance.

For example, it was found that the number of trees did not have a significant impact on the accuracy of the classifier (average accuracy was 94.76%+/−1.26). This is likely due to image standardization, as a relatively low amount of variability in image properties reduces noise in the feature set, making individual trees more robust. Because of this, the use of 200 trees was selected, as this yielded the best results in similar work [37]. The number of training examples was determined using sensitivity and specificity. The best accuracy and sensitivity were achieved with approximately 80,000 examples. However, the best specificity was found at 150,000 examples. Thus, 150,000 training examples were selected, as it yields the best trade-off between the three metrics, and this number of training examples likely yields good generalization across datasets without overfitting. The output of the classification act is a single mask that shows which pixels belong to the region of interest, which in this case is the brain. In other embodiments that deal with other imaging modalities of images of other body parts the number of trees may be different.

At act 308, post-processing is performed on the classification results to reduce false positives. The post-processing may comprise applying mathematical morphology after classification to suppress false positives, which is a common issue in machine-learning based approaches to brain extraction [37, 38]. This simple post-processing step deeply contrasts with other brain extraction approaches, which require complex models to perform post-processing of the brain segmentations, such as generative models or graph cuts [37, 64].

The post-processing comprises eroding the masks (from the classification act) using a kernel size of 4, in order to remove any small structures still connecting the brain to non-brain structures. Any small clusters of voxels not connected to the central brain mass were then deleted. The remaining mask was dilated by a kernel size of 6 to reverse the effects of the initial erosion kernel, and then any holes within the masks were filled. This is made possible by the use of standardized images. Due to the reduced variability in image properties from intensity and image standardization, the RF classifier is exceptionally robust on its own, and a complex model is not required to suppress the relatively small number of false positives.

Using the intensity and image standardized and brain extracted image volumes, the midline may be estimated. The midline plane estimation algorithm relies on the detection of the longitudinal fissure between hemispheres of the brain. It works on the assumption that the optimal mid-sagittal plane is a plane that contains the maximal area of CSF in the image, excluding the ventricles. In FLAIR images, CSF appears as low intensity pixels (as the CSF signal is nulled at acquisition). Therefore, the goal of this approach is to determine the sagittal plane that minimizes the mean pixel intensity, yielding the optimal midline plane. This approach was implemented by applying a threshold to the standardized images as a pre-processing step, followed by the estimation of an initial mid-sagittal plane. Based on the location of this plane, the search begins by analyzing if translation or rotation of this plane may result in a better plane. If a better plane is found, the process repeats until no better plane can be found. Note that thresholding is possible due to the intensity standardization step.

First, a threshold is applied to the standardized images, in order to null high intensity pixels (i.e. WML and flow-related artifacts in the ventricles) that may skew the calculation of the mean pixel intensity of the plane; for example, a threshold of 400 may be applied. To determine the initial candidate plane, the scores (mean pixel intensity) of all sagittal planes within fraction (for example, 50%) of the image width from the centroid were calculated, and the plane with the lowest score was selected. This restriction on the plane search reduced the changes that slices tangent to the brain surface were selected.

Once the best initial plane was found, the score for several small transformations of this plane were determined. If none of the transformations resulted in a better score, the current plane was set as the best midline plane, and this search was then stopped; otherwise, the plane with the best score was then considered as the best plane, and the method was repeated. Eleven transformations were determine at each step of this search, i.e.: translation of the plane in the X-direction by some small number of pixels (for example, one or two) in both directions, as well as rotation of the plane of varying angle increments (for example, from 0.1 to 3 degrees) in both directions.

Using the intensity normalized and brain extracted image volumes, the ventricles can be segmented. Segmentation of the ventricles was performed in a way that was adapted from [65]. First, a threshold was applied to the standardized images (for example, a threshold of 200), nulling pixels belonging to the gray or white matter classes, and yielding an approximate binary mask of the CSF. Because the CSF occupies the ventricles, as well as the subarachnoid space surrounding the brain, the false positives along the brain boundary may be removed. This was done by applying a large erosion kernel (for example, a 25 mm kernel) to the brain mask, and in turn, multiplying it by the CSF mask, removing the previously mentioned false positives. This yielded an approximate segmentation of the ventricles. The two largest remaining connected volumes were then labelled as ventricular CSF.

This yielded accurate results across most subjects; however, in those with relatively small ventricles, incorrect objects may be detected as ventricular CSF. To combat this, a series of tests may be conducted on the detected objects to determine if they were in fact, the ventricles. These included tests for closeness to center of mass, as well as a check to ensure that both ventricles weren't contained in the same object (i.e. if the two largest objects are kept and the ventricles are in one object, an incorrect structure may also be segmented).

At act 310, the method 300 comprises outputting classification results and/or storing classification results. The classification results can be displayed alone or along with the corresponding images on a monitor, printed as an image, saved as a digital image, emailed to a particular medical professional, stored on a data store or any combination these actions.

Image Dataset for Brain Extraction

In this framework, a classifier was trained using 108 randomly selected image volumes from the DB1 acquired from nine centres on MR scanners from three different vendors. The classifier was then tested on 27 randomly selected image volumes from DB1 (ischemic disease) that were different from the training data, and 21 randomly selected image volumes from DB2 (dementia). Specifications are listed in Table 1. Validation using these images demonstrated the robustness of the classification framework across MC and multi-disease datasets, increasing its potential for clinical utility.

Classifier Experimental Results

Initially, the effects of standardization (i.e. intensity and spatial normalization) of images on classifier performance were evaluated. Two RF classifiers were generated: one trained using the original image volumes of the DB1 training set without standardization, and one trained using the corresponding standardized images. For both classifiers, the out-of-bag (OOB) accuracy was evaluated as an average over 10 experiments, where 76 image volumes were used for training, and 32 image volumes were used for testing in each run (as this is an approximation of the 70/30 split common to the machine learning literature [63]). These experiments are labelled OOB-Original and OOB-Standardized, and these validation scores allow for the determination of whether image standardization is beneficial to automated segmentation algorithms.

The classifier trained on standardized images was then applied to the test cases from DB1 (ischemic disease) and DB2 (dementia). Table 5 contains a summary of segmentation metrics across these datasets, and FIGS. 14A-14L contains sample segmentation results. In particular, FIGS. 14A-14L show sample segmentation results across datasets for different scanners and disease classifications. For each example, the original image and ground-truth outline is shown, followed by the automated segmentation.

Overall, the classifier yielded acceptable results across all disease manifestations in these diverse datasets. Experimentation began by analyzing the effects of standardization of images on segmentation accuracy. When comparing standardized images to original images, the Dice Similarity Coefficient (DSC), sensitivity, and specificity were all increased using standardized data, indicating better agreement with the ground-truth segmentations. In the case of Hausdorff Distance (HD) [30], the smaller distance achieved by the standardized image data demonstrates that the fine details of the sulci were better localized than with the original data, and a lowered Extra Fraction (EF) [65] measurement indicates that the false positive (FP) rate was reduced. In general, the variance in these metrics was also greatly reduced using standardized data.

TABLE 5

Summary of segmentation metrics across multi-centre and multi-disease datasets

| Dataset | DSC | HD | Sensitivity | Specificity | Extra Fraction |
|---|---|---|---|---|---|
| OOB - Standardized | 95.7 ± 3.0 | 2.63 ± 2.89 | 97.9 ± 1.23 | 95.4 ± 3.26 | 1.15 ± 0.86 |
| OOB - Original | 94.3 ± 4.22 | 2.45 ± 1.26 | 97.7 ± 1.49 | 88.2 ± 4.76 | 2.3 ± 1.01 |
| DB1 | 95.6 ± 2.84 | 2.15 ± 2.46 | 98.4 ± 1.18 | 95.3 ± 2.95 | 1.18 ± 0.79 |
| DB2 | 94.5 ± 2.48 | 2.10 ± 1.51 | 98.0 ± 0.98 | 94.0 ± 2.77 | 1.29 ± 0.62 |

It should be noted that the DSC was not significantly impacted by image standardization. However, an increase can be seen in specificity, which is a measure of the true negative rate. What this indicates is that non-standardized images were likely being under-segmented, but that this was corrected with image standardization. Additionally, image standardization yielded a decreased EF rate, indicating a reduction in false positives. As the DSC is only a measure of similarity between segmentations, it does not yield significant insight into how segmentations may be erroneous. For this reason, other accuracy measurements were analyzed as well.

An improvement in segmentation accuracy following image standardization implies that image standardization reduced the variability in images that had previously had significantly different characteristics than the training data. By reducing this variability, the accuracy of the classifier was increased on these difficult images. This is an indicator that image standardization is beneficial to automated algorithms for analysis, as MC variability is reduced, making algorithms more robust and accurate.

Midline Detection and Ventricle Segmentation Results

Figures 14A, 14B, 14C, 14D, 14E, 14F, 14G, 14H, 14I, 14J, 14K, 14L:
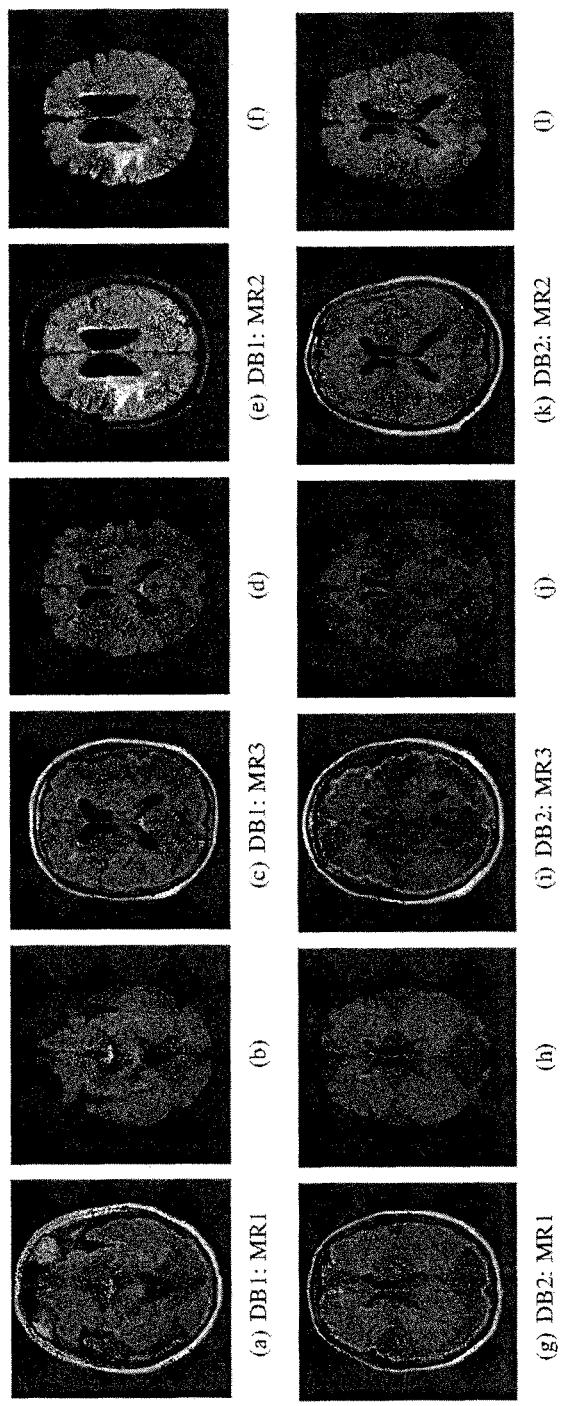
FIGS. 14A-14L show sample brain segmentation results across datasets for different scanners and disease classifications. For the example images in FIGS. 14A, 14C, 14E, 14G, 14I, and 14K, the MRI with the outlined regions is the original image with the manual segmentation generated by an expert, and the example images in FIGS. 14B, 14D, 14F, 14H, 14J, and 14L show the corresponding automated segmentation generated in accordance to FIG. 13.
Figure 15A:
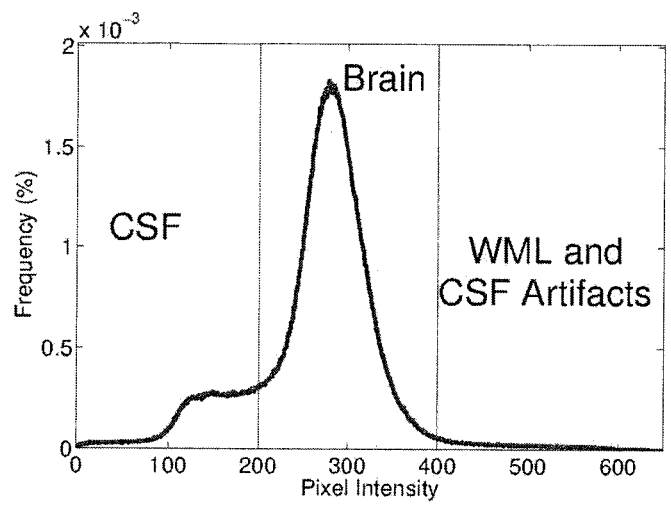
FIG. 15A-15E show a histogram of a standardized image slice, a standardized image slice, and three masks for different tissue classes based on different intensity thresholds, respectively.
Figure 15B:
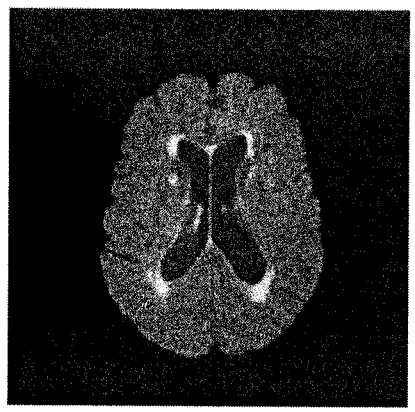
Figure 15C:
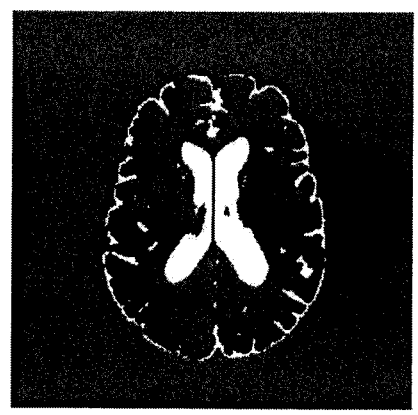
Figure 15D:
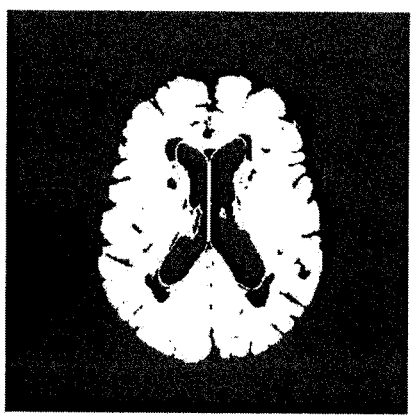
Figure 15E:
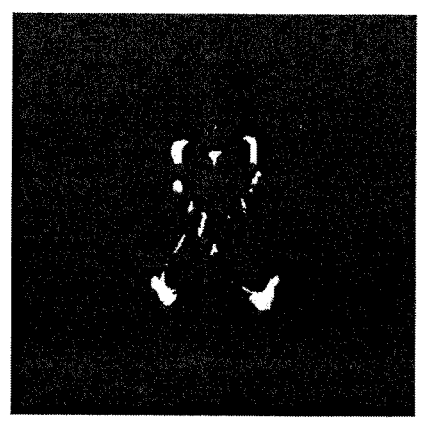
Figure 17A:
FIGS. 17A-17L show sample results of midline plane estimation, as well as WML and ventricle segmentation, across the range of disease classifications found in the DB2 dementia dataset.
Figure 17B:
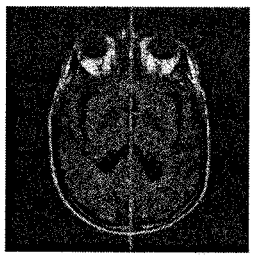
Figure 17C:
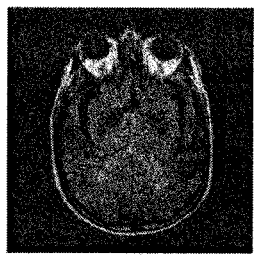
Figure 17D:
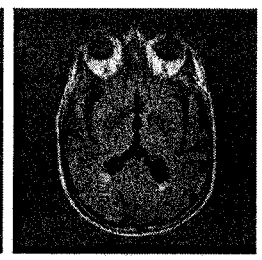
Figure 17E:
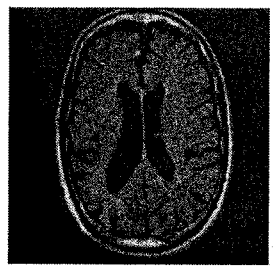
Figure 17F:
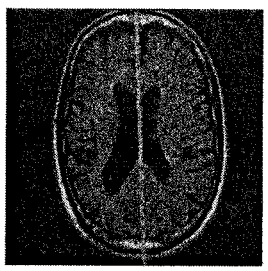
Figure 17G:
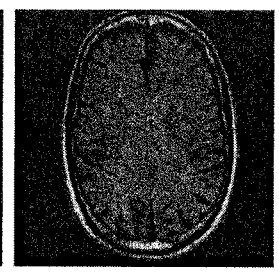
Figure 17H:
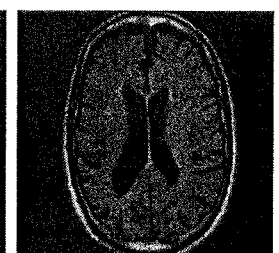
Figure 17I:
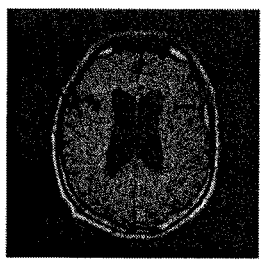
Figure 17J:
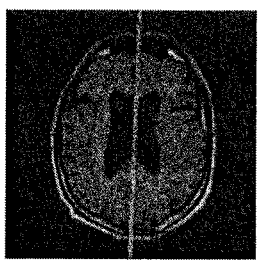
Figure 17K:
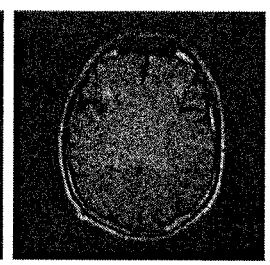
Figure 17L:
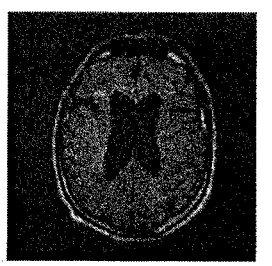

Once the brain has been segmented from an image, other structures may be segmented as well; for example, the midline of the brain can be estimated, and the ventricles can be segmented as previously discussed. The midline estimation and ventricle segmentation algorithms rely on thresholding in order to perform their respective calculations, which is only a feasible approach due to intensity standardization. As the histograms of the images have been aligned, the same thresholds can be robustly applied to images from all datasets in order to segment the images into different tissue classes. Examples of these thresholds can be seen in FIGS. 15A-15E, where thresholding creates accurate masks of various tissue classes in a standardized image. In particular, FIG. 15A shows a histogram of a standardized image slice, FIG. 15B shows the standardized image slice, FIG. 15C shows a mask for cerebrospinal fluid (CSF) based on pixels having an intensity lower than an intensity threshold of 200, FIG. 14D shows a mask for the brain based on pixels having an intensity in the intensity range of 200 to 400 and FIG. 15E shows a mask of WML and CSF artifacts based on pixels having an intensity larger than an intensity threshold of 400. These thresholding approaches cannot be applied to original, non-standardized images, as the intensity distributions of the tissues are different between different images, and in such cases preset thresholds do not yield accurate segmentations.

The WML segmentation algorithm previously described in the image standardization section and validated for standardized images, relies on the mapping of edge content in the images versus voxel intensity. By standardizing the intensity scale, this edge model may be nearly identical across an entire image database, therefore increasing the robustness of the segmentation algorithm.

Sample image processing results are shown in FIGS. 16A-16L, and 17A-17L for the DB1 and DB2 datasets, respectively. In particular, FIGS. 16A-16L show sample results of midline plane estimation, as well as WML and ventricle segmentation, across different scanner vendors in the DB1 ischemic disease dataset. The data was obtained using MR1. The first image in each row is the original image without receiving intensity standardization. The rest of the images in each row show different segmentation results after applying intensity standardization to the original image. FIGS. 17A-17L show sample results of midline plane estimation, as well as WML and ventricle segmentation, across the range of disease classifications found in the DB2 dataset. Again, the first image in each row is the original image without intensity standardization and the rest of the images in each row show different segmentation results after applying intensity standardization to the original image. The labels SMC (Subjective Memory Concerns), MCI (Mild Cognitive Impairment) and AD (Alzheimer's Disease) represent different disease classifications. The data for the first two rows was obtained using MR1, the data for the third row was obtained using MR2, the data for the fourth and fifth rows was obtained using MR3. As can be seen, the algorithms achieved robust and accurate results across diverse, MC, and multi-disease datasets.

The goal of the midline estimation algorithm was to find the optimal plane that minimized the mean intensity of the plane in order to identify the longitudinal fissure between the hemispheres. Due to thorough pre-processing of the images, the midline estimate algorithm was robust across all three datasets. The most difficult cases were found to occur when there were large WML near the midline of the brain. In these cases, the WML were nulled at the thresholding step, along with CSF flow-through artifacts, and the optimal plane was minimized at a point offset from the longitudinal fissure between the hemispheres. These cases were identified and corrected manually by adjusting the intensity for thresholding.

The ventricle segmentation algorithm also yielded robust results across datasets, as the use of thresholding is made feasible by using standardized images, as demonstrated in FIGS. 15A-15E. It was found that cases with subjects with severe brain atrophy created an obstacle for the algorithm, as the atrophy resulted in increased CSF space around the ventricles, and the algorithm in turn detected CSF objects outside of the ventricular system. These cases were corrected by manually restricting the area from which the ventricles can be detected.

As can be seen, the WML segmentation algorithm yielded accurate results across different disease manifestations. The algorithm was found to be robust in all cases, and no manual corrections were required. With these results, several metrics were extracted from the datasets, providing structural information of the brain, which will be used to identify characteristics specific to each neurodegenerative disease.

It should be noted that the automatic analysis of datasets of this scale is likely not feasible, as existing algorithms cannot be robustly applied without performing image standardization according to the teachings herein.

It should also be noted that in the image standardization techniques described in accordance with the teachings herein, there is no or piecewise modification to any of the underlying histogram distributions in the various process steps which is advantageous as this ensures that pathology is preserved. For example, the first phase of the histogram modification described herein employs a global, linear rescaling of the image volume histogram of the image volume being processed with a rescaling factor determined by the difference between the modes of an atlas image volume histogram and the histogram of the image volume being processed (other landmarks other than the mode can be used as described previously in different embodiments). This allows the ends of the histogram of the image volume being processed to expand or contract without restriction, which is especially important for maintaining the appearance of disease and lesions in MR images. This is in contrast to conventional methods in which piecewise modification between landmarks and/or clipping is done to the histogram which makes it more difficult to segment certain areas of interest such as WML in brain MR images.

The second phase of the image standardization methods described herein is a refinement phase, which linearly translates the histograms of the image slices of the image volume being processed to align the major peaks (i.e. modes) of each of these image slices with the major peak (i.e. mode) of the histogram of the image volume being processed (the image slices are slices of the image volume being processed). This second phase alignment aids in overlapping the histograms of each image slice in the image volume along the z-direction, which is useful for bias field correction and handling of any residual non-standardness. In contrast to the previous work that uses piece-wise linear transformations to align histogram landmarks [20], the proposed method allows the histogram bounds to change without restriction, which allows the appearance of pathology and WML to be maintained.

It should be noted that in other embodiments, only image slice refinement may be performed to align the histograms of the image slices of an image volume to the histogram of the image volume, or to another reference histogram as described previously, as this was found to improve image quality.

It should be noted that in other embodiments, the standardized image processing methodology, described in accordance with the teachings herein, may be used in a radiation treatment protocol or a surgical method since the standardized images allows for robust object detection that may result in an improved ability to detect a pathology that a surgeon wishes to remove or irradiate, or to track the progression or regression of a tumour/pathology as determined by the volume of the object over time.

In another embodiment, the standardized image processing methodology may be used with an automated protocol to perform at least one of: automatically choosing the lesion for surgical/radiation intervention, and/or automatically choosing the lesion in surgical planning (e.g. automated surgical location detection).

In another alternative embodiment, the standardized image processing methodology, described in accordance with the teachings herein, may be used to provide better quality images that are used during image guided surgery or biopsy. For example, these better quality standardized images, with or without segmentation, can be displayed on a monitor and then used by a surgeon for performing a biopsy or other surgery to a certain region of a patient's anatomy shown in the standardized image.

In other embodiments, the standardized image processing system may be used as a computer-aided diagnosis tool, that helps radiologists diagnose and measure pathology in images. Additionally, such a system can be used for research purposes, to analyze many patients and to extract measurements from the data that can be correlated with other clinical and imaging data.

While the applicant's teachings described herein are in conjunction with various embodiments for illustrative purposes, it is not intended that the applicant's teachings be limited to such embodiments as the embodiments described herein are intended to be examples. On the contrary, the applicant's teachings described and illustrated herein encompass various alternatives, modifications, and equivalents, without departing from the embodiments described herein, the general scope of which is defined in the appended claims.

REFERENCES

[1] M. Essig, H. Hawighorst, S. O. Schoenberg, R. Engenhart-Cabillic, M. Fuss, J. Debus, I. Zuna, M. V. Knopp, and G. van Kaick, "Fast fluid-attenuated inversion-recovery (FLAIR) MRI in the assessment of intra-axial brain tumors," *Journal of Magnetic Resonance Imaging*, vol. 8, no. 4, pp. 789-798, 1998.

[2] K. Oppedal, T. Eftestl, K. Engan, M. K. Beyer, and D. Aarsland, "Classifying Dementia Using Local Binary Patterns from Different Regions in Magnetic Resonance Images," *International Journal of Biomedical Imaging*, vol. 2015, pp. 1-14, 2015.

[3] M. Brant-Zawadzki, D. Atkinson, M. Detrick, W. G. Bradley, and G. Scidmore, "Fluid-Attenuated Inversion Recovery (FLAIR) for Assessment of Cerebral Infarction: Initial Clinical Experience in 50 Patients," *Stroke*, vol. 27, pp. 1187-1191, 1996.

[4] R. Grossman and J. McGowan, "Perspectives on Multiple Sclerosis," *American Journal of Neuroradiology*, vol. 19, pp. 1251-1265, 1998.

[5] P. S. Aisen, R. C. Petersen, M. Donohue, and M. W. Weiner, "Alzheimers Disease Neuroimaging Initiative 2 Clinical Core: Progress and plans," *Alzheimer's & Dementia*, vol. 11, no. 7, pp. 734-739, July 2015.

[6] J. Suckling, J. Henty, C. Ecker, S. C. Deoni, M. V. Lombardo, S. Baron-Cohen, P. Jezzard, A. Barnes, B. Chakrabarti, C. Ooi, M.-C. Lai, S. C. Williams, D. G. Murphy, E. Bullmore, and for the MRC AIMS Consortium, "Are power calculations useful? A multicentre neuroimaging study: Validation of the Voxel-Based Power Calculations," *Human Brain Mapping*, vol. 35, no. 8, pp. 3569-3577, August 2014.

[7] M. Bilello, N. Suri, J. Krejza, J. H. Woo, L. J. Bagley, A. C. Mamourian, A. Vossough, J. Y. Chen, B. R. Millian, T. Mulderink, C. E. Markowitz, and E. R. Melhem, "An Approach to Comparing Accuracies of Two Flair MR Sequences in the Detection of Multiple Sclerosis Lesions in the Brain in the Absence of Gold Standard," *Academic Radiology*, vol. 17, no. 6, pp. 686-695, June 2010.

[8] G. Bydder and I. Young, "MR Imaging: Clinical Use of the Inversion Recovery Sequence," *Journal of Computer Assisted Tomography*, vol. 9, no. 4, pp. 659-675, 1985.

[9] D. L. Parker, "Signal-to-noise efficiency in magnetic resonance imaging," *Medical Physics*, vol. 17, no. 2, p. 250, 1990.

[10] T. M. Link, S. Majumdar, C. Peterfy, H. E. Daldrup, M. Uffmann, C. Dowling, L. Steinbach, and H. K. Genant, "High resolution MRI of small joints: impact of spatial resolution on diagnostic performance and SNR," *Magnetic resonance imaging*, vol. 16, no. 2, pp. 147-155, 1998.

[11] A. Khademi, D. Hosseinzadeh, A. Venetsanopoulos, and A. R. Moody, "Nonparametric statistical tests for exploration of correlation and nonstationarity in images," in *International Conference on Digital Signal Processing (DSP)*, 2009, pp. 1-6.

[12] L. Friedman, G. H. Glover, D. Krenz, and V. Magnotta, "Reducing inter-scanner variability of activation in a multicenter fMRI study: Role of smoothness equalization," *NeuroImage*, vol. 32, no. 4, pp. 1656-1668, October 2006.

[13] T. T. T. Hah, J. Y. Kim, and S. H. Choi, "White Matter Hyperintensities Extraction Based T2-FLAIR MRI Using Non-Local Means Filter and Nearest Neighbor Algorithm," in *IT Convergence and Security (ICITCS)*, 2014 International Conference on IEEE, 2014, pp. 1-4.

[14] L. G. Nyul and J. K. Udupa, "On standardizing the MR image intensity scale," *Magnetic Resonance in Medicine*, vol. 42, pp. 1072-1081, 1999.

[15] D. Palumbo, B. Yee, P. O'Dea, S. Leedy, S. Viswanath, and A. Madabhushi, "Interplay between bias field correction, intensity standardization, and noise filtering for t2-weighted MRI," in *Engineering in Medicine and Biology Society, EMBC*, 2011 Annual International Conference of the IEEE.

[16] D. Garca-Lorenzo, S. Francis, S. Narayanan, D. L. Arnold, and D. L. Collins, "Review of automatic segmentation methods of multiple sclerosis white matter lesions on conventional magnetic resonance imaging," *Medical Image Analysis*, vol. 17, no. 1, pp. 1-18, January 2013.

[17] A. Khademi, A. Venetsanopoulos, and A. R. Moody, "Robust White Matter Lesion Segmentation in FLAIR MRI," *IEEE Transactions on Biomedical Engineering*, vol. 59, no. 3, pp. 860-871, March 2012.

[18] J. G. Sled, A. P. Zijdenbos and A. C. Evans, "A nonparametric method for automatic correction of intensity nonuniformity in MRI data", *IEEE Transactions Med. Imaging,* 17(1):87-97, February 1998.

[19] B. Reiche, A. R. Moody, and A. Khademi, "Effect of Image Standardization on FLAIR MRI for Brain Extraction," *Signal Image and Video Processing*, vol. 9, no. 9, December 2015.

[20] R. de Boer, F. van der Lijn, H. Vrooman, M. Vernooij, M. Ikram, M. Breteler, and W. Niessen, "Automatic segmentation of brain tissue and white matter lesions in MRI," in *IEEE International Symposium on Biomedical Imaging (ISBI)*, 2007, pp. 652-655.

[21] G. De Nunzio, R. Cataldo, and A. Carl, "Robust Intensity Standardization in Brain Magnetic Resonance Images," *Journal of Digital Imaging*, February 2015.

[22] N. J. Tustison, B. B. Avants, P. A. Cook, Y. Zheng, A. Egan, P. A. Yushkevich, and J. C. Gee, "N4ITK: Improved N3 Bias Correction", IEEE Trans. Medical Imaging, 29(6): 1310-1320, June 2010.

[23] Y. Zhong, D. Utriainen, Y. Wang, Y. Kang, and E. M. Haacke, "Automated White Matter Hyperintensity Detection in Multiple Sclerosis Using 3d T2 FLAIR," *International Journal of Biomedical Imaging*, vol. 2014, pp. 1-7, 2014.

[24] E. Reinhard, M. Ashikhmin, B. Gooch, and P. Shirley, "Color transfer between images," *IEEE Computer graphics and applications*, vol. 21, no. 5, pp. 34-41, 2001.

[25] A. Winkler, P. Kochunov, and D. Glahn, "FLAIR Templates." [Online]. Available: http://glahngroup.org.

[26] M. Sdika and D. Pelletier, "Non-rigid registration of multiple sclerosis brain images using lesion inpainting for morphometry or lesion map-ping," *Human Brain Mapping*, vol. 30, no. 4, pp. 1060-1067, April 2009.

[27] M. Brett, A. P. Leff, C. Rorden, and J. Ashburner, "Spatial Normalization of Brain Images with Focal Lesions Using Cost Function Masking," *NeuroImage*, vol. 14, no. 2, pp. 486-500, August 2001.

[28] F. Huang, H. Cheng, and S. Vijayakumar, "Gradient weighted smoothing for MRI intensity correction," in *Engineering in Medicine and Biology Society, 2005. IEEE-EMBS 2005. 27th Annual International Conference of the IEEE,* 2006, pp. 3016-3019.

[29] M. d. C. Valds Hernndez, Z. Morris, D. A. Dickie, N. A. Royle, S. Muoz Maniega, B. S. Aribisala, M. E. Bastin, I. J. Deary, and J. M. Wardlaw, "Close Correlation between Quantitative and Qualitative Assessments of White Matter Lesions," *Neuroepidemiology*, vol. 40, no. 1, pp. 13-22, 2013.

[30] A. Khademi, A. Venetsanopoulos, and A. R. Moody, "Automatic contrast enhancement of white matter lesions in FLAIR MRI," in IEEE International *Symposium on Biomedical Imaging*. IEEE, 2009, pp. 322-325.

[31] C. Wyatt, Y.-P. Wang, M. Freedman, M. Loew, and Y. Wang, "Chapter 7," in *Biomedical Information Technology*. Elsevier, 2007, pp. 165-169.

[32] K. H. Zou, S. K. Warfield, A. Bharatha, C. M. Tempany, M. R. Kaus, S. J. Haker, W. M. Wells, F. A. Jolesz, and R. Kikinis, "Statistical validation of image segmentation quality based on a spatial overlap index 1: Scientific reports," *Academic radiology*, vol. 11, no. 2, pp. 178-189, 2004.

[34] R. Stokking, K. L. Vincken, and M. A. Viergever, "Automatic Morphology-Based Brain Segmentation (MBRASE) from MRI-T1 Data," *NeuroImage*, vol. 12, no. 6, pp. 726-738, December 2000.

[35] A. Khademi and A. R. Moody, "Multiscale Partial Volume Averaging Estimation for Segmentation of WML in FLAIR MRI," in *IEEE 12th Inter-national Symposium on Biomedical Imaging (ISBI)*, 2015, pp. 568-571.

[36] A. Khademi, A. R. Moody, and A. Venetsanopoulos, "Generalized Partial Volume Averaging Estimation for Cerebral MRI," *Journal of Medical Imaging*, vol. 1, no. 1, 2014.

[37] J. E. Iglesias, Cheng-Yi Liu, P. M. Thompson, and Zhuowen Tu, "Robust Brain Extraction Across Datasets and Comparison With Publicly Available Methods," *IEEE Transactions on Medical Imaging*, vol. 30, no. 9, pp. 1617-1634, September 2011.

[38] J. Kleesiek, G. Urban, A. Hubert, D. Schwarz, K. Maier-Hein, M. Bendszus, and A. Biller, "Deep MRI brain extraction: A 3d convolutional neural network for skull stripping", *NeuroImage*, vol. 129, pp. 460-469, April 2016.

[39] J. Rolland, V. Vo, and C. Abbey, "Fast Algorithms for Histogram-Matching: Application to Texture Synthesis," *Journal of Electronic Imaging*, vol. 9, no. 1, pp. 39-45, January 2000.IEEE, 2011, pp. 5080-5083.

[40] Brain Canada Foundation, "Annual Report 2015," tech. rep., Brain Canada Foundation, Montreal, Quebec (2015).

[41] P. Schmidt, C. Gaser, M. Arsic, et al., "An automated tool for detection of FLAIR-hyperintense white-matter lesions in Multiple Sclerosis," NeuroImage 59, 3774-3783 (2012).

[42] C. Dufouil, A. De Kersaint-Gilly, V. Besancon, et al., "Longitudinal study of blood pressure and white matter hyperintensities: the EVA MRI Cohort," Neurology 56, 921-926 (2001).

[43] E. J. van Dijk, M. M. Breteler, R. Schmidt, et al., "The Association Between Blood Pressure, Hypertension, and Cerebral White Matter Lesions: Cardiovascular Determinants of Dementia Study," Hypertension 44, 625-630 (2004).

[44] S. C. Ferguson, A. Blane, P. Perros, et al., "Cognitive ability and brain structure in type 1 diabetes relation to microangiopathy and preceding severe hypoglycemia," Diabetes 52(1), 149-156 (2003).

[45] R. A. R. Gons, A. G. W. van Norden, K. F. de Laat, et al., "Cigarette smoking is associated with reduced microstructural integrity of cerebral white matter," Brain 134, 2116-2124 (2011).

[46] J. Staals, S. D. Makin, F. N. Doubal, et al., "Stroke subtype, vascular risk factors, and total MRI brain small-vessel disease burden," Neurology 83(14), 1228-1234 (2014).

[47] J. M. Wardlaw, M. Allerhand, F. N. Doubal, et al., "Vascular risk factors, large-artery atheroma, and brain white matter hyperintensities," Neurology 82(15), 1331-1338 (2014).

[48] S. Debette, S. Seshadri, A. Beiser, et al., "Midlife vascular risk factor exposure accelerates structural brain aging and cognitive decline," Neurology 77(5), 461-468 (2011).

[49] J. Suckling, J. Henty, C. Ecker, et al., "Are power calculations useful? A multicentre neuroimaging study: Validation of the Voxel-Based Power Calculations," Human Brain Mapping 35, 3569-3577 (2014).

[50] M. Wilke, B. de Haan, H. Juenger, et al., "Manual, semi-automated, and automated delineation of chronic brain lesions: A comparison of methods," NeuroImage 56, 2038-2046 (2011).

[51] P. Malloy, S. Correia, G. Stebbins, et al., "Neuroimaging of white matter in aging and dementia," The Clinical Neuropsychologist 21, 73-109 (2007).

[52] N. Altaf, P. S. Morgan, A. Moody, et al., "Brain White Matter Hyperintensities Are Associated with Carotid Intraplaque Hemorrhage," Radiology 248, 202-209 (2008).

[53] N. Altaf, L. Daniels, P. Morgan, et al., "Cerebral White Matter Hyperintense Lesions are Associated with Unstable Carotid Plaques," European Journal of Vascular and Endovascular Surgery 31, 8-13 (2006).

[54] M. de Groot, B. F. Verhaaren, R. de Boer, et al., "Changes in Normal—Appearing White Matter Precede Development of White Matter Lesions," Stroke 44, 1037 (2013).

[55] J. M. Wardlaw, M. C. Valds Hernndez, and S. Muoz-Maniega, "What are White Matter Hyper-intensities Made Of? Relevance to Vascular Cognitive Impairment," Journal of the American Heart Association 4, 001140 (2015).

[56] N. Levy-Cooperman, J. Ramirez, N. J. Lobaugh, et al., "Misclassified Tissue Volumes in Alzheimer Disease Patients With White Matter Hyperintensities," Stroke 39, 1134 (2008).

[57] D. Garcia-Lorenzo, S. Francis, S. Narayanan, et al., "Review of automatic segmentation methods of multiple sclerosis white matter lesions on conventional magnetic resonance imaging," Medical Image Analysis 17, 1-18 (2013).

[58] C. Fennema-Notestine, I. B. Ozyurt, C. P. Clark, et al., "Quantitative evaluation of automated skull-stripping methods applied to contemporary and legacy images: Effects of diagnosis, bias correction, and scale location," Human brain mapping 27(2), 99-113 (2006).

[59] L. Breiman, "Random Forests," *Machine Learning*, vol. 4, no. 1, pp. 5-32, 2001.

[60] C. Ding and H. Peng, "Minimum Redundancy Feature Selection From Microarray Gene Expression Data," *Journal of Bioinformatics and Computational Biology*, vol. 3, no. 2, pp. 185-205, 2005.

[61] H. Peng, F. Long, and C. Ding, "Feature selection based on mutual information: criteria of max-dependency, max-relevance, and min-redundancy," *IEEE Transactions on Pattern Analysis and Machine Intelligence*, vol. 27, no. 8, pp. 1226-1238, 2005.

[62] L. Al Shalabi, Z. Shaaban, and B. Kasasbeh, "Data mining: A preprocessing engine," *Journal of Computer Science*, vol. 2, no. 9, pp. 735-739, 2006.

[63] J. Friedman, T. Hastie, and R. Tibshirani, *The elements of statistical learning*. Springer series in statistics Springer, Berlin, 2001, vol. 1.

[64] K. Li, X. Wu, D. Z. Chen, and M. Sonka, "Optimal surface segmentation in volumetric images-a graph-theoretic approach," *Pattern Analysis and Machine Intelligence, IEEE Transactions* on, vol. 28, no. 1, pp. 119-134, 2006.

[65] A. Khademi, and D. Hosseinzadeh, "Type II fuzzy systems for amyloid plaque segmentation in transgenic mouse brains for Alzheimer's disease quantification", SPIE 9041, Medical Imaging 2014: Digital Pathology, 90410T (20 Mar. 2014).

The invention claimed is:

1. A non-transitory computer-readable medium having stored thereon program instructions that, when executed by a processor, configure the processor for performing a method of processing a digital magnetic resonance (MR) image volume from an image data set, wherein the method involves performing intensity standardization and the method comprises:
determining an image volume scaling factor to align an image volume landmark of a volume histogram of the digital MR image volume with a reference volume landmark of a reference histogram of a reference image volume; and
scaling intensity values of the digital MR image volume based on the image volume scaling factor to generate a scaled digital MR image volume.

2. The non-transitory computer-readable medium claim 1, wherein the method further comprises:
separating the scaled digital MR image volume into a plurality of scaled digital MR image slices; and
for each scaled digital MR image slice:
generating an image slice histogram;
determining an image slice landmark from the image slice histogram; and generating transformed digital MR image slices by applying a transformation function to align the image slice landmark with the image volume landmark; and
combining the transformed digital MR image slices to generate a standardized digital MR image volume.

3. The non-transitory computer-readable medium claim 2, wherein the image volume landmark of the histogram of the digital MR image, the reference volume landmark of the histogram of the reference image volume and the image slice landmarks of the image slice histograms are modes of each corresponding histogram.

4. The non-transitory computer-readable medium of claim 2, wherein the method further comprises storing the transformed digital MR image slices in a data store, storing the scaled digital MR image volume, displaying at least one of the transformed digital MR image slices and/or displaying the scaled digital MR image volume.

5. The non-transitory computer-readable medium of claim 2, wherein the method comprises determining a scaling factor based on a ratio of an intensity of an image slice landmark and an intensity of a reference landmark, and transformation comprises multiplying the digital MR image slice by the image slice scaling factor.

6. The non-transitory computer-readable medium of claim 2, wherein the digital MR image volume is obtained for a brain and the intensity values of the image volume landmark, the reference volume landmark and the image slice landmark correspond to intensity values falling within a predetermined intensity range corresponding to at least one of grey matter tissue, white matter tissue, cerebrospinal fluid and background noise.

7. The non-transitory computer-readable medium of claim 2, wherein intensity values of voxels in the scaled and transformed digital image slices that are below zero are set to zero.

8. The non-transitory computer-readable medium of claim 2, wherein the method further comprises applying a smoothing function to the image slice histograms of the scaled digital MR image slices prior to applying the transformation function.

9. The non-transitory computer-readable medium of claim 2, wherein the method further comprises performing denoising, and background removal on the digital MR image volume prior to performing the transformation function.

10. The non-transitory computer-readable medium of claim 9, wherein the method further comprises performing bias field correction on the digital image volume with or without the denoising and with or without the background removal and before performing the transformation function.

11. The non-transitory computer-readable medium of claim 9, wherein the denoising comprises applying a denoising filter to the digital MR image volume to produce a denoised digital MR image volume before performing the scaling of the digital MR image volume.

12. The non-transitory computer-readable medium of claim 9, wherein the background removal comprises removing, cropping, or zeroing pixels in each digital MR image slice of the digital MR image volume with intensity values in an upper or lower H % of a corresponding histogram of each digital image slice, where H is a real number.

13. The non-transitory computer-readable medium of claim 12, wherein the background removal comprises segmenting denoised digital MR image slices into foreground and background masks and assigning pixels in the background mask corresponding to non-tissue pixels an intensity value of zero.

14. The non-transitory computer-readable medium of claim 2, wherein the method comprises:
defining the image volume landmark, the reference volume landmark and the image slice landmark;
generating the histograms of the digital MR image volume, the reference image volume and the digital MR image slices; and
determining intensity values for the image volume landmark, the reference volume landmark and the image slice landmark for the corresponding histograms.

15. The non-transitory computer-readable medium of claim 2, wherein the method further comprises:
performing feature extraction on the standardized digital MR image volume to generate feature values for a set of features;
performing feature normalization on the set of features to obtain a set of normalized feature values;
performing classification on the standardized digital MR image volume using the normalized feature values to generate classification results; and
performing post processing on the classification results to reduce false positives.

16. The non-transitory computer-readable medium of claim 15, wherein performing the image standardization includes registering an intensity standardized digital MR image volume to a reference volume to spatially align the intensity standardized digital MR image volume to the reference volume.

17. The non-transitory computer-readable medium of claim 15, wherein the method further comprises performing an action for at least one of the standardized digital MR image volume and the classification results including at least one of storing at least one of the standardized digital MR image volume and the classification results in a data store and displaying the at least one of the standardized digital MR image volume and the classification results.

18. The non-transitory computer-readable medium of claim 15, wherein the post processing comprises applying mathematical morphology.

19. The non-transitory computer-readable medium of claim 1, wherein the reference image volume is an atlas image volume or another MR image volume from a central MR image database or a second database and the digital MR image volume is from the central MR image database, the second database or another database.

20. The non-transitory computer-readable medium of claim 1, wherein the image volume scaling factor is based on a ratio between respective intensity values of the reference volume landmark and the image volume landmark of the histograms of the reference image volume and the digital MR image volume, and the scaling comprises multiplying the digital MR image volume by the image volume scaling factor.

21. The non-transitory computer-readable medium of claim 1, wherein when the volume histogram has a different starting point than the reference histogram, the method further comprises normalizing voxel intensities of the digital MR image volume so that the volume histogram and the reference histogram have a common starting point.

22. The non-transitory computer-readable medium of claim 1, wherein the MR images are obtained using Fluid-Attenuated Inversion Recovery (FLAIR) MRI, T1-weighted MRI, T2-weighted MRI, Proton Density (PD) weighted MRI, Steady-State Free Precession (SSFP) MRI, Effective T2 (T2*) MRI, Diffusion Weighted Imaging (DWI) MRI, Apparent Diffusion Coefficient (ADC) MRI, Diffusion Tensor (DTI) MRI, and Dynamic Contrast Enhanced (DCE) MRI.

23. A non-transitory computer-readable medium having stored thereon program instructions that, when executed by a processor, configure the processor for performing a method of processing a digital magnetic resonance (MR) image volume from an image data set, wherein the method involves performing intensity standardization and the method comprises:
selecting a first transformation function for aligning an image volume landmark of a volume histogram of the digital MR image volume with a reference volume landmark of a reference histogram of a reference image volume; and
performing volume standardization on intensity values of the digital MR image volume by applying the first transformation function to generate a transformed digital MR image volume.

24. The non-transitory computer-readable medium of claim 23, wherein the first transformation function comprises applying a scaling factor of $\alpha=A/I$ to the image volume histogram image volume where A is an intensity of the reference volume landmark and I is an intensity of the image volume landmark so that the transformed digital MR image volume is a scaled digital MR image volume.

25. The non-transitory computer-readable medium of 23, wherein the method further comprises:
separating the transformed digital MR image volume into a plurality of digital MR image slices; and
performing slice refinement for each digital MR image slice by:
generating an image slice histogram;
determining an image slice landmark from the image slice histogram; and
generating a transformed digital MR image slice by applying a second transformation function to the image slice to align the image slice landmark with the image volume landmark.

26. The non-transitory computer-readable medium of claim 25, wherein the method further comprises performing denoising, and background removal on the digital MR image volume prior to performing the second transformation function.

27. The non-transitory computer-readable medium of claim 26, wherein the method further comprises performing bias field correction on the digital image volume with or without the denoising and without or without the background removal and before performing the transformation function.

28. The non-transitory computer-readable medium of claim 26, wherein the denoising comprises applying a denoising filter to the digital MR image volume to produce a denoised digital MR image volume before performing the scaling of the digital MR image volume.

29. The non-transitory computer-readable medium of claim 26, wherein the background removal comprises removing, cropping, or zeroing pixels in each digital MR image slice of the digital MR image volume with intensity values in an upper or lower H % of a corresponding histogram of each digital image slice, where H is a real number.

30. The non-transitory computer-readable medium of claim 29, wherein the background removal comprises segmenting denoised digital MR image slices into foreground and background masks and assigning pixels in the background mask corresponding to non-tissue pixels an intensity value of zero.

31. A non-transitory computer-readable medium having stored thereon program instructions that, when executed by a processor, configure the processor for performing a method of processing a digital magnetic resonance (MR) image volume from an image data set, wherein the method comprises:
separating the digital MR image volume into a plurality of digital MR image slices; and performing slice refinement for each digital MR image slice by:
generating an image slice histogram;
determining an image slice landmark from the image slice histogram; and
generating a transformed digital MR image slice by applying a transformation function to the image slice to align the image slice landmark with a reference landmark, wherein the transformation function comprises applying a scaling factor of $\gamma=A/J$ to the image slice histogram where J is the intensity of the image slice landmark, and A is intensity of the reference landmark so that the transformed digital MR image slices are scaled digital MR image slices.

32. The non-transitory computer-readable medium of claim 31, wherein the reference landmark comprises an image slice landmark from the histogram of an atlas image slice, an image slice landmark from a histogram of one of the image slices from the image volume, an image slice landmark from a histogram of an image slice from a different image volume, a landmark from a histogram of an image volume, or an image slice landmark of a histogram of an image slice.

33. The non-transitory computer-readable medium of claim 32, wherein the image slice landmarks of the image slice histograms are modes of each corresponding histogram.

34. The non-transitory computer-readable medium of claim 31, wherein the transformation function comprises shifting image slice intensity values by an image slice shifting factor to align the image slice landmark with the reference landmark so that the transformed digital MR image slices are shifted and scaled digital MR image slices.

35. The non-transitory computer-readable medium of claim 31, wherein the method further comprises performing denoising, and background removal on the digital MR image volume prior to performing the transformation function.

36. The non-transitory computer-readable medium of claim 35, wherein the method further comprises performing bias field correction on the digital image volume with or without the denoising and with or without the background removal and before performing the transformation function.

37. The non-transitory computer-readable medium of claim 35, wherein the denoising comprises applying a denoising filter to the digital MR image volume to produce a denoised digital MR image volume before performing the scaling of the digital MR image volume.

38. The non-transitory computer-readable medium of claim 35, wherein the background removal comprises removing, cropping, or zeroing pixels in each digital MR image slice of the digital MR image volume with intensity values in an upper or lower H % of a corresponding histogram of each digital image slice, where H is a real number.

39. The non-transitory computer-readable medium of claim 38, wherein the background removal comprises segmenting denoised digital MR image slices into foreground and background masks and assigning pixels in the background mask corresponding to non-tissue pixels an intensity value of zero.

40. A system for processing a digital magnetic resonance (MR) image volume from an image data set, wherein the processing includes performing intensity standardization and the system comprises:
a non-transitory memory;
at least one processor that, upon executing instructions stored in the non-transitory memory, is configured to:
determine an image volume scaling factor to align an image volume landmark of a volume histogram of the digital MR image volume with a reference volume landmark of a reference histogram of a reference image volume; and
scale intensity values of the digital MR image volume based on the image volume scaling factor to generate a scaled digital MR image volume.

41. The system of claim 40, wherein the at least one processor is further configured to:
separate the scaled digital MR image volume into a plurality of scaled digital MR image slices; and
for each scaled digital MR image slice:
generate an image slice histogram;
determine an image slice landmark from the image slice histogram; and
generate transformed digital MR image slices by applying a transformation function to align the image slice landmark with the image volume landmark; and
combine the transformed digital MR image slices to generate a standardized digital MR image volume.

42. The system of claim 41, wherein the image volume landmark of the histogram of the digital MR image, the reference volume landmark of the histogram of the reference image volume and the image slice landmarks of the image slice histograms are modes of each corresponding histogram.

43. The system of claim 41, wherein the at least one processor is further configured to apply a smoothing function to the image slice histograms of the scaled digital MR image slices prior to applying the transformation function.

44. The system of claim 40, wherein the at least one processor is further configured to store the transformed digital MR image slices in a data store, store the scaled digital MR image volume, display at least one of the transformed digital MR image slices and/or display the scaled digital MR image volume.

45. The system of claim 40, wherein the image volume scaling factor is based on a ratio between respective intensity values of the reference volume landmark and the image volume landmark of the histograms of the reference image volume and the digital MR image volume, and the scaling comprises multiplying the digital MR image volume by the image volume scaling factor.

46. The system of claim 40, wherein when the volume histogram has a different starting point than the reference histogram, the at least one processor is further configured to normalize voxel intensities of the digital MR image volume so that the volume histogram and the reference histogram have a common starting point.

47. A system for processing a digital magnetic resonance (MR) image volume from an image data set, wherein the system comprises:
a non-transitory memory;
at least one processor that, upon executing instructions stored in the non-transitory memory, is configured to:
separate the digital MR image volume into a plurality of digital MR image slices; and
perform slice refinement for each digital MR image slice by:
generating an image slice histogram;
determining an image slice landmark from the image slice histogram; and
generating a transformed digital MR image slice by applying a transformation function to the image slice to align the image slice landmark with a reference landmark, wherein the transformation function comprises applying a scaling factor of $\gamma = A/J$ to the image slice histogram where J is the intensity of the image slice landmark, and A is intensity of the reference landmark so that the transformed digital MR image slices are scaled digital MR image slices.

48. The system of claim 47, wherein the reference landmark comprises an image slice landmark from the histogram of an atlas image slice, an image slice landmark from a histogram of one of the image slices from the image volume, an image slice landmark from a histogram of an image slice from a different image volume, a landmark from a histogram of an image volume, or an image slice landmark of a histogram of an image slice.

49. The system of claim 47, wherein the transformation function further comprises shifting image slice intensity values by an image slice shifting factor to align the image slice landmark with the reference landmark so that the transformed digital MR image slices are shifted and scaled digital MR image slices.

50. The system of claim 47, wherein the image slice landmarks of the image slice histograms are modes of each corresponding histogram.

\* \* \* \* \*